United States Patent
Yokoyama et al.

(10) Patent No.: US 6,310,070 B1
(45) Date of Patent: Oct. 30, 2001

(54) PURINE DERIVATIVES AND MEDICINAL USE THEREOF

(75) Inventors: Akihisa Yokoyama, Urawa; Sumitsugu Kisanuki, Toda; Yoshikazu Matsuda, Kawagoe; Junko Matsui; Yoshiaki Isobe, both of Toda, all of (JP)

(73) Assignee: Japan Energy Corporation, Tokyo (JP)

( * ) Notice: Subject to any disclaimer, the term of this patent is extended or adjusted under 35 U.S.C. 154(b) by 0 days.

(21) Appl. No.: 09/462,861

(22) PCT Filed: Jul. 10, 1998

(86) PCT No.: PCT/JP98/03109

§ 371 Date: Apr. 28, 2000

§ 102(e) Date: Apr. 28, 2000

(87) PCT Pub. No.: WO99/03858

PCT Pub. Date: Jan. 28, 1999

(30) Foreign Application Priority Data

Jul. 15, 1997 (JP) .................................................. 9-205290

(51) Int. Cl.$^7$ ...................... C07D 473/30; C07D 233/88; A61K 31/522; A61P 13/12
(52) U.S. Cl. ........................ 514/262; 544/265; 548/326.5
(58) Field of Search .............................. 544/265; 514/262

(56) References Cited

U.S. PATENT DOCUMENTS

| 5,602,140 | 2/1997 | Isobe et al. ............................. 514/262 |
| 5,734,053 | * 3/1998 | Terrett .................................. 544/265 |
| 5,831,092 | 11/1998 | Izawa et al. ........................... 544/244 |
| 5,861,404 | * 4/2000 | Niewhoner ............................ 544/265 |
| 6,124,303 | * 9/2000 | Pamukcu ............................... 514/262 |

FOREIGN PATENT DOCUMENTS

| 0 675124 A2 | 10/1995 | (EP) . |
| 0 728 757 A1 | 8/1996 | (EP) . |
| 7-316157 | 12/1995 | (JP) . |
| 7-316158 | 12/1995 | (JP) . |
| 8-291175 | 11/1996 | (JP) . |

OTHER PUBLICATIONS

Leaker et al., "Effect of Enalapril on Proteinuria and Renal Function in Patients With Healed Severe Crescentic Glomerulonephritis," *Nephrology Dialysis Transplantation*, (1991) vol. 6, pp. 936–938.

Lai et al., "Cyclosporin Treatment of IgA Nephropathy: a Short Term Controlled Trial," *British Medical Journal*; (Nov. 7, 1987) vol. 295, pp. 1165–1168.

Niwa et al., "Clinical Effects of Selective Thromboxane A$_2$ Synthetase Inhibitor in Patients With Nephrotic Syndrome," *Clinical Nephrology*, (1988) vol. 30, No. 5, pp. 276–281.

Bertani et al., "Platelet Activating Factor (PAF) as a Mediator of Injury in Nephrotoxic Nephritis," *Kidney International*, (1987) vol. 31, pp. 1248–1256.

Border et al., "Suppression of Experimental Glomerulonephritis by Antiserum Against Transforming Growth Factor β1," *Nature*, (Jul. 26, 1990) vol. 346, pp. 371–374.

Shigematsu, "Jin to Tohseki," *Kidney and Dialysis*, (1991) vol. 31, pp. 202–206 and Translation of epologue.

Yoshihiro, "Jin to Tohseki," *Kidney and Dialysis*, (1994) vol. 43, No. 4, pp. 555–560, and translation of epologue.

\* cited by examiner

*Primary Examiner*—Mark L Berch
(74) *Attorney, Agent, or Firm*—Testa, Hurwitz & Thibeault, LLP

(57) ABSTRACT

A novel purine derivative exhibiting an effect to control inflammatory symptoms characteristic to nephritis and a medicine comprising this compound as an effective ingredient are provided. The compound is represented by the following general formula (I),

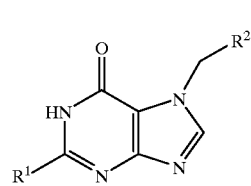

(I)

wherein $R^1$ is a hydrocarbon group having 17 or less carbon atoms and $R^2$ is a hydrocarbon group having 16 or less carbon atoms, wherein one or more $CH_2$ groups in the hydrocarbon group which 7013 do not directly bind with the carbon atom at 2 or 7 position of the purine ring replaced are by carbonyl groups, sulfonyl groups, O, or S and/or one or more CH groups in the hydrocarbon group which do not directly bind with the carbon atom at 2 or 7 position of the purine ring are replaced by N, C-halogen, or C—C≡N, or a pharmaceutically acceptable salt thereof.

13 Claims, No Drawings

PURINE DERIVATIVES AND MEDICINAL USE THEREOF

FIELD OF THE INVENTION

The present invention relates to novel purine derivatives or pharmaceutically acceptable salts thereof and their application as medicines. The medicine comprising a purine derivative or a pharmaceutically acceptable salt thereof of the present invention as an active ingredient is useful as a nephritis curative medicine, particularly as a medicine for improving proteinuria due to glomerulo nephritis and preventing aggravation of nephritis. Due to these curative effects, the medicine is expected to improve the quality of life for nephritis patients and to deter or avoid the introduction of dialysis to those patients.

BACKGROUND OF THE INVENTION

Presently, with the exception of certain kidney diseases, a causitive therapy vital for the treatment of chronic nephritis has not yet been realized. Most medical treatments currently applied to nephritis therefore aim at relaxation of symptoms and retardation or prevention of progression of the disease. A drug therapy, as well as confinement of daily behavior and dietetics, is the major treatment of chronic nephritis. As a drug therapy, an oral steroid drug is used as the primarily chosen medicine, in addition to conventional anti-platelet drugs. A cocktail treatment, in which four types of drugs (i.e. an immunosuppressive drug, a blood coagulation inhibitor and steroid, an immunosuppressive drug, an anti-platelet drug and blood coagulation inhibitor) simultaneously administered, is applied to the treatment of refractory nephritis and rapidly progressive glomerulo nephritis which are difficult to be cured by conventional drugs (Kidney and Dialysis, 34, 555 (1994)).

On the other hand, efforts for establishing new drugs and methods of treatment for nephritis have been undertaken in recent years. These efforts have matured into the development of an angiotensin converting enzyme inhibitor for the treatment of chronic nephritis or nephrotic syndrome (Nephrol. Dial. Transplant., 6, 936 (1993)) and the development of a novel immunosuppressive drug called cyclosporin which is used for the treatment of refractory nephrotic syndrome (Brit. Med. J., 295, 1165 (1987)), for example. Other drugs in which the introduction of is under study include, a thromboxanes synthetic enzyme inhibitor (Clin. Neph., 30, 276 (1988)), a platelet activating factor antagonist medicine (Kidney Int., 31, 1248 (1987)), various growth stimulating factors such as transforming growth factory-β, and cytokines as well as their receptor inhibitors (Nature, 346, 371 (1990)). In addition, LDL apheresis has been applied to the treatment of focal sclerosing glomerulonephritis which presents concomitant with hyper lipemia, and found to be effective for the improvement of proteinuria and retardation of kidney function disorder. (Kidney and Dialysis, 34, 555 (1994)).

Although these various methods of treatment have been proven to exhibit certain clinical effects, a medicine effective for the treatment of nephritis without any adverse side effects has yet to be discovered. Establishment of an effective treatment method for nephritis is essential not only to retard introduction of dialysis to a nephritis patient and improve the quality of life for the patient, but also to improve treatment economy. For these reasons, the development of a medicine which can be effectively applied to the treatment of nephritis has been pursued. The present inventors have also proposed and filed an application for a patent relating to the use of purine derivatives exhibiting an anti-inflammation function as an agent for the treatment of nephritis (Japanese Patent Application Laid-open No. 316158/1995). However, development of a novel and more effective drug for the treatment of nephritis has long been anticipated.

DISCLOSURE OF THE INVENTION

The present invention has been accomplished in order to overcome the problems described above. Specifically, an object of the present invention is to provide a novel compound exhibiting a depression effect on an inflammation which is peculiar to nephritis and a pharmaceutical composition for the treatment of nephritis which comprises this novel compound as an active ingredient. The present inventors have undertaken extensive studies to develop a novel compound effective for suppressing inflammatory disease and have found novel purine compounds and their derivatives, and evaluated their biological activities to discover that these compounds possess a certain biological activity effective for the treatment of nephritis. This finding has led to the completion of the present invention.

Accordingly, an object of the present invention is to provide purine derivatives of the following general formula (I),

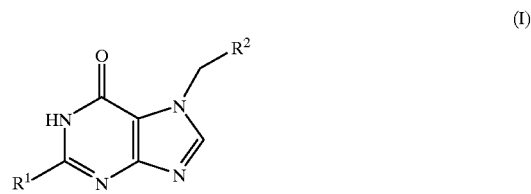

wherein $R^1$ is a hydrocarbon group having 17 or less carbon atoms or a group in which one or more $CH_2$ groups in the hydrocarbon group which do not directly bind with the carbon atom at 2 position of the purine ring are replaced by carbonyl groups, sulfonyl groups, O, or S and/or in which one or more CH groups in the hydrocarbon group which do not directly bind with the carbon atom at 2 position of the purine ring are replaced by N, C-halogen, or C—C≡N; and $R^2$ is a hydrocarbon group having 16 or less carbon atoms or a group in which one or more $CH_2$ groups in the hydrocarbon group which do not directly bind with the methylene group on the nitrogen atom at 7 position of the purine ring are replaced by carbonyl groups, sulfonyl groups, O, or S and/or in which one or more CH groups in the hydrocarbon group which do not directly bind with the methylene group on the nitrogen atom at 7 position of the purine ring are replaced by N, C-halogen, or C—C≡N, or pharmaceutically acceptable salts thereof. Another object of the present invention is to provide a pharmaceutical composition for the treatment of nephritis comprising said purine derivative or a pharmaceutically acceptable salt thereof as an active ingredient.

As depicted in the test examples hereinafter, the pharmaceutical composition for the treatment of nephritis of the present invention exhibits a pharmacological action to relax and retard the pathology caused by primary nephritis of various types which include an acute inflammatory reaction, immunoreaction, and various kidney function disorders due to blood vessel operative substances, as well as secondary nephritis caused by diabetic mellitus and hypertension.

The novel purine derivatives of the present invention will now be described in detail. The purine ring skeleton of the purine derivative possesses a 7-methylhypoxanthine(6-oxo-7-methylpurine) skeleton which is a tautomerism structure of 7-methylpurin-6-ol, with the 2 position being replaced by substituent $R^1$— and the 7 position by substituent $R^2$—$SH_2$—, respectively. The novel purine derivatives are described as hypoxanthine derivatives, although these compounds possess both hypoxanthine(6-oxopurine) and purine-6-ol(6-hydroxypurine) which are mutually tautomeric. In addition, in the above-mentioned general formula (I) there is a hypoxanthine (6-oxopurine) skeleton wherein the hydrogen atom on the nitrogen atom of 1 position transfers onto the nitrogen atom at 3 position. These structures are also in the relationship of tautomerism and included in the present invention.

Given as examples of pharmaceutically acceptable salts of the purine derivatives of the present invention are salts of a pharmaceutically acceptable acid such as hydrochloride, sulfate, acetate, hydrobromate, phosphate, succinate, maleate, fumarate, citrate, gluconate, methanesulfonate, and p-toluenesulfonate, and salts of a pharmaceutically acceptable cation such as sodium salt, potassium salt, and calcium salt. The pharmaceutically acceptable salts of the purine derivative can be prepared by recrystallization, or the like, of a mixture of the purine derivative and a corresponding acid or base.

The groups $R^1$ and $R^2$ which characterize the purine derivatives of the present invention will now be described in more detail. The groups $R^1$ and $R^2$ are respectively selected from a hydrocarbon group or a group derived from the hydrocarbon group by replacing one or more CH or $CH_2$ g roups by other groups. An outline of the hydrocarbon group and the group which is derived from the hydrocarbon group in the present invention is first described, and then the hydrocarbon group and the group derived from the hydrocarbon group which are respectively selected for the groups $R^1$ and $R^2$ are described in detail by way of a specific example. In $R^1$, $CH_2$ or CH which does not directly bond to the carbon atom at 2 position of the purine ring in the hydrocarbon group indicates the $CH_2$ or CH other than the carbon atom in which a free valence which directly bonds the 2 position carbon atom of the purine ring in said mono-valence group is present. Similarly, in $R^2$, $CH_2$ or CH which does not directly bond to the methylene group on the nitrogen atom at 7 position of the purine ring in the hydrocarbon group indicates the $CH_2$ or CH other than the carbon atom in which a free valence which directly bonds the methylene group on the nitrogen atom at 7 position of the purine ring in said mono-valence group is present.

Accordingly, $CH_2$ in the above-mentioned hydrocarbon group indicates $CH_2$ of —$CH_2$—, $CH_2$ of —$CH_3$, or $CH_2$ of =$CH_2$. When $CH_2$ of —$CH_2$— or $CH_2$ of —$CH_3$ is replaced by a carbonyl group, sulfonyl group, O, or S, these are respectively converted into —CO—(carbonyl group; ketone structure), —$SO_2$—(sulfone), —O—(ether structure), —S—(thioether structure) or —CO—H (—CHO formyl group; aldehyde structure), —$SO_2$—H, —O—H (hydroxyl group; alcohol structure), or —S—H (mercapto group; thiol structure). When $CH_2$ of =$CH_2$ is replaced by O or S, the $CH_2$ is converted into =O (oxo group: ketone structure) or =S (thioxo group; thioketone structure). CH in the above-mentioned hydrocarbon group indicates CH of —$CH_2$—, CH of —$CH_3$, CH of =CH—, CH of >CH—, CH of =$CH_2$, or CH of ≡CH. When the CH is replaced by N, they are respectively converted into —NH— (imino group), —$NH_2$(amino group), =N—, >N—, =NH, ≡N (nitrilo group). Replacing CH with a C-halogen or C—CN corresponds to substitution of a halogeno group or cyano group on said carbon atom. After such substitutions, if there is a $CH_2$ or CH still remaining on said carbon, the above-mentioned substitution can further be effected.

The hydrocarbon groups in the present invention include aliphatic hydrocarbon groups, aromatic hydrocarbon groups, and hydrocarbon groups which possess a combined structure of both the aliphatic and aromatic nature. The aliphatic hydrocarbon groups include those having a chain carbon skeleton, those having a cyclic carbon skeleton, and those having a chain carbon skeleton to which a cyclic structure is attached. Given as examples of the acyclic hydrocarbon group with a chain carbon skeleton are alkyl groups which are saturated hydrocarbon groups, alkenyl or alkynyl groups which are unsaturated hydrocarbon groups with a chain carbon skeleton, and alkadienyl groups having plural unsaturated bonds. These groups include those having either a linear or branched structure. Cyclic aliphatic hydrocarbon groups are alicyclic hydrocarbon groups which include cycloalkyl groups having a saturated monocyclic structure, cycloalkenyl or cycloalkynyl groups which are unsaturated hydrocarbon radicals having a cyclic carbon skeleton, and cycloalkadienyl groups which have a plurality of unsaturated bonds. As polycyclic aliphatic hydrocarbon groups, bicycloalkyl groups and the like which are cross-linking cyclic hydrocarbon radicals and spiro hydrocarbon groups in which the rings are combined by spiro atoms are given as examples. These polycyclic aliphatic hydrocarbon groups also include both saturated groups and unsaturated groups. In addition to the groups forming a condensed polycyclic structure, groups having an aggregated structure in which a plurality of rings directly bond via a carbon-carbon single bond or double bond, as well as those with a plurality of rings connected via a chain carbon skeleton, are also included. The alicyclic groups with a chain carbon skeleton having a cyclic structure added thereto are exemplified by the groups having a side chain on a cyclic hydrocarbon group or the groups having a cyclic structure as a substitution group on a carbon skeleton of alicyclic hydrocarbon group. For example, terpenoid hydrocarbon radicals are also included in the aliphatic hydrocarbon groups.

Aromatic hydrocarbon groups means hydrocarbon radicals including a cyclic group which shows aromaticity. Such groups may be, for example, aromatic monocyclic hydrocarbon groups and condensed polycyclic hydrocarbon groups, those containing a plurality of aromatic rings bonded by carbon-carbon bonds, or those having a plurality of aromatic rings bonded by chain carbon skeletons. Moreover, the groups with side chains on these aromatic rings are also included. The hydrocarbon groups with a composite structure of an aliphatic hydrocarbon group and aromatic hydrocarbon group include, for example, aralkyl groups (aryl alkyl groups), aryl alkenyl groups, and the like which are aliphatic hydrocarbon groups substituted with an aromatic hydrocarbon group, as well as polycyclic aromatic groups wherein one of the aromatic rings are added with hydrogen and converted into an aliphatic hydrocarbon chain.

A lower limit of carbon atom numbers included in the above-mentioned various hydrocarbon groups is naturally decided by their structures. The groups with an unstable structure, such as ketene structure of C=C=C, cyclopropenyl group, cyclopropynyl group, and cyclobutadienyl group, are excluded from the present invention.

The structures in which one or more of $CH_2$ which do not have a free valence in these hydrocarbon radicals are replaced by carbonyl groups, sulfonyl groups, O, or S indicate the conversion to the partial structures described below. If —$CH_2$— which is present in the midst of a carbon chain is replaced by a carbonyl group, or an oxo substitution occurs, the structure changes into a keto structure; if the —CH$_2$— group is replaced by a sulfonyl group, the alkyl group, for example, changes into a structure of a corresponding alkyl sulfonyl alkyl group; if replaced by O, the group takes an ether structure, for example, an alkyl group changes into a corresponding oxaalkyl group (alkyloxyalkyl group); and if replaced by S, the group takes thioether structure, for example, an alkyl group changes into a corresponding thiaalkyl group (alkylthioalkyl group). If the group CH$_2$ of CH$_3$— in the chain terminal is replaced by a carbonyl group, the group changes into an aldehyde structure, specifically into a formyl group (—CHO); if replaced by O, into a hydroxyl group (—OH); and if replaced by S, into a mercapto group (—SH). Furthermore, if the group CH$_2$ of CH$_2$= which is present at the chain terminal is replaced by O, the group changes into an oxo group (=O) or formyl group (—CHO) of aldehyde structure; and if replaced by S, into a thioxo group (=S) or thioformyl group (—CHS) of thioaldehyde structure. If the group —CH$_2$— in the carbon chain which forms a ring is replaced by O, the ring changes into an oxygen-containing heterocycle; if replaced by S, into a sulfur-containing heterocycle.

The structures in which one or more of CH, which do not have a free valence in these hydrocarbon radicals, are replaced by N, C-halogen, or C—C≡N indicate the conversion to the structures described below. Specifically, if CH of —CH$_2$— which is present in the midst of a carbon chain is replaced by N, the group changes into an imino group (—NH—); if replaced by C-halogen, into —CHX— (wherein X is a halogeno group) structure, i.e., halogeno substitution; and if replaced by C—C≡N, into —CH(CN)—, i.e., cyano substitution. The present invention includes the cases where the CH group in a —CHX— structure which is produced by C-halogen substitution or the CH group in a —CH(CN)— structure which is produced by C—C≡N substitution is further replaced by N, C-halogen, or C—C≡N. For example, a dihalogeno substitution structure, —CX$_2$— (wherein X is a halogeno group), is also included. If CH of the group >CH— which is present in the midst of a carbon chain is replaced by N, the carbon chain group changes into a nitrilo group (>N—); if replaced by C-halogen or C—C≡N, into a halogeno substitution group or cyano substitution group, respectively. If CH of the group CH$_2$= which is present at the terminal of a carbon chain is replaced by N, the group changes into an imino group (=NH); if CH of the group CH≡ at the terminal is replaced by N, the group changes into a nitrilo group (≡N). Moreover, if CH of the group CH$_3$ at the terminal is replaced by N, the group changes into an amino group (—NH$_2$); if replaced by C-halogen, into —CH$_2$X (wherein X is a halogeno group) structure, i.e., halogeno substitution; and if replaced by C—C≡N, into —CH$_2$—CN—, i.e., cyano substitution. In addition, the present invention includes a structure which is substituted by a plurality of halogeno groups such as —CHX$_2$ or CX$_3$, or a plurality of cyano groups (wherein X indicates a halogeno). If CH of —CH$_2$— or =CH— in a carbon chain which forms a ring is replaced by N, the ring changes into a nitrogen-containing heterocycle. The above-mentioned halogeno groups in the halogeno group substitution includes a chloro group, bromo group, iodo group, and fluoro group.

Various characteristic groups can be derived if a substitution in the above-mentioned CH$_2$ or CH occurs on an adjacent carbon atom. Examples of such characteristic group include oxygen-containing groups, such as carboxyl group (—COOH), oxycarbonyl group which is a carboxylic acid ester structure (R—O—CO—), acyloxy group (R—COO—), carbamoyl group (—CONH$_2$), N-substituted carbamoyl group, hydrazinocarbonyl group (—CO—NHNH$_2$), carbonyl imino carbonyl group (—CO—NH—CO—) corresponding to carboximide, oxy carbonyloxy group (R—O—CO—O—) which is a carbon acid ester structure, ureylene group which is a carbodiimide structure (—NH—CO—NH—), and carbamoyloxy group (—O—CONH$_2$) corresponding to a carbamate structure; sulfur-containing groups, such as thiocarboxyl group (—CSOH), dithiocarboxyl group (—CSSH), oxy thioxomethyl group (R—O—CS—) which is a thiocarboxylic acid ester structure, thiothioxomethyl group (R—S—CS—) which is a dithiocarboxylic acid ester structure, acylthio group (R—CO—S—), or the like, oxy thioxomethyloxy group (—O—CS—O—) or the like which is a thiocarbonic acid ester structure, sulfonic group (—SO$_3$H) which is a sulfonic acid structure, sulfoxy group (—SO$_4$H) or the like which is a sulfate structure, amino sulfonyl group (—SO$_2$—NH$_2$) or the like which is a sulfonic acid amide structure, and sulfoamino group (—NH—SO$_3$H) or the like which is a sulfonic acid halo-N-substituted sulfuric acid amide structure; and nitrogen-containing groups such as a hydrazino group (—NHNH$_2$), nitroso group (—N=O), hydroxy amino group (—NH—OH), hydroxy imino group (=N—OH) which is an oxime structure, amidino group (—C(=NH)NH$_2$), ureido group (—NH—CO—NH$_2$), aminothioxomethyl amino group (—NH—CS—NH$_2$), azo group (—N=N—), hydrazo group (—NH—NH—), and the like.

Among other groups such as ortho acid or an ester structure thereof (—C(OR)$_3$) which are generally regarded to be unstable, the groups which are in fact chemically stable are included in the structure of the present invention induced by the above-mentioned replacement. In addition, a structure in which a cyano group (—CN) directly bonds the carbon atom having a free valence, such as a cyano methyl group, a cyano group (—C≡N) formed from an ethynyl group (—C≡CH) in said hydrocarbon radical by substitution of CH with N, formyl group (—CH=O) formed from a vinyl group (—CH=CH$_2$) by substitution of the CH$_2$ with O, and carboxyl group (—C(OH)=O) derived by substitution of CH$_2$ with O and CH$_3$ with OH in iso-propenyl group (—C(CH$_3$)=CH$_2$) are also included in the groups which are induced by the above-mentioned replacement.

$R^1$ is selected from the group consisting of monovalence hydrocarbon groups having 17 or less carbon atoms and groups which are derived from these hydrocarbon groups. Such groups will now be described in detail giving specific examples. As examples of the hydrocarbon groups having 17 or less carbon atoms, non-cyclic or cyclic aliphatic hydrocarbon groups which are not included in aromatic hydrocarbon groups such as, for example, alkyl groups, cycloalkyl groups, alkenyl groups, cycloalkenyl groups, cycloalkadienyl groups, and alkynyl groups, as well as aromatic hydrocarbon groups, such as aromatic groups, aromatic group-substituted alkyl groups, aromatic group-substituted alkenyl groups, and the like, can be given.

More specifically, given as examples of the alkyl groups are methyl group, ethyl group, propyl group, isopropyl group (1-methylethyl group), butyl group, isobutyl group (2-methylpropyl group), sec-butyl group (1-methylpropyl group), pentyl group, 1-methylbutyl group, l-ethylpropyl group, hexyl group, heptyl group, octyl group, nonyl group, decyl group, undecyl group, dodecyl group, tridecyl group, tetradecyl group, pentadecyl group, hexadecyl group, heptadecyl group, 2-methylpropyl groups, 2-methylbutyl groups, 3-methylbutyl groups, methylpentyl group, methylhexyl group, methylheptyl group, methyloctyl group, methylnonyl group, tert-butyl group (1,1-dimethylethyl group), tert-pentyl group (1,1-dimethyl propyl group), neopentyl group (2,2-dimethylpropyl group), 2,6-dimethylheptyl group, 3,7-dimethyloctyl group, 2-ethylhexyl group, and the like. As examples of cycloalkyl substituted alkyl groups, cyclopentyl methyl group, cyclohexyl methyl group, and the like can be given. As examples of cycloalkyl groups and alkyl substituted cycloalkyl groups, cyclopropyl group, cyclobutyl group, cyclopentyl group, methyl cyclopentyl group, cyclohexyl group, methyl cyclohexyl group, cycloheptyl group, cyclooctyl group, and the like are given.

As examples of bicycloalkyl group which is one example of saturated alicyclic hydrocarbon group with a bridge structure, a norbornyl group, bicyclo[2.2.2]octyl group, and the like are given.

As examples of alkenyl groups, vinyl group, allyl group (2-propenyl group), 2-butenyl group (crotyl group), isopropenyl group (1-methylethenyl group), and the like can be given.

As examples of cycloalkenyl groups or cycloalkadienyl groups, cyclopentenyl group, cyclopentadienyl group, cyclohexenyl group, cyclohexadienyl group, and the like are given. As alkynyl groups, for example, ethynyl group, propynyl group, butynyl group, and the like are given.

As examples of aromatic groups, phenyl group, 1-naphthyl group, 2-naphthyl group, 9-anthryl groups, and the like can be given.

As examples of aromatic groups having a side chain, tolyl group (methylphenyl group), xylyl group (dimethylphenyl group), trimethylphenyl group, ethylphenyl group, methylethyl phenyl group, diethylphenyl group, triethylphenyl group, propylphenyl group, dipropylphenyl group, butylphenyl group, dibutylphenyl group, dibutylmethylphenyl group, pentylphenyl group, hexylphenyl group, heptylphenyl group, octylphenyl group, cyclohexylmethylphenyl group, (2-cyclohexylethyl)phenyl group, (3-cyclohexylpropyl)phenyl group, and the like can be given.

As examples of aromatic groups forming an aggregated cyclic structure with other rings, phenylphenyl group, cyclopentylphenyl group, cyclohexylphenyl group, and the like are given.

As examples of aromatic group substituted alkyl groups, benzyl group, phenethyl group, α-methylbenzyl group, phenylpropyl group, phenylbutyl group, phenylpentyl group, phenylhexyl group, methylbenzyl group, methylphenethyl group, dimethylbenzyl group, dimethylphenethyl group, trimethylbenzyl group, ethylbenzyl group, diethylbenzyl group, and the like are given. As examples of aromatic group substituted alkenyl groups, styryl group, methylstyryl group, ethylstyryl group, dimethylstyryl group, cinnamyl group (3-phenyl-2-propenyl group), and the like can be given.

In $R^1$, given as the groups in which $CH_2$ in said hydrocarbon group is replaced by a carbonyl group, sulfonyl group, O, or S, and, or the groups in which CH is replaced by N, C-halogen, or C—CN, are the groups containing at least one structure selected from the group consisting of a ketone structure, aldehyde structure, carboxylic acid structure, ester structure, thioester structure, amide structure, carbonate structure, carbamate structure, sulfone structure, sulfonamide structure, ether structure, thioether structure, amine structure, alcohol structure, thiol structure, halogeno substituted structure, cyano substituted structure, oxygen-containing heterocyclic structure, sulfur-containing heterocyclic structure, and nitrogen-containing heterocyclic structure.

More specifically, as examples of the group containing a ketone structure, acetylmethyl group, acetylethyl group, acetylphenyl group,. acetylbenzyl group, and the like can be given. As examples of the group containing an aldehyde structure, formylmethyl group, formylethyl group, formylphenyl group, formylbenzyl group, and the like can be given. As examples of the group which contain a carboxylic acid structure, hydroxycarbonylmethyl group, hydroxycarbonylethyl group, hydroxycarbonylphenyl group, hydroxycarbonylbenzyl group, and the like can be given. As examples of the group which contains an ester structure, methoxycarbonylmethyl group, ethoxycarbonylmethyl group, methoxycarbonylethyl group, methoxycarbonylphenyl group, methoxycarbonylbenzyl group, acetoxymethyl group, acetoxyphenyl group, benzoyloxymethyl group, and the like can be given. As examples of the groups containing a thioester structure, methylthiocarbonylmethyl group, methylthiocarbonylphenyl group, acetylthiophenyl group, and the like can be given. As examples of the group containing an amide structure, acetylaminomethyl group, acetylaminoethyl group, aminocarbonylphenyl group, methylaminocarbonylphenyl group, and the like can be given.

As examples of the group having a carbonate structure, methoxycarbonyloxymethyl group, methoxycarbonyloxyphenyl group, ethoxycarbonyloxyphenyl group, and the like are given. As examples of the group having a carbamate structure, methoxycarbonylaminophenyl group, phenylaminocarbonyloxy methyl group, and the like are given. As examples of the group having a sulfone structure, methanesulfonylmethyl group, methanesulfonylphenyl group, and the like are given. As examples of the group having a sulfonic acid amide structure, aminosulfonylmethyl group, aminosulfonylethyl group, aminosulfonylphenyl group, and the like are given. As examples of the group containing an ether structure, methoxymethyl group, methoxyethyl group, ethoxyethyl group, methoxypropyl group, butoxyethyl group, ethoxyethoxyethyl group, methoxyphenyl group, dimethoxyphenyl group, phenoxymethyl group, and the like are given. As examples of the group containing a thioether structure, methylthiomethyl group, methylthiophenyl group, methylthiobenzyl group, and the like are given.

As examples of the group containing an amine structure, 2-aminoethyl group, methylaminomethyl group, dimethylaminomethyl group, methylaminoethyl group, propylaminomethyl group, cyclopentylaminomethyl group, 2-aminopropyl group, 3-aminopropyl group, aminobutyl group, aminophenyl group, diaminophenyl group, aminomethylphenyl group, and the like are given. As examples of the group containing an alcohol structure (including a phenol structure), 2-hydroxyethyl group, 2-hydroxypropyl group, 3-hydroxypropyl group, 2,3-dihydroxypropyl group, hydroxybutyl group, hydroxyphenyl group, dihydroxyphenyl group, hydroxymethylphenyl group, hydroxyethylphenyl group, dimethylhydroxyphenyl group, diethylhydroxyphenyl group, dipropylhydroxyphenyl group, dibutylhydroxyphenyl group, and the like are given. As examples of the group containing a thiol structure (including a thiophenol structure), 2-mercaptoethyl group, 2-mercaptopropyl group, 3-mercaptopropyl group, mercaptobutyl group, mercaptophenyl group, and the like are given.

As examples of the group containing a halogeno substituted structure, 2-chloroethyl group, 2-chloropropyl group, 3-chloropropyl group, chlorobutyl group, fluorophenyl group, chlorophenyl group, bromophenyl group, difluorophenyl group, dichlorophenyl group, dibromophenyl group, chlorofluorophenyl group, trifluorophenyl group, trichlorophenyl group, fluoromethylphenyl group, trifluoromethylphenyl group, and the like are given. As examples of the group containing a cyano-substituted structure, cyanoethyl group, cyanophenyl group, cyanobenzyl group, and the like are given.

As examples of the group containing an oxygen-containing heterocyclic structure, tetrahydrofuranyl group, tetrahydropyranyl group, furfuryl group, benzofurfuryl group, and the like are given. As examples of the group containing a sulfur-containing heterocyclic structure, thienyl group, benzothienyl group, and the like are given. As examples of the group containing a nitrogen-containing heterocyclic structure, pyrrolyl group, imidazoyl group, pyridyl group, pyrimidyl group, pyridazyl group, pyrazyl group, tetrazinyl group, quinolyl group, iso-quinolyl group, pyridylmethyl group, and the like are given.

Although in the above description, the groups containing only one structure, such as a ketone structure, aldehyde structure, carboxylic acid structure, ester structure, thioester structure, amide structure, carbonate structure, carbamate structure, sulfone structure, sulfonic acid amide structure, ether structure, thioether structure, amine structure, alcohol structure, thiol structure, halogeno-substituted structure, cyano-substituted structure, oxygen-containing heterocyclic structure, sulfur-containing heterocyclic structure, nitrogen-containing heterocyclic structure, are mentioned, the groups containing two or more of these structures are acceptable. As examples of the group containing two or more of above-mentioned structures simultaneously, aminohydroxyphenyl group, fluorohydroxyphenyl group, chlorohydroxyphenyl group, morpholylmethyl group, morpholylethoxy phenyl group, oxazoyl group, thiadiazoyl group, and the like can be given.

$R^2$ is selected from monovalent hydrocarbon groups having 16 or less carbon atoms or the groups induced from such hydrocarbon groups. Such groups will now be described in detail giving specific examples. As examples of the hydrocarbon group having 16 or less carbon atoms, non-cyclic or cyclic aliphatic hydrocarbon groups which are not included in aromatic hydrocarbon groups such as, for example, alkyl groups, cycloalkyl groups, alkenyl groups, cycloalkenyl groups, cycloalkadienyl groups, and alkynyl groups, as well as aromatic hydrocarbon-groups, such as aromatic groups, aromatic group-substituted alkyl groups, aromatic group-substituted alkenyl groups, and the like, can be given.

More specifically, given as examples of alkyl group are methyl group, ethyl group, propyl group, isopropyl group (1-methylethyl group), butyl group, isobutyl group (2-methylpropyl group), sec-butyl group (1-methylpropyl group), pentyl group, 1-methylbutyl group, hexyl group, 1-methylpentyl group, heptyl group, octyl group, nonyl group, decyl group, undecyl group, dodecyl group, 2-methylpropyl group, 2-methylbutyl group, 3-methylbutyl group, 2-methylpentyl group, 3-methylpentyl group, 4-methylpentyl group, methylhexyl group, methylheptyl group, methyloctyl group, methylnonyl group, tert-butyl group (1,1-dimethylethyl group), neopentyl group (1,1-dimethylpropyl group), 2,6 -dimethylheptyl group, 3,7-dimethyloctyl group, 2-ethylhexyl groups, and the like.

As examples of cycloalkyl-substituted alkyl group, cyclopentylmethyl group, cyclohexylmethyl group, and the like can be given.

As examples of cycloalkyl group and alkyl-substituted cycloalkyl group, cyclopropyl group, cyclobutyl group, cyclopentyl group, methylcyclopentyl group, cyclohexyl group, methylcyclohexyl group, cycloheptyl group, cyclooctyl group, and the like can be given.

As examples of bicycloalkyl group which is one example of saturated alicyclic hydrocarbon group with a bridge structure, a norbornyl group, bicyclo[2.2.2]octyl group, and the like are given.

As examples of alkenyl group, vinyl group, allyl group (2-propenyl group), 2-butenyl group (crotyl group), isopropenyl group (1-methylethenyl group), and the like can be given.

As examples of cycloalkenyl group and cycloalkadienyl group, cyclopentenyl group, cyclopentadienyl group, cyclohexenyl group, cyclohexanedienyl group, and the like are given. As alkynyl group, for example, ethynyl group, propynyl group, butynyl group, and the like are given.

As examples of aromatic group, phenyl group, 1-naphthyl group, 2-naphthyl group, phenylphenyl group, and the like can be given. As examples of aromatic group having a side chain, tolyl group (methylphenyl group), xylyl group (dimethylphenyl group), trimethylphenyl group, ethylphenyl group, methylethylphenyl group, diethylphenyl group, propylphenyl group, butylphenyl group, and the like are given.

As examples of aromatic group-substituted alkyl group, benzyl group, phenethyl group, α-methylbenzyl group, phenylpropyl group, phenylbutyl group, phenylpentyl group, phenylhexyl group, methylbenzyl group, methylphenethyl group, dimethylbenzyl group, dimethylphenethyl group, trimethylbenzyl group, ethylbenzyl group, diethylbenzyl group, and the like are given.

As examples of aromatic group-substituted alkenyl group, styryl group, methylstyryl group, ethylstyryl group, dimethylstyryl group, cinnamyl group (3-phenyl-2-propenyl group), and the like are given.

In $R^2$, given as the groups in which $CH_2$ in said hydrocarbon group is replaced by a carbonyl group, sulfonyl group, O, or S, or the groups in which CH is replaced by N, C-halogen, or C—CN, are the groups containing at least one structure selected from the group consisting of a ketone structure, aldehyde structure, carboxylic acid structure, ester structure, thioester structure, amide structure, carbonate structure, carbamate structure, sulfone structure, sulfonic acid amide structure, ether structure, thioether structure, amine structure, alcohol structure, thiol structure, halogeno substituted structure, cyano substituted structure, oxygen-containing heterocyclic structure, sulfur-containing heterocyclic structure, and nitrogen-containing heterocyclic structure.

More specifically, as examples of the group containing a ketone structure, acetylmethyl group, acetylethyl group, acetylphenyl group, acetylbenzyl group, and the like are given. As examples of the group containing aldehyde structure, formylmethyl group, formylethyl group, formylphenyl group, formylbenzyl group, and the like are given. As examples of the group containing a carboxylic acid structure, hydroxycarbonylmethyl group, hydroxycarbonylethyl group, hydroxycarbonylphenyl group, hydroxycarbonylbenzyl group, and the like are given. As examples of the group containing an ester structure, methoxycarbonylmethyl group, ethoxycarbonylmethyl group, methoxycarbonylethyl group, methoxycarbonylphenyl group, methoxycarbonylbenzyl group, acetoxymethyl group, acetoxyphenyl group, benzoyloxymethyl group, and the like are given. As examples of the group containing a thioester structure, methylthiocarbonylmethyl group, methylthiocarbonylphenyl group, acetylthiophenyl group, and the like are given. As examples of the group containing an amide structure, acetylaminomethyl group, acetylaminoethyl group, aminocarbonylphenyl group, methylaminocarbonylphenyl group, and the like are given.

As examples of the group containing a carbonate structure, methoxycarbonyloxymethyl group, methoxycarbonyloxyphenyl group, ethoxycarbonyloxyphenyl group, and the like are given. As examples of the group containing a carbamate structure, methoxycarbonylaminophenyl group, phenylaminocarbonyloxymethyl group, and the like are given. As examples of the group containing a sulfone structure, methanesulfonylmethyl group, methanesulfonylphenyl group, and the like are given. As examples of the group containing a sulfonic acid amide structure, aminosulfonylmethyl group, aminosulfonylethyl group, aminosulfonylphenyl group, and the like are given. As examples of the group containing an ether structure, methoxymethyl group, methoxyethyl group, ethoxyethyl group, methoxypropyl group, butoxyethyl group, ethoxyethoxyethyl group, methoxyphenyl group, dimethoxyphenyl group, phenoxymethyl group, and the like are given. As examples of the group containing a thioether structure, methylthiomethyl group, methylthiophenyl group, methylthiobenzyl group, and the like are given.

As examples of the group containing an amine structure, 2-aminoethyl group, methylaminomethyl group, dimethylaminomethyl group, methylaminoethyl group, propylaminomethyl group, cyclopentylaminomethyl group, 2-aminopropyl group, 3-aminopropyl group, aminobutyl group, aminophenyl group, diaminophenyl group, aminomethylphenyl group, and the like are given. As examples of the group containing an alcohol structure (including phenol structure), 2-hydroxyethyl group, 2-hydroxypropyl group, 3-hydroxypropyl group, 2,3-dihydroxypropyl group, hydroxybutyl group, hydroxyphenyl group, dihydroxyphenyl group, hydroxymethylphenyl group, hydroxyethylphenyl group, and the like are given. As examples of the group containing a thiol structure (including thiophenol structure), 2-mercaptoethyl group, 2-mercaptopropyl group, 3-mercaptopropyl group, mercaptobutyl group, mercaptophenyl group, and the like are given.

As examples of the group containing a halogeno-substituted structure, 2-chloroethyl group, 2-chloropropyl group, 3-chloropropyl group, chlorobutyl group, fluorophenyl group, chlorophenyl group, bromophenyl group, difluorophenyl group, dichlorophenyl group, dibromophenyl group, chlorofluorophenyl group, trifluorophenyl group, trichlorophenyl group, fluoromethylphenyl group, trifluoromethylphenyl group, and the like are given. As examples of the group containing a cyano-substituted structure, cyanoethyl group, cyanophenyl group, cyanobenzyl group, and the like are given. As examples of the group containing an oxygen-containing heterocyclic structure, tetrahydrofuranyl group, tetrahydropyranyl group, furfuryl group, benzofurfuryl group, and the like are given. As examples of the group containing a sulfur-containing heterocyclic structure, thienyl group, benzothienyl group, and the like are given. As examples of the group containing a nitrogen-containing heterocyclic structure, pyrrolyl group, imidazoyl group, pyridyl group, pyrimidyl group, pyridazyl group, pyrazyl group, tetrazinyl group, quinolyl group, iso-quinolyl group, pyridylmethyl group, and the like are given.

Although in the above description, the groups containing only one structure, such as a ketone structure, aldehyde structure, carboxylic acid structure, ester structure, thioester structure, amide structure, carbonate structure, carbamate structure, sulfone structure, sulfonic acid amide structure, ether structure, thioether structure, amine structure, alcohol structure, thiol structure, halogeno-substituted structure, cyano-substituted structure, oxygen-containing heterocyclic structure, sulfur-containing heterocyclic structure, nitrogen-containing heterocyclic structure, are mentioned, the groups containing two or more of these structures are acceptable. As examples of the group containing two or more of the above-mentioned structures simultaneously, aminohydroxyphenyl group, fluorohydroxyphenyl group, chlorohydroxyphenyl group, morpholylmethyl group, morpholylethoxyphenyl group, oxazoyl group, thiadiazoyl group, and the like can be given.

As mentioned above, the groups $R^1$ and $R^2$ which characterize the purine derivatives of the present invention are respectively selected from a hydrocarbon group or a group derived from the hydrocarbon group by replacing one or more CH or $CH_2$ groups by other groups. However, because the purine derivatives of the present invention are used for pharmaceutical application, functional groups in the radicals induced from these groups should preferably be selected from those not forming an intermolecular bond by reactions. Specifically, if such an intermolecular reaction between molecules occurs when dissolved in a solvent, the reaction product is something different from a purine derivative. The purine derivative which is free from this type of intermolecular reaction is preferred as a medicine. In addition, it is desirable for the purine derivative of the present invention not to be deteriorated by the reaction with additives or solvents used when a drug composition is prepared therefrom, or by the reaction with moisture or oxygen in the atmosphere. Similarly, it is desirable that the purine derivative will not deteriorate due to a transfer or dissociation reaction when processed by heating or the like during preparation of a pharmaceutical agent.

Each step of the process for preparing the purine derivatives of the present invention will now be outlined.

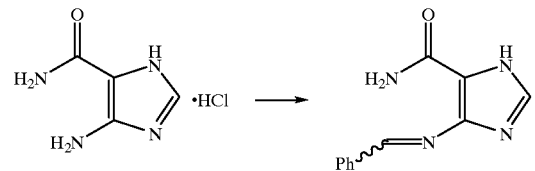

First of all, 4-amino-5-imidazolecarboxamide hydrochloride (AICA—HCl) and benzaldehyde are reacted at a temperature of 0–100° C. using no solvent or using a solvent in which both compounds are dissolvable, preferably in the presence of an acid or a base, to produce 4-benzylideneamino-5-imidazolecarboxamide. As an acid, p-toluenesulfonic acid, camphor sulfonic acid (camphor-10-sulfonic acid), and the like are desirable. As a base, a tertiary amine such as triethylamine, pyridine, and the like are desirable. An intermediate 4-benzylideneamino-5-imidazolecarboxamide which is a compound with the amino group at the 4 position being protected with a benzylidene group can be obtained almost quantitatively from the raw material AICA—HCl.

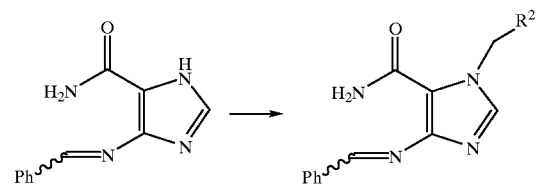

4-Benzylideneamino-5-imidazolecarboxamide prepared in the first step is reacted with an alkylating agent ($R^2CH_2$—Y) at a temperature of 0–100° C. using no solvent or using a solvent in which both compounds are dissolvable, preferably in the presence of a base to effect a site selective N-alkylation reaction, thereby 1-(substituted methyl)-4-benzylideneamino-5-imidazolecarboxamide is obtained. As a base, sodium carbonate, potassium carbonate, and the like are desirable. 1-(substituted methyl)-4-benzylideneamino-5-imidazolecarboxamide can be obtained almost quantitatively from the intermediate, 4-benzylideneamino-5-imidazolecarboxamide.

As the alkylating agent ($R^2CH_2$—Y), for example, the compounds wherein Y is a halogeno group such as a chloro group, bromo group, or iodo group, i.e. alkyl chloride, alkyl bromide, and alkyl iodide, or the compounds wherein Y is an organo sulfonyloxy group (R—$SO_3$—), i.e. alkyl methanesulfonate, alkyl p-toluenesulfonate, and the like, can be used.

If there is a nucleophilic substituent such as a hydroxyl group or amino group on the $R^2CH_2$— group to be introduced, the alkylation reaction in the second step may be carried out after introducing a protective group using a reagent which introduce the corresponding substituent, as required. The protective group is subsequently removed to obtain the target compound.

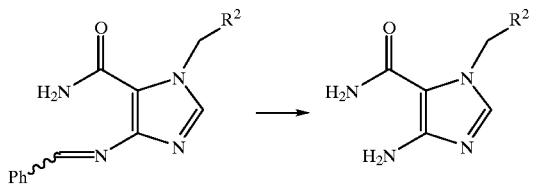

The benzylideneamino group in 1-(substituted methyl)-4-benzylideneamino-5-imidazolecarboxamide obtained in the second step is hydrolyzed with an acid to obtain 4-amino-1-(substituted methyl)-5-imidazolecarboxamide. As an acid, hydrochloric acid, sulfuric acid, and the like are suitable. An acid salt of the 4-amino-1-(substituted methyl)-5-imidazolecarboxamide can be produced almost quantitatively from 1-(substituted methyl)-4-benzylidene amino-5-imidazolecarboxamide. If necessary, the resulting product is treated with a base to isolate 4-amino-1-(substituted methyl)-5-imidazolecarboxamide as a free amine.

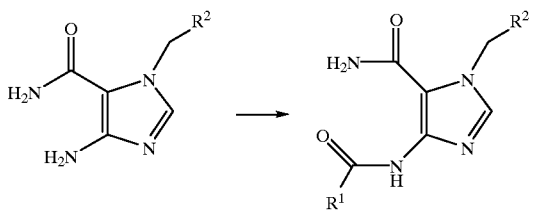

4-Amino-1-(substituted methyl)-5-imidazole carboxamide (acid salt) obtained in the third step and a carboxylic acid derivative ($R^1CO$—Y) are reacted to produce 4-(acylamino)-1-(substituted methyl)-5-imidazole carboxamide. A simple method for carrying out an acylation reaction comprises using an acid halide or acid anhydride which are carboxylic acid derivatives in the presence of a tertiary amine such as triethylamine or pyridine. An activated esterification method using dicyclohexylcarbodiimide, 1-(3-dimethylaminopropyl)-3-ethylcarbodiimide hydrochloride, and diphenyl chlorophosphate can be used depending on the structure of the acyl group to be introduced.

If there is a nucleophilic substituent such as a hydroxyl group or an amino group on the $R^1$ g roup to be introduced, the acylation reaction in the fourth step may be carried out after introducing a protective group, as required. The protective group is subsequently removed to obtain the target compound.

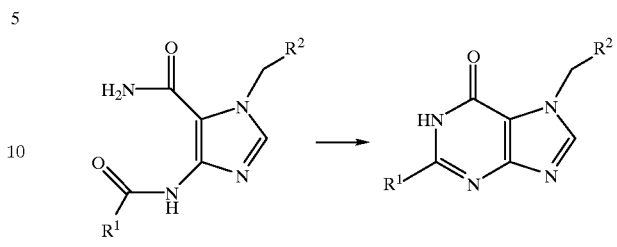

The 4-(acylamino)-1-(substituted methyl)-5-imidazole carboxamide obtained in the fourth step is reacted using a base at 0–150° C. in a solvent which can dissolve the base to effect a condensation-cyclization reaction, thereby producing 2,7-substituted hypoxanthine. As a base, an alkali metal hydroxide such as sodium hydroxide and potassium hydroxide, or an alkali metal carbonate such as sodium carbonate, potassium carbonate, and the like are used. As a solvent, a lower alcohol such as methyl alcohol, ethyl alchohol, propyl alcohol can preferably be used.

When there is a protective group in the substituent which is introduced in the N-alkylation reaction of the second step or the N-acylation reaction in the fourth step, each protective group is removed using a releasing method appropriate for the respective protective group, to produce a purine derivative which possesses objective $R^1$ g roup and $R^2$ g roup.

In the pharmaceutical composition of the present invention, the purine derivatives of the general formula (I) or the pharmaceutically acceptable salts thereof to be used as active components are characterized by the group $R^2$—$CH_2$— which is a substitutent on the nitrogen atom at the 7 position and the group $R^1$ which is a substituent at the 2 position of the purine ring skeleton. Preferred embodiments of the purine derivatives of the general formula (I) to be used as a medicine for treating nephritis will now be described in detail.

The treating effect for nephritis of the purine derivatives of the general formula (I) is largely dependent upon selection of the group $R^2$—$CH_2$—, a substituent on the nitrogen atom at 7 position of the purine ring skeleton. In addition, the treating effect is promoted by the selection of the group $R^1$ which is a substituent on the 2 position of the purine ring. A preferred scope of the group $R^2$—$CH_2$— which is a substituent on the nitrogen atom at 7 position of the purine ring skeleton is first described. $R^2$ which forms the substituent group $R^2$—$CH_2$— is selected from group consisting of hydrocarbon groups having 16 or less carbon atoms and various groups derived from those hydrocarbon groups by the aforementioned substitutions. Generally, preferred groups are groups including a cyclic structure, more specifically, groups having a monocyclic hydrocarbon structure or a similar heterocyclic structure in which the carbon atom in said monocyclic hydrocarbon structure is replaced by a nitrogen atom, oxygen atom, or sulfur atom. Given as preferred examples of the monocyclic hydrocarbon groups are monocyclic aromatic group such as a phenyl group, cycloalkyl group, cycloalkenyl group, cycloalkadienyl group, and the like; corresponding heterocyclic groups, for example, nitrogen-containing heteroaromatic ring groups, which include hexacyclic groups such as pyridyl group or pyrimidyl group and pentacyclic groups such as pyrrolyl group or imidazolyl group; oxygen-containing heteroaromatic pentacyclic groups such as furyl group; and sulfur-containing heteroaromatic pentacyclic groups such as thienyl group; heteroaromatic pentacyclic groups containing nitrogen, and sulfur or oxygen such as oxazolyl group and thiazolyl group. The structure formed by connecting these cyclic groups with a methylene group —$CH_2$— in the carbon chain $R^2$—$CH_2$— may also be used. In addition, the structure having hydrocarbon groups as substituents on these rings is also desirable. Among the groups including these monocyclic structures, particularly desirable groups for $R^2$ will now be described.

Among the groups including these monocyclic structures, particularly desirable groups for $R^2$ are the groups represented by the following general formula (A):

—$(CH_2)_m$—$(X)_n$—Ar      (A)

wherein m is an integer of 0, 1, or 2, n is an integer of 0 or 1, provided that when m is 0, n is 0, X is a group selected from —O—, —NH—, —NHCO—, —CONH—, —$NHSO_2$—, and —$SO_2NH$—, and Ar is a phenyl group without a substituent or with 1–3 substituents, wherein the substituents are selected from the group consisting of an alkyl group having 1–6 carbon atoms, halogeno group, hydroxyl group, alkoxyl group having 1–6 carbon atoms, amino group, amino group substituted by one alkyl group having 1–6 carbon atoms, amino group substituted by two alkyl groups having 1–3 carbon atoms, carbamoyl group, N-alkyl carbamoyl group having 1–6 carbon atoms, sulfamoyl group, N-alkyl sulfamoyl group having 1–6 carbon atoms, and trifluoromethyl group. When two or more substituents are present, such substituents may be either identical or different. The halogeno group which is given as an option for the substituent on the phenyl group expressed by Ar in the general formula (A) may includes a fluoro group, chloro group, bromo group, and iodo group, with preferred groups being fluoro group and chloro group. When a substituent is present on the phenyl group indicated by Ar in the general formula (A), such substituent is preferably selected from an alkyl group having 1–6 carbon atoms, fluoro group, chloro group, hydroxyl group, an alkoxyl group having 1–6 carbon atoms, amino group substituted by two alkyl groups having 1–3 carbon atoms, and trifluoromethyl group.

Another preferable example of $R^2$ is the group represented by the following general formula (B):

—$(CH_2)_m$—Ar      (B)

wherein m is an integer of 0, 1, or 2, and Ar is a phenyl group without a substituent or with 1–3 substituents, wherein the substituents are selected from the group consisting of an alkyl group having 1–6 carbon atoms, fluoro group, chloro group, hydroxyl group, alkoxyl group having 1–6 carbon atoms, amino group substituted by two alkyl groups having 1–3 carbon atoms, and trifluoromethyl group. When two or more substituents are present, such substituents may be either identical or different. In addition, when a substituent is present on the phenyl group which is indicated by Ar in the foregoing general formula (B), it is desirable that the number of substituents is 1 or 2. Moreover, a smaller length is desirable for the alkylene group —$(CH_2)_m$— in the general formula (B). Selection of m=0 is particularly desirable.

Although the treating effect for nephritis of the purine derivatives of the general formula (I) is largely dependent upon selection of the group $R^2$—$CH_2$—, a substituent on the nitrogen atom at 7 position of the purine ring skeleton, the treating effect is enhanced by the selection of the group $R^1$, a substituent on the 2 position of the purine ring. Preferred selection of the group $R^1$ which is a substituent on the 2 position of the purine ring is now described. As mentioned above, $R^1$ is selected from the group consisting of hydrocarbon groups having 17 or less carbon atoms and groups which are derived from those hydrocarbon groups by the above-mentioned substitution.

In general, when the group including a cyclic structure is selected as $R^1$, it is desirable to select such a group from monocyclic hydrocarbon groups and the groups containing a heterocyclic group having a similar structure with the monocyclic hydrocarbon group in which the carbon atom forming the ring thereof is replaced by a nitrogen atom, oxygen atom, or sulfur atom. Given as preferred examples of the monocyclic hydrocarbon groups are monocyclic aromatic groups such as phenyl group, cycloalkyl group, cycloalkenyl group, cycloalkadienyl group, and the like; corresponding heterocyclic groups, for example, nitrogen-containing heteroaromatic ring groups, which include hexacyclic groups such as pyridyl group or pyrimidyl group and pentacyclic groups such as pyrrolyl group or imidazolyl group; oxygen-containing heteroaromatic pentacyclic groups such as furyl group; and sulfur-containing heteroaromatic pentacyclic groups such as thienyl group; heteroaromatic pentacyclic groups containing nitrogen, and sulfur or oxygen such as oxazolyl group and thiazolyl group.

When a chain-type group is selected as $R^1$, it is desirable that the structure contains lesser unsaturated bonds in the skeleton. With the exception of functional groups induced by the aforementioned substitution, it is desirable that the carbon skeletons are selected from saturated structures. Therefore, ideal selection comprises an alkyl group which is a saturated hydrocarbon group; an oxa-substituted alkyl group, thio-substituted alkyl group, or aza-substituted alkyl group which are the structures in which a carbon atom in carbon chain skeleton is replaced by an oxygen atom, sulfur atom, or nitrogen atom; and a structure with additional substitution of a functional group which is induced by further replacement on the above-mentioned saturated structure.

More specific examples for the group $R^1$ are as follows. When a group containing a cyclic structure is selected as $R^1$, a phenyl group without a substituent or with 1–3 substituents is desirable. The substituent to be replaced on the phenyl group is preferably selected from the groups consisting of an alkyl group having 1–6 carbon atoms, halogen group, hydroxyl group, alkoxyl group having 1–6 carbon atoms, amino group, amino group substituted by one alkyl group having 1–6 carbon atoms, amino group substituted by two alkyl groups having 1–3 carbon atoms, carbamoyl group, N-alkyl carbamoyl group having 1–6 carbon atoms, sulfamoyl group, N-alkyl sulfamoyl group having 1–6 carbon atoms, and trifluoromethyl group. When two or more substituents are present, such substituents may be either identical or different.

Alternatively, it is also desirable to use a similar heterocyclic aromatic group containing an oxygen atom, sulfur atom, or nitrogen atom within a 5-member or 6-member ring, instead of a phenyl group. Specific examples include nitrogen-containing heteroaromatic ring groups, which include hexacyclic groups such as pyridyl group or pyrimidyl group and pentacyclic groups such as pyrrolyl group or imidazolyl group; oxygen-containing heteroaromatic pentacyclic groups such as furyl group; and sulfur-containing heteroaromatic pentacyclic groups such as thienyl group; heteroaromatic pentacyclic groups containing nitrogen, and sulfur or oxygen such as oxazolyl group and thiazolyl group. These 5 or 6-member heterocyclic aromatic groups may have additional substituents on the ring such as an alkyl group having 1–6 carbon atoms, halogeno group, hydroxyl group, alkoxyl group having 1–6 carbon atoms, amino group, amino group substituted by one alkyl group having 1–6 carbon atoms, amino group substituted by two alkyl groups having 1–3 carbon atoms, carbamoyl group, N-alkyl carbamoyl group having 1–6 carbon atoms, sulfamoyl group, N-alkyl sulfamoyl group having 1–6 carbon atoms, and trifluoromethyl group. Although the number of substituent allowable on these heteroaromatic ring groups is restricted by the number of replaceable hydrogen atoms on the ring, such a number is preferably 3 or less. When two or more substituents are present, such substituents may be either identical or different. The halogeno group which substitutes on the heteroaromatic ring group includes fluoro group, chloro group, bromo group, and iodine group, with preferred groups being fluoro group and chloro group.

When a group containing a cyclic structure is selected as $R^1$, the above-mentioned phenyl group with or without substituent is desirable. A similar 5 or 6-member heterocyclic aromatic group with or without substituent is also desirable. Among such a 5 or 6-member heterocyclic aromatic group, the group containing one or two oxygen, sulfur, or nitrogen atom is preferable, with particularly preferred being the group containing one oxygen, sulfur, or nitrogen atom, such as pyridyl group which is a hexacyclic group and pyrrolyl group, furyl group, or thienyl group which are pentacyclic groups. In addition, it is desirable to select the substituents on the phenyl group or the heterocyclic aromatic group from alkyl groups having 1–6 carbon atoms, fluoro group, chloro group, hydroxyl group, alkoxyl groups having 1–6 carbon atoms, amino group, alkyl amino groups having 1–6 carbon atoms, N-alkyl sulfamoyl groups having 1–6 carbon atoms, and trifluoromethyl group. Furthermore, it is desirable that either one of the two ortho positions in the phenyl group is not substituted. In addition, in the case where one of the ortho positions is substituted, the substituent should preferably be a small group such as methyl group, fluoro group, or chloro group. Similarly, in the heterocyclic aromatic group having a substituent, it is desirable that either one of the two skeleton atoms constituting the ring adjacent to the carbon atom which is bonded with the 2 position of the purine ring is not substituted. In addition, if one of these positions is substituted, the substituent should preferably be a small group such as, for example, methyl group, fluoro group, or chloro group.

When a group with a cyclic structure is selected as $R^1$, a more preferred selection is a phenyl group which may have one or two substituents, or a pyridyl group which corresponds to its one nitrogen substituent, where the pyridyl group may have one or two substituents. In addition, it is desirable to select the substituents on these 6-member aromatic ring from alkyl groups having 1–6 carbon atoms, fluoro group, chloro group, hydroxyl group, alkoxyl groups having 1–6 carbon atoms, amino group, alkyl amino groups having 1–6 carbon atoms, and trifluoromethyl group. When two or substituents are present, such substituents may be either identical or different. Furthermore, with regard to ortho positions in the phenyl group or the corresponding positions in the pyridyl group, it is desirable that either one of the two ortho positions is not substituted. In the case where one of the ortho positions is substituted, the substituent should preferably be a small group such as a methyl group, fluoro group, or chloro group.

On the other hand, when a group other than the above-mentioned various types of aromatic group is selected as $R^1$, such a group is preferably selected from alkyl group having 2–7 carbon atoms, cycloalkyl group, and cycloalkyl methyl group. In these groups, $CH_2$ in the carbon chain skeleton of the alkyl group which is not bonded with 2 position of the purine ring may be substituted by S or O, and/or CH in the carbon chain skeleton which is not bonded with the 2 position of the purine ring may be substituted by N, provided that a structure with a bond between hetero-atoms such as a nitrogen-nitrogen bond, for example, due to the above replacement with sulfur, oxygen or nitrogen atoms is excluded. In addition, only one substitution by a sulfur atom, oxygen atom, or nitrogen atom in said alkyl group having 2–7 carbon atoms, cycloalkyl group, or cycloalkyl methyl group is preferable.

Among these alkyl groups, cycloalkyl groups, and cycloalkyl methyl groups, as well as the groups derived from these groups by substitution with a sulfur, oxygen, or nitrogen atom, preferred groups are linear alkyl groups having 2–5 carbon atoms or the groups derived by substitution of one of the $CH_2$ g roups in said linear alkyl group which is not bonded with the purine ring with S or O, or the groups derived by substitution of one of the CH groups which is not bonded with the purine ring with N. Specifically, linear alkyl groups having 2–5 carbon atoms, as well as the corresponding hydroxy alkyl groups, mercaptoalkyl groups, aminoalkyl group, alkyloxyalkyl groups, alkylthioalkyl groups, and N-alkylamino alkyl groups are more preferred groups for $R^1$. Among these, particularly preferred groups are linear alkyl groups having 2–3 carbon atoms and corresponding aminoalkyl groups and N-alkylaminoalkyl groups, such as ethyl group, propyl group, aminomethyl group, 2-aminoethyl group, and methylamino methyl group.

In this connection, preferred groups for $R^1$ among various hydrocarbon groups and the groups derived therefrom are broadly classified into two kinds of groups; one aromatic groups which are typified by phenyl group and the other saturated chain-type groups which are represented by alkyl groups. Although it is not easy to discuss merits or demerits between these two groups, one the aromatic groups typified by phenyl group and the other saturated chain-type groups represented by alkyl groups, the both groups are equally desirable. This is provided that the various groups among each group are in the order of preference mentioned so far.

The desirable selection of $R^1$ and $R^2$ which are the two substituents characterizing the structure of the purine derivatives of the general formula (I) of the present invention used for treating nephritis has been described from the viewpoint of nephritis curative effect. When the substituents $R^1$ and $R^2$ are hydrocarbon groups, the upper limit for the number of carbon atoms are respectively fixed to 17 and 16 in the present invention. The reason is that when a straight chain alkyl group is selected as the group $R^1$ or group $R^2$—$CH_2$—, for example, water solubility of the resulting product is impaired as the number of carbon atoms increases. If the number of carbon atoms exceeds 17, the water solubility decreases to a level which is undesirable in practical use. Specifically, the above mentioned upper limit should be considered in practical use when a highly hydrophobic hydrocarbon group is selected. Also, with regard to the phenyl group including one substituted by hydrocarbon groups, water solubility of the resulting product can be maintained at the allowable level for a pharmaceutical product by limiting the number of carbon atoms under 17 including those of the substituent. In the case of a structure wherein various functional groups are introduced by substitution in hydrocarbon groups, the resulting product may have improved hydrophilicity according to the types of the functional group. Even though this effect is taken into account, the number of atoms which constitute the skeleton of the group should preferably be smaller than the above-mentioned upper limit of 17 or 16.

The group $R^2$ which substitutes on the 2 position of purine ring of the purine derivative of the general formula (I) which is utilized as a medicine for treating nephritis of the present invention is introduced by using a carboxylic acid of the formula $R^1$—COOH or an acid halide or acid anhydride as a raw material compound, and reacting this raw material compound with 4-amino-1-substituted-5-imidazolecarboxamide by an amidation reaction. In this reaction, it is desirable that there should be no unnecessary side reaction from the point of view to maintain a high efficiency of synthesis. Specifically, in the case where there is a group such as —$NH_2$, —NHR, —OH, or —SH which would react with a carboxylic acid halide on the group $R^2$—$CH_2$— of the 4-amino-1-substituted-5-imidazolecarboxamide which is an intermediate material compound, these groups should be appropriately protected. Moreover, when there is a group which participates in the reaction with a carboxylic halide in $R^2$ of the carboxylic acid itself of the formula $R^1$—COOH, such as —$NH_2$, —NHR, —OH, —SH, and the like, such groups should also be protected appropriately in advance.

If there is no group that would react with the carboxylic acid halide such as, for example, —$NH_2$, —NHR, —OH, or —SH in $R^1$, there is no need to introduce and release a protecting group. The use of such a raw material is advantageous in view of operation in the synthetic reaction. For example, a linear alkyl group with 2–5 carbon atoms and corresponding alkyloxy alkyl group, alkylthioalkyl group, and the like have this advantage. Also, in the case where a phenyl group with no substituent or 1 or 2 substituents or a pyridyl group which is one nitrogen substituent thereof, possessing no substituent or 1 or 2 substituents on the ring, is used as $R^1$, the use of the group such as an alkyl group having 1–6 carbon atoms, fluoro group, chloro group, alkoxyl group having 1–6 carbon atoms, or trifluoromethyl group as a substitute on an unsubstituted phenyl group or pyridyl group, or a substituted phenyl group or pyridyl group, may bring about the same operational advantage. Given as specific examples of the group which does not need such protection are ethyl group, propyl group, butyl group, pentyl group, methoxymethyl group, phenyl group, alkyl phenyl group, fluorophenyl group, chlorophenyl group, alkoxyphenyl group, dialkylaminophenyl group, carbamoylphenyl group, N-alkylcarbamoylphenyl group, sulfamoylphenyl group, N-alkylsulfamoylphenyl group, trifluoromethylphenyl group, and pyridyl group.

Among these groups which do not need to be protected, those commercially available carboxylic acids $R_1$—COOH which are used as raw material compounds include those, for example, where $R^1$ is an ethyl group, propyl group, butyl group, pentyl group, methoxymethyl group, phenyl group, methylphenyl group, dimethylphenyl group, fluorophenyl group, chlorophenyl group, methoxyphenyl group, dimethoxyphenyl group, trifluoromethyl phenyl group, and pyridyl group. Particularly, those commercially available carboxylic halide or carboxylic anhydride which can be used in the amidation reaction include those, for example, where $R^1$ is an ethyl group, propyl group, butyl group, pentyl group, phenyl group, fluorophenyl group, chlorophenyl group, and methoxyphenyl group. The use of these groups as $R^1$ provides great advantages not only of a higher effect on treating nephritis, but also a simple synthetic operation.

On the other hand, the substituent $R^2$ is introduced into the intermediate material by an alkylation reaction with 4-benzylideneamino-5-imidazolecarboxamide using an alkylating agent represented by the formula $R^2$—$CH_2$X. When there is a group which participates in the reaction with carboxylic halide, such as —$NH_2$—, —NHR, —OH, or —SH, on the $R^2$—$CH_2$— group, these groups should be appropriately protected as mentioned above in connection with the introduction of $R^1$. The use of $R^2$, which does not have a group which participates in the reaction with a carboxylic acid halide such as, for example, —$NH_2$, —NHR, —OH, or —SH in $R^2$, is advantageous in view of synthetic operation, because there is no need to introduce and release a protecting group.

When a phenyl group, benzyl group, or 2-phenylethyl group with or without a substituent, for example, shown by the general formula (B), is selected as $R^2$, the above operational advantage can be obtained if the groups such as a phenyl group, benzyl group, or 2-phenylethyl groups which does not have a substituent on the benzene ring are selected, or if a substituent on the benzene ring is selected from an alkyl group with 1–6 carbon atoms, fluoro group, chloro group, alkoxyl group with 1–6 carbon atoms, amino group substituted by two alkyl groups having 1–3 carbon atoms, and trifluoromethyl group. Given as specific examples which provide the advantage of reaction operation are phenyl group, alkylphenyl group, fluorophenyl group, chlorophenyl group, alkoxyphenyl group, dialkylaminophenyl group, trifluoromethylphenyl group, benzyl group, and phenylethyl group. Of these, examples of the material for which the alkylating agent or at least an alcohol, ester, or carboxylic acid which becomes the precursor thereof is commercially available include those where $R^2$ is selected from a phenyl group, methylphenyl group, 4-t-butylphenyl group, fluorophenyl group, chlorophenyl group, methoxyphenyl group, 4-ethoxyphenyl group, 4-butoxyphenyl group, dimethylaminophenyl group, trifluoromethylphenyl group, benzyl group, and phenylethyl group. Particularly, for a phenyl group, methylphenyl group, 4-t-butylphenyl group, fluorophenyl group, chlorophenyl group, methoxyphenyl group, trifluoromethylphenyl group, benzyl group, and phenylethyl group alkyl halides are commercially available to be used in the alkylation reaction. The use of these groups as $R^2$ provides great advantages not only of a higher effect on treating nephritis, but also a simple synthetic operation.

The active component in the drug for treating glomerulonephritis of the present invention is preferably administered orally. Particularly, when the drug is used for relaxation or relief of symptom in chronic nephritis, for example, the form of oral administration is ideal. To be compatible with this objective, the pharmaceutical compound to be adopted should not only possess adequate water solubility, but also good absorptivity in digestive tracts.

In general, when a compound forms a hydrogen bond among molecules or in a molecule, the compound tends to become less water soluble. In addition, in the purine derivative of the general formula (I), when the group $R^1$ or $R^2$ is a substituted phenyl group or a group containing a substituted phenyl group, selection of a group which is substituted on the para-position with chloro group, bromo group, hydroxyl group, alkoxyl group having 1 or 2 carbon atoms (methoxy group, ethoxy group), or trifluoromethyl group is not desirable. Because the substitution with such a group on the para-position makes the structure of that part hard to rotate, the compound may be highly crystalline, resulting in a decrease in solubility.

Taking these secondary effects other than the treating effect for nephritis, the following examples can be given to prepare a product which exhibits a high treating effect for nephritis. Generally, the following groups are given as desirable examples of $R^1$ and $R^2$. Desirable examples of $R^1$ include ethyl group, propyl group, aminoethyl group, N-methylaminomethyl group, phenyl group, 2-fluorophenyl group, 3-fluorophenyl group, 4-fluorophenyl group, 3-chlorophenyl group, 3-hydroxyphenyl group, 3-methoxyphenyl group, 3-aminophenyl group, 4-aminophenyl group, 2-pyridyl group, 3-pyridyl group, and 4-pyridyl group; and desirable examples of $R^2$ include phenyl group, 3-methylphenyl group, 4-methylphenyl group, 4-t-butylphenyl group, 2-fluorophenyl group, 3-fluorophenyl group, 4-fluorophenyl group, 3-chlorophenyl group, 3-methoxyphenyl group, benzyl group, and 2-phenylethyl group. Some suitable combinations of $R^1$ and $R^2$ from the groups described above in detail as preferred examples of $R^1$ and $R^2$ to form the purine derivative utilized as a drug for treating glomerulonephritis of the present invention provide more desirable compounds. The compounds obtained by particularly preferred combinations of $R^1$ and $R^2$ are given below in specific compound names.

The first group of compounds produced by combinations of $R^1$ selected from an ethyl group, propyl group, N-methylaminomethyl group, and 2-aminoethyl group, and $R^2$ selected from a phenyl group, phenyl group with one substituent, benzyl group, and 2-phenylethyl group are as follows:
7-benzyl-2-ethylhypoxanthine,
2-ethyl-7-(3-methylbenzyl)hypoxanthine,
2-ethyl-7-(4-methylbenzyl)hypoxanthine,
7-(4-t-butylbenzyl)-2-ethylhypoxanthine,
2-ethyl-7-(2-fluorobenzyl)hypoxanthine,
2-ethyl-7-(3-fluorobenzyl)hypoxanthine,
2-ethyl-7-(4-fluorobenzyl)hypoxanthine,
7-(3-chlorobenzyl)-2-ethylhypoxanthine,
2-ethyl-7-(3-methoxybenzyl)hypoxanthine,
2-ethyl-7-(2-phenylethyl) hypoxanthine,
2-ethyl-7-(3-phenylpropyl) hypoxanthine,
7- benzyl-2-propylhypoxanthine
7-(3-methylbenzyl)-2-propylhypoxanthine,
7-(4-methylbenzyl)-2-propylhypoxanthine,
7-(4-t-butylbenzyl)-2-propylhypoxanthine,
7-(2-fluorobenzyl)-2-propylhypoxanthine,
7-(3-fluorobenzyl)-2-propylhypoxanthine,
7-(4-fluorobenzyl)-2-propyhypoxanthine,
7-(3-chlorobenzyl)-2-propylhypoxanthine,
7-(3-methoxybenzyl)-2-propylhypoxanthine,
7-(2-phenylethyl)-2-propylhypoxanthine,
7-(3-phenylpropyl)-2-propylhypoxanthine,
2-(2-aminoethyl)-7-benzylhypoxanthine,
2-(2-aminoethyl)-7-(3-methylbenzyl)hypoxanthine,
2-(2-aminoethyl)-7-(4-methylbenzyl)hypoxanthine,
2-(2-aminoethyl)-7-(4-t-butylbenzyl)hypoxanthine,
2-(2-aminoethyl)-7-(2-fluorobenzyl)hypoxanthine,
2-(2-aminoethyl)-7-(3-fluorobenzyl)hypoxanthine,
2-(2-aminoethyl)-7-(4-fluorobenzyl)hypoxanthine,
2-(2-aminoethyl)-7-(3-chlorobenzyl)hypoxanthine,
2-(2-aminoethyl)-7-(3-methoxybenzyl)hypoxanthine,
2-(2-aminoethyl)-7-(2-phenylethyl)hypoxanthine,
2-(2-aminoethyl)-7-(3-phenylpropyl)hypoxanthine,
7-benzyl-2-(N-methylaminomethyl) hypoxanthine,
2-(N-methylaminomethyl)-7-(3-methyl benzyl) hypoxanthine,
2-(N-methylaminomethyl)-7-(4-methylbenzyl) hypoxanthine,
7-(4-t-butylbenzyl)-2-(N-methylaminomethyl) hypoxanthine,
7-(2-fluorobenzyl)-2-(N-methylaminomethyl) hypoxanthine,
7-(3-fluorobenzyl)-2-(N-methylaminomethyl) hypoxanthine,
7-(4-fluorobenzyl)-2-(N-methylaminomethyl) hypoxanthine,
7-(3-chlorobenzyl)-2-(N-methylaminomethyl) hypoxanthine,
7-(3-methoxybenzyl)-2-(N-methylaminomethyl) hypoxanthine,
2-(N-methylaminomethyl)-7-(2-phenylethyl)hypoxanthine, and
2-(N-methylaminomethyl)-7-(3-phenylpropyl) hypoxanthine.

The second group of compounds produced by combinations of $R^1$ selected from phenyl groups with no substituent or one substituent, and $R^2$ selected from phenyl groups, phenyl group with one substituent, benzyl group, and 2-phenylethyl group are as follows:
7-benzyl-2-phenylhypoxanthine,
7-(3-methylbenzyl)-2-phenylhypoxanthine,
7-(4-methylbenzyl)-2-phenylhypoxanthine,
7-(4-t-butylbenzyl)-2-phenylhypoxanthine,
7-(2-fluorobenzyl)-2-phenylhypoxanthine,
7-(3-fluorobenzyl)-2-phenylhypoxanthine,
7-(4-fluorobenzyl)-2-phenylhypoxanthine,
7-(3-chlorobenzyl)-2-phenylhypoxanthine,
7-(3-methoxybenzyl)-2-phenylhypoxanthine,
7-(2-phenylethyl)-2-phenylhypoxanthine,
7-(3-phenylpropyl)-2-phenylhypoxanthine,
7-benzyl-2-(2-fluorophenyl)hypoxanthine,
2-(2-fluorophenyl)-7-(3-methylbenzyl)hypoxanthine,
2-(2-fluorophenyl)-7-(4-methylbenzyl)hypoxanthine,
7-(4-t-butylbenzyl)-2-(2-fluorophenyl) hypoxanthine,
7-(2-fluorobenzyl)-2-(2-fluorophenyl)hypoxanthine,
7-(3-fluorobenzyl)-2-(2-fluorophenyl)hypoxanthine,
7-(4-fluorobenzyl)-2-(2-fluorophenyl)hypoxanthine,
7-(3-chlorobenzyl)-2-(2-fluorophenyl)hypoxanthine,
2-(2-fluorophenyl)-7-(3-methoxybenzyl)hypoxanthine,
2-(2-fluorophenyl)-7-(2-phenylethyl) hypoxanthine,
2-(2-fluorophenyl)-7-(3-phenylpropyl)hypoxanthine,
7-benzyl-2-(3-fluorophenyl)hypoxanthine,
2-(3-fluorophenyl)-7-(3-methylbenzyl)hypoxanthine,
2-(3-fluorophenyl)-7-(4-methylbenzyl)hypoxanthine,
7-(4-t-butylbenzyl)-2-(3-fluorophenyl)hypoxanthine,
7-(2-fluorobenzyl)-2-(3-fluorophenyl)hypoxanthine,
7-(3-fluorobenzyl)-2-(3-fluorophenyl)hypoxanthine,
7-(4-fluorobenzyl)-2-(3-fluorophenyl)hypoxanthine,
7-(3-chlorobenzyl)-2-(3-fluorophenyl)hypoxanthine,
2-(3-fluorophenyl)-7-(3-methoxybenzyl)hypoxanthine,
2-(3-fluorophenyl)-7-(2-phenylethyl)hypoxanthine,
2-(3-fluorophenyl)-7-(3-phenylpropyl)hypoxanthine,
7-benzyl-2-(4-fluorophenyl)hypoxanthine,
2-(4-fluorophenyl)-7-(3-methylbenzyl)hypoxanthine,
2-(4-fluorophenyl)-7-(4-methylbenzyl)hypoxanthine,
7-(4-t-butylbenzyl)-2-(4-fluorophenyl)hypoxanthine,
7-(2-fluorobenzyl)-2-(4-fluorophenyl)hypoxanthine,
7-(3-fluorobenzyl)-2-(4-fluorophenyl)hypoxanthine,
7-(4-fluorobenzyl)-2-(4-fluorophenyl)hypoxanthine,
7-(3-chlorobenzyl)-2-(4-fluorophenyl)hypoxanthine,
2-(4-fluorophenyl)-7-(3-methoxybenzyl)hypoxanthine,
2-(4-fluorophenyl)-7-(2-phenylethyl)hypoxanthine
2-(4-fluorophenyl)-7-(3-phenylpropyl)hypoxanthine,
7-benzyl-2-(3-chlorophenyl)hypoxanthine,
2-(3-chlorophenyl)-7-(3-methylbenzyl)hypoxanthine,
2-(3-chlorophenyl)-7-(4-methylbenzyl)hypoxanthine,
7-(4-t-butylbenzyl)-2-(3-chlorophenyl)hypoxanthine,
2-(3-chlorophenyl)-7-(2-fluorobenzyl)hypoxanthine,
2-(3-chlorophenyl)-7-(3-fluorobenzyl)hypoxanthine, 2-(3-chlorophenyl)-7-(4-fluorobenzyl)hypoxanthine,
7-(3-chlorobenzyl)-2-(3-chlorophenyl)hypoxanthine,
2-(3-chlorophenyl)-7-(3-methoxybenzyl)hypoxanthine,
2-(3-chlorophenyl)-7-(2-phenylethyl)hypoxanthine,
2-(3-chlorophenyl)-7-(3-phenylpropyl)hypoxanthine,
7-benzyl-2-(3-hydroxyphenyl)hypoxanthine,
2-(3-hydroxyphenyl)-7-(3-methylbenzyl)hypoxanthine,
2-(3-hydroxyphenyl)-7-(4-methylbenzyl)hypoxanthine,
7-(4-t-butylbenzyl)-2-(3-hydroxyphenyl)hypoxanthine,
7-(2-fluorobenzyl)-2-(3-hydroxyphenyl)hypoxanthine,
7-(3-fluorobenzyl)-2-(3-hydroxyphenyl)hypoxanthine,
7-(4-fluorobenzyl)-2-(3-hydroxyphenyl)hypoxanthine,
7-(3-chlorobenzyl)-2-(3-hydroxyphenyl)hypoxanthine,
2-(3-hydroxyphenyl)-7-(3-methoxybenzyl)hypoxanthine,
2-(3-hydroxyphenyl)-7-(2-phenylethyl)hypoxanthine,
2-(3-hydroxyphenyl)-7-(3-phenylpropyl)hypoxanthine,
7-benzyl-2-(3-methoxyphenyl)hypoxanthine,
2-(3-methoxyphenyl)-7-(3-methylbenzyl)hypoxanthine,
2-(3-methoxyphenyl)-7-(4-methylbenzyl)hypoxanthine,
7-(4-t-butylbenzyl)-2-(3-methoxyphenyl)hypoxanthine,
7-(2-fluorobenzyl)-2-(3-methoxyphenyl)hypoxanthine,
7-(3-fluorobenzyl)-2-(3-methoxyphenyl)hypoxanthine,
7-(4-fluorobenzyl)-2-(3-methoxyphenyl)hypoxanthine,
7-(3-chlorobenzyl)-2-(3-methoxyphenyl)hypoxanthine,
7-(3-methoxybenzyl)-2-(3-methoxyphenyl)hypoxanthine,
2-(3-methoxyphenyl)-7-(2-phenylethyl)hypoxanthine,
2-(3-methoxyphenyl)-7-(3-phenylpropyl)hypoxanthine,
2-(3-aminophenyl)-7-benzylhypoxanthine,
2-(3-aminophenyl)-7-(3-methylbenzyl)hypoxanthine,
2-(3-aminophenyl)-7-(4-methylbenzyl)hypoxanthine,
2-(3-aminophenyl)-7-(4-t-butylbenzyl)hypoxanthine,
2-(3-aminophenyl)-7-(2-fluorobenzyl) hypoxanthine,
2-(3-aminophenyl)-7-(3-fluorobenzyl)hypoxanthine,
2-(3-aminophenyl)-7-(4-fluorobenzyl) hypoxanthine,
2-(3-aminophenyl)-7-(3-chlorobenzyl)hypoxanthine,
2-(3-aminophenyl)-7-(3-methoxybenzyl)hypoxanthine,
2-(3-aminophenyl)-7-(2-phenylethyl)hypoxanthine,
2-(3-aminophenyl)-7-(3-phenylpropyl)hypoxanthine,
2-(4-aminophenyl)-7-benzylhypoxanthine,
2-(4-aminophenyl)-7-(3-methylbenzyl)hypoxanthine,
2-(4-aminophenyl)-7-(4-methylbenzyl)hypoxanthine,
2-(4-aminophenyl)-7-(4-t-butylbenzyl)hypoxanthine,
2-(4-aminophenyl)-7-(4-t-butylbenzyl)hypoxanthine, and
2-(4-aminophenyl)-7-(3-phenylpropyl)hypoxanthine.

The third group of compounds produced by combinations of pyridyl group as $R^1$ and $R^2$ selected from phenyl group, phenyl group with one substituent, benzyl group, and 2-phenylethyl group are as follows:
7-benzyl-2-(2-pyridyl)hypoxanthine,
7-(3-methylbenzyl)-2-(2-pyridyl)hypoxanthine,
7-(4-methylbenzyl)-2-(2-pyridyl)hypoxanthine,
7-(4-t-butylbenzyl)-2-(2-pyridyl)hypoxanthine,
7-(2-fluorobenzyl)-2-(2-pyridyl)hypoxanthine,
7-(3-fluorobenzyl)-2-(2-pyridyl)hypoxanthine,
7-(4-fluorobenzyl)-2-(2-pyridyl)hypoxanthine,
7-(3-chlorobenzyl)-2-(2-pyridyl)hypoxanthine,
7-(3-methoxybenzyl)-2-(2-pyridyl)hypoxanthine,
7-(2-phenylethyl)-2-(2-pyridyl)hypoxanthine,
7-(3-phenylpropyl)-2-(2-pyridyl)hypoxanthine,
7-benzyl-2-(3-pyridyl)hypoxanthine,
7-(3-methylbenzyl)-2-(3-pyridyl)hypoxanthine,
7-(4-methylbenzyl)-2-(3-pyridyl)hypoxanthine,
7-(4-t-butylbenzyl)-2-(3-pyridyl)hypoxanthine,
7-(2-fluorobenzyl)-2-(3-pyridyl)hypoxanthine,
7-(3-fluorobenzyl)-2-(3-pyridyl)hypoxanthine,
7-(4-fluorobenzyl)-2-(3-pyridyl)hypoxanthine,
7-(3-chlorobenzyl)-2-(3-pyridyl)hypoxanthine,
7-(3-methoxybenzyl)-2-(3-pyridyl)hypoxanthine,
7-(2-phenylethyl)-2-(3-pyridyl)hypoxanthine,
7-(3-phenylpropyl)-2-(3-pyridyl)hypoxanthine,
7-benzyl-2-(4-pyridyl) hypoxanthine,
7-(3-methylbenzyl)-2-(4-pyridyl)hypoxanthine,
7-(4-methylbenzyl)-2-(4-pyridyl)hypoxanthine,
7-(4-t-butylbenzyl)-2-(4-pyridyl)hypoxanthine,
7-(2-fluorobenzyl)-2-(4-pyridyl)hypoxanthine,
7-(3-fluorobenzyl)-2-(4-pyridyl)hypoxanthine,
7-(4-fluorobenzyl)-2-(4-pyridyl)hypoxanthine,
7-(3-chorobenzyl)-2-(4-pyridyl)hypoxanthine,
7-(3-methoxybenzyl)-2-(4-pyridyl)hypoxanthine,
7-(2-phenylethyl)-2-(4-pyridyl)hypoxanthine, and
7-(3-phenylpropyl)-2-(4-pyridyl)hypoxanthine.

A pharmaceutical composition which contains the above-mentioned novel purine derivatives or their pharmaceutically acceptable salts as an active component can be used in various dosage forms, for example, orally administered agents such as tablets, capsules, powder, or in the form of injections. An orally administered agent is in conformity of the objective for the drug for treating nephritis of the present invention. For instance, the purine derivative of the present invention is prepared into tablets by mixing with vehicles such as lactose and starch, lubricants such as magnesium stearate and talc, and other additives commonly used with pharmaceuticals. Although the dose of the purine derivative contained in the drug for treating glomerulonephritis of the present invention can be appropriately determined according to the sex, age, and body weight of the subject, objective of administration, the degree of pathology of the patient, and the like, a typical dose for male adult is in the range of 0.01–100 mg/kg per day, which may be administered either one time or several times a day.

THE REST MODE FOR CARRYING OUT THE INVENTION

The novel purine derivatives of the present invention and the process for preparing the same will be specifically described by way of examples. In addition, a superior effect of the novel purine derivatives of the present invention to suppress and cure inflammation which is a peculiar symptom of glomerulonephritis will be shown by test examples.

Reference Example 1

Preparation of 4-benzylideneamino-5-imidazole carboxamide (an intermediate material)

16.3 g (100 mmol) of 4-amino-5-imidazolecarboxamide hydrochloride was suspended in 200 ml ethanol, and 27.8 ml (200 mmol) of triethylamine was added to the suspension and dissolved. To the solution, 10.2 ml (100 mmol) of benzaldehyde was added and the mixture was heated for 8 hours while refluxing. After the addition of 400 ml of distilled water, the reaction mixture was stirred for one hour at 0° C. A solid precipitate produced was collected by filtration, washed with distilled water, then with ethanol, and dried under reduced pressure to obtain 20.8 g of the title compound (yield 97%).

Reference Example 2

4-Amino-1-benzyl-5-imidazole carboxamide 12.8 g (60 mmol) of 4-benzylideneamino-5-imidazole carboxamide which is an intermediate material obtained in the Reference Example 1 was suspended in a mixed solvent of 240 ml dimethylformamide and 30 ml distilled water, and 16.6 g (120 mmol) of potassium carbonate was added to the suspension. 13.8 ml of benzyl chloride was added dropwise to the solution over 45 minutes at 80° C. After the addition, the mixture was stirred for one hour. The solvent was evaporated under vacuum, the residue was dissolved in chloroform, and the chloroform layer was washed with distilled water. Crude crystals obtained after evaporation of solvent was recrystallized from ethanol to obtain 14.4 g of 4-benzylideneamino-1-benzyl-5-imidazole carboxamide (yield 79%).

9.12 g (30 mol) of 4-benzylideneamino-1-benzyl-5-imidazolecarboxamide obtained was dissolved in 135 ml of tetrahydrofuran. After the addition of 15 ml of concentrated hydrochloric acid, the mixture was stirred at room temperature for two hours. The precipitate obtained was separated by filtration and washed with tetrahydrofuran to obtain 7.26 g of 4-amino-1-benzyl-5-imidazolecarboxamide hydrochloride. 7.26 g of the 4-amino-1-benzyl-5-imidazole carboxamide hydrochloride obtained was dissolved in a mixed solvent of 100 ml of methyl alcohol and 80 ml of distilled water. After the addition of 7.5 ml of 4 N aqueous solution of sodium hydroxide, the mixture was stirred at room temperature for one hour. Methanol was evaporated and the resulting precipitate separated by filtration was washed with distilled water and ethanol to obtain 5.85 g of the title compound (yield 90%) (2 steps).

EXAMPLE 1

7-Benzyl-2-phenylhypoxanthine 4.32 g (20 mmol) of 4-amino-1-benzyl-5-imidazole carboxamide obtained in the Reference Example 2 was suspended in 50 ml of dry toluene and the mixture was stirred for four hours at room temperature. The solid product was separated by filtration, washed with toluene, hexane, and water in this order, and dried under reduced pressure to obtain 5.70 g of 4-benzoylamino-1-benzyl-5-imidazolecarboxamide.

5.70 g (17.8 mmol) of the amide compound was suspended in 35 ml of ethanol and 1.25 g (19 mmol) of potassium hydroxide was added to the mixture. The mixture was stirred at 80° C. for 3 hours, followed by the addition of 2.6 ml of acetic acid to make the mixture weakly acidic. After stirring for a while, the solid product was separated by filtration, washed with ethanol, and dried under reduced pressure to 4.80 g of 7-benzyl-2-phenylhypoxanthine (yield: 80%, 2 steps).

$^1$H-NMR (300 MHz, DMSO-$d_6$, δ ppm):

5.61 (2H, s, methylene of benzyl group), 7.30–7.41 (5H, m, Ph of benzyl group), 7.50–7.55 (3H, m, 3, 4, and 5 positions of phenyl group), 8.07–8.10 (2H, m, 2 and 6 positions of phenyl group), 8.44 (1H, s, 8 position of purine skeleton), 12.52 (1H, s, NH)

MS (EI): 302 [M$^+$], 91

IR (cm$^{-1}$): 3400, 1680 (C=O), 1560, 1380

HPLC: Purity 97.7%, Retention time: 17.08 min.

(HPLC conditions)

Column: ODS column (ø4.6 mm×150 mm)

Solvent: 0.1% TFA-containing distilled water/acetonitrile

Acetonitrile, 0–100% 30 minute linear gradient

Flow rate: 1 ml/min.

Detection: 254 nm absorption Purity conversion: % of peak area

EXAMPLE 2

7-Benzyl-2-(3,4-dimethoxyphenyl)hypoxanthine

An amidation reaction was carried out in the same manner as in Example 1 using 2.2 g (10 mmol) of 4-amino-1-benzyl-5-imidazolecarboxamide obtained in the Reference Example 2 and, instead of benzoyl chloride, using 3,4-dimethoxybenzoyl chloride which was separately prepared according to a conventional method. Crude crystals obtained after a post-treatment was recrystallized from hot methanol, to obtain 3.2 g of 1-benzyl-4-(3,4-dimethoxybenzoylamino)-5-imidazole carboxamide.

3.0 g (7.9 mmol) of the amide compound obtained was subjected to a cyclization reaction for 18 hours under the same conditions as in Example 1. The crude crystals obtained after a post-treatment was purified by suspension in hot methanol to obtain 2.17 g of 7-benzyl-2-(3,4-dimethoxyphenyl) hypoxanthine. Yield 64% (2 steps)

$^1$H-NMR (300 MHz, DMSO-$d_6$, δ ppm):

3.82 (3H, s, methoxy group), 3.86 (3H, s, methoxy group), 5.58 (2H, s, methylene of benzyl group), 7.08 (1H, d, J=8.1 Hz, 5 position of dimethoxyphenyl group), 7.30–7.36 (5H, m, Ph of benzyl group), 7.70–7.75 (2H, m, 2 and 6 positions of dimethoxyphenyl group), 8.39 (1H, s, 8 position of purine skeleton), 12.36 (1H, brz s, NH)

TOF-MS: 363 for $C_{20}H_{19}N_4O_3$ (M+H)

HPLC: Purity 99%, Retention time 17.52 min. (the same conditions as in Example 1)

EXAMPLE 3

7-Benzyl-2-(3,4-dihydroxyphenyl)hypoxanthine 0.92 g of 7-benzyl-2-(3,4-dimethoxyphenyl) hypoxanthine obtained in Example 2 was dissolved in 18 ml of acetic acid and 3 ml of 48% aqueous solution of hydrogen bromide, and the resulting solution was stirred for 16 hours at 120° C. After removing acetic acid by evaporation under vacuum, water was added and the mixture was stirred for a while. The solid precipitate produced was separated by filtration, washed with water, and dried under reduced pressure. The crude product was purified by silica gel column chromatography and dried under reduced pressure to obtain 0.85 g of 7-benzyl-2-(3,4-dihydroxyphenyl) hypoxanthine (yield 53%).

$^1$H-NMR (300 MHz, DMSO-$d_6$, δ ppm):

5.58 (s, 2H, methylene of benzyl group), 6.82 (d, J=8 Hz, 1H, 5 position of dihydroxyphenyl group), 7.29–7.56 (m, 7H, Ph of benzyl group, 2 and 6 positions of dihydroxyphenyl group), 8.40 (s, 1H, 8 position of purine skeleton), 9.28 (bs, 1H, OH), 9.58 (bs, 1H, OH), 12.16 (bs, 1H, OH or NH)

MS (EI): 334[M$^+$], 91

IR (cm$^{-1}$): 3400, 1680 (C=O), 1500, 1440, 1380, 1300

HPLC: Purity 98.0%, Retention time: 14.68 min. (the same conditions as in Example 1)

EXAMPLE 4

7-Benzyl-2-(3,5-di-t-butyl-4-hydroxyphenyl) hypoxanthine

An amidation reaction was performed following the same conditions as in Example 1 using 2.2 g (10 mmol) of 4-amino-1-benzyl-5-imidazole carboxamide obtained in Reference Example 2 and using, instead of benzoyl chloride, 3,5-di-t-butyl-4-methoxymethoxybenzoyl chloride which was separately prepared by a conventional method. After a post-treatment, a crude amide product was obtained. The crude amide was subjected to a cyclization reaction for 12 hours according to the same conditions as in Example 1. 2.17 g of 7-benzyl-2-(3,5-di-t-butyl-4-methoxymethoxyphenyl)hypoxanthine was obtained after a post-treatment. Yield 45% (2 steps).

1.90 g (4 mmol) of the hypoxanthine derivative obtained was dissolved in 80 ml of chloroform, 10.0 ml of concentrated hydrochloric acid was added, and the mixture was stirred at room temperature for 8 hours. After neutralization with saturated aqueous solution of sodium hydrogencarbonate, the chloroform layer was separated and the solvent was evaporated. The resulting solid was washed with a mixed solvent of ethanol and water and dried under reduced pressure to obtain 1.51 g of 7-benzyl-2-(3-5-di-t-butyl-4-hydroxyphenyl)hypoxanthine(yield 88%).

$^1$H-NMR (270 MHz, DMSO-$d_6$, δ ppm):

1.44 (18H, s, t-butyls), 5.59 (2H, s, methylene of benzyl group), 7.28–7.50(5H, m, Ph of benzyl group), 7.79 (2H, s, 2 and 6 positions of 3,5-di-t-butyl-4-hydroxyphenyl group), 8.39 (1H, s, 8 position of purine skeleton), 12.47 (1H, br. s, NH)

MS (EI): 430[M$^+$], 415, 91

HPLC: Purity 99.4%, Retention time: 23.23 min. (the same conditions as in Example 1)

EXAMPLE 5

7-Benzyl-2-(4-methoxybenzyl)hypoxanthine

An amidation reaction was carried out under the same conditions as in Example 1 using 6.48 g (30 mmol) of 4-amino-1-benzyl-5-imidazole carboxamide obtained in Reference Example 2 and using, instead of benzoyl chloride, 4-methoxyphenylacetyl chloride which was separately prepared according to a conventional method. A crude amide product was obtained after the post-treatment. The crude amide was subjected to a cyclization reaction for 13 hours under the same conditions as in Example 1. 1.92 g of 7-benzyl-2-(4-methoxybenzyl)hypoxanthine was obtained after the post-treatment. Yield 18% (2 steps).

$^1$H-NMR (300 MHz, DMSO-$d_6$, δ ppm):

3.70 (3H, s, OCH$_3$), 3.83 (2H, s, methylene of benzyl group of 4-methoxy benzyl group), 5.51 (2H, s, methylene of benzyl group), 6. 86 (2H, d, J=9 Hz, 3 and 5 positions of 4-methoxybenzyl group), 7.25 (2H, d, J=9 Hz, 2 and 6 positions of 4-methoxybenzyl group), 7.3 (5H, m, Ph of benzyl group), 8.32 (1H, s, 8 position purine skeleton), 12.34 (1H, s, NH)

MS(EI): 346 [M$^+$], 91

HPLC: Purity 98.7%, Retention time: 17.92 min. (the same conditions as in Example 1)

EXAMPLE 6

7-Butyl-2-(3, 5-dimethyl-4-hydroxyphenyl hypoxanthine

Following the same conditions as in Reference Example 2, 14.30 g (67 mmol) of 4-benzylideneamino-5-imidazole carboxamide obtained in Reference Example 1 was reacted with butyl iodate, instead of benzyl chloride in the Reference Example 2. After the post-treatment, 2.47 g of 4-amino-1-butyl-5-imidazolecarboxamide hydrochloride was obtained (yield 17%).

1.53 g (7 mmol) of 4-amino-1-butyl-5-imidazole carboxamide hydrochloride thus obtained was subjected to an amidation reaction following the conditions of Example 1 using, instead of benzoyl chloride of Example 1, 4-benzyloxy-3,5-dimethylbenzoyl chloride which was separately prepared according to a conventional method. 1.01 g of 4-(4-benzyloxy-3,5-dimethylbenzoylamino)-1-butyl-5-imidazolecarboxamide was obtained after the post-treatment.

The amide thus obtained was subjected to a cyclization reaction for 10 hours following the conditions of Example 1. After the post-treatment, 0.89 g of 2-(4-benzyloxy-3,5-dimethylphenyl)-7-butylhypoxanthine was obtained.

Then, the resulting hypoxanthine derivative was suspended in 50 ml ethanol and 0.5 g of 5% Pd/C was added. The internal atmosphere of the reaction system was replaced with hydrogen, followed by stirring for 10 hours at 70° C. After cooling, the resulting solid precipitate was dissolved in chloroform and the Pd/C was separated by filtration. The filtrate was concentrated under vacuum to obtain 0.56 g of 7-butyl-2-(3,5-dimethyl-4-hydroxyphenyl)hypoxanthine. Yield 26% (3 steps).

$^1$H-NMR (300 MHz, DMSO-$d_6$, δ ppm):

0.89 (3H, t, J=7.4 Hz, terminus methyl of butyl group), 1.24 (2H, m, 3 position CH$_2$ of butyl group), 1.80 (2H, m, 2 position CH$_2$ of butyl group), 2.23 (6H, s, methyls of 3,5-dimethyl-4-hydroxyphenyl group), 4.31 (2H, t, J=7.5 Hz, N-binding methylene of butyl group), 7.75 (2H, s, 2 and 6 positions of 3,5-dimethyl-4-hydroxyphenyl group), 8.19 (1H, s, 8 position of purine skeleton), 8.9 (1H, br. s, OH), 12.0 (1H, br. s, NH)

MS (EI): 312 [M$^+$], 256

HPLC: Purity 98.6%, Retention time: 16.38 min. (the same conditions as in Example 1)

EXAMPLE 7

7-Benzyl-2-(3-pyridyl)hypoxanthine 1.08 g (4.99 mmol) of 4-amino-1-benzyl-5-imidazole carboxamide prepared in Reference Example 2, 0.73 g (5.93 mmol) of nicotinic acid, 0.92 g (6.81 mmol) of 1-hydroxybenzotriazole, 0.60 g (5.93 mmol) of triethylamine were dissolved in 30 ml. of dimethylformamide, and 1.15 g (6.00 mmol) of 1-(3-dimethylaminopropyl)-3-ethylcarbodiimide hydrochloride was added, followed by stirring at room temperature for three days. After evaporation of the solvent, a solid precipitate produced by the addition of a 5% aqueous solution of sodium hydrogencarbonate was collected by filtration, was washed with distilled water, and dried under reduced pressure to obtain 1.08 g of crude amide.

1.08 g of the crude amide thus produced was subjected to a cyclization reaction for 9 hours under the same conditions as in Example 1. After post-treatment, 0.31 g of 7-benzyl-2-(3-pyridyl)hypoxanthine was obtained (yield 20%, 2 steps).

$^1$H-NMR (300 MHz, DMSO-d$_6$, δ ppm):

5.61 (2H, s, methylene of benzyl group), 7.27–7.38 (5H, m, aromatic of benzyl group), 7.55 (1H, dd, J=7.8 Hz, 4.8 Hz, 1H, s, 5 position of pyridyl group), 8.39 (1H, d, J=8.4 Hz, 6 position of pyrodyl group), 8.45 (1H, s, 8 position of purine skeleton), 8.71 (1H, d, J=5.1 Hz, 4 position of pyridyl group), 9.18 (1H, s, 2 position of pyridyl group), 12.71 (1H, br. s, NH)

MS (DI-EI): 303 for C$_{17}$H$_{13}$N$_5$O (M)

HPLC: Purity 99.3%, Retention time: 13.46 min. (the same conditions as in Example 1)

EXAMPLE 8

7-Benzyl-2-(3,5-dimethyl-4-hydroxyphenyl) hypoxanthine

An amidation reaction and post-treatment were carried out according to the conditions of Example 1, using 1.06 g (4.9 mmol) 4-amino-1-benzyl-5-imidazolecarboxamide prepared in Reference Example 2 and, instead of benzoyl chloride, 3,5-dimethyl-4-methoxymethoxybenzoyl chloride which was separately prepared by a conventional method, to obtain 1.40 g of 1-benzyl-4-(3,5-dimethyl-4-methoxymethoxybenzoyl-amino)-5-imidazolecarboxamide.

A cyclization reaction was carried out for 12 hours under the same conditions as in Example 1 using the resulting crude amide. The resulting product was post-treated to obtain 1.14 g of 7-benzyl-2-(3,5-dimethyl-4-methoxymethoxyphenyl)hypoxanthine.

A de-protection reaction of methoxymethyl group and a post-treatment of the resulting hypoxanthine derivative were carried out under the same conditions as in Example 4 to produce 0.99 g of 7-benzyl-2-(3,5-dimethyl-4-hydroxyphenyl)-hypoxanthine. Yield 48% (3 steps).

9.18 (1H, s, 2 position of pyridyl group), 12.71 (1H, br. s, NH)

MS (DI-EI): 303 for C$_{17}$H$_{13}$N$_5$O (M)

HPLC: Purity 99.3%, Retention time: 13.46 min. (the same conditions as in Example 1)

EXAMPLE 8

7-Benzyl-2-(3,5-dimethyl-4-hydroxyphenyl hypoxanthine

An amidation reaction and post-treatment were carried out according to the conditions of Example 1, using 1.06 g (4.9 mmol) 4-amino-1-benzyl-5-imidazolecarboxamide prepared in Reference Example 2 and, instead of benzoyl chloride, 3,5-dimethyl-4-methoxymethoxybenzoyl chloride which was separately prepared by a conventional method, to obtain 1.40 g of 1-benzyl-4-(3,5-dimethyl-4-methoxymethoxybenzoyl-amino)-5-imidazolecarboxamide.

A cyclization reaction was carried out for 12 hours under the same conditions as in Example 1 using the resulting crude amide. The resulting product was post-treated to obtain 1.14 g of 7-benzyl-2-(3,5-dimethyl-4-methoxymethoxyphenyl)hypoxanthine.

A de-protection reaction of methoxymethyl group and a post-treatment of the resulting hypoxanthine derivative were carried out under the same conditions as in Example 4 to produce 0.99 g of 7-benzyl-2-(3,5-dimethyl-4-hydroxyphenyl)-hypoxanthine. Yield 48% (3 steps).

$^1$H-NMR (300 MHz, DMSO-d$_6$, δ ppm), 2.23 (6H, s, methyls of 3,5-dimethyl-4-hydroxyphenyl group), 5.56 (2H, s, methylene of benzyl group), 7.28–7.37 (5H, m, aromatic of benzyl group), 7.74 (2H, s, 2 and 6 positions of 3,5-dimethyl-4-hydroxyphenyl group), 8.36 (1H, s, 8 position of purine skeleton), 8.86 (1H, s, OH), 12.10 (1H, s, NH)

MS (EI): 346 [M$^+$], 91

HPLC: Purity 99.1%, Retention time 17.35 min. (the same conditions as in Example 1)

EXAMPLE 9

7-Benzyl-2-(3.5-di-t-butylphenyl hypoxanthine

An amidation reaction and post-treatment were carried out according to the conditions of Example 1, using 4.15 g (19.2 mmol) of 4-amino-1-benzyl-5-imidazolecarboxamide prepared in Reference Example 2 and, instead of benzoyl chloride, 3,5-di-t-butylbenzoyl chloride which was separately prepared by a conventional method, to obtain a crude amide product.

A cyclization reaction was carried out for 8.5 hours under the same conditions as in Example 1 using the resulting crude amide. The resulting product was post-treated to obtain 6.72 g of 7-benzyl-2-(3,5-di-butylphenyl) hypoxanthine. Yield 97% (2 steps).

$^1$H-NMR (270 MHz, DMSO-d$_6$, δ ppm), 1.37 (18H, s, methyls of t-butyl group), 2.65 (1H, br, s, NH), 5.63 (2H, s, methylene of benzyl group), 7.30–7.36 (5H, m, aromatic of benzyl group), 7.55 (1H, d, J=1.8 Hz, 4 position of di-t-butylphenyl group), 7.87 (1H, s, 8 position of purine skeleton), 7.95 (2H, d, J=1.8 Hz, 2 and 6 positions of di-t-butylphenyl group)

TOF-MS: 415 for C$_{26}$H$_{31}$N$_4$O (M+H)

HPLC: Purity: 99.2%, Retention time: 26.3 min. (the same conditions as in Example 1)

EXAMPLE 10

7-Benzyl-2-(3,5-dimethylphenyl hypoxanthine

An amidation reaction and post-treatment were carried out according to the conditions of Example 1, using 6.54 g (30.2 mmol) of 4-amino-1-benzyl-5-imidazolecarboxamide prepared in Reference Example 2 and, instead of benzoyl chloride, 3,5-dimethylbenzoyl chloride which was separately prepared by a conventional method, to obtain 9.62 g of 1-benzyl-4-(3,5-dimethylbenzoylamino)-5-imidazolecarboxamide (yield 91%).

A cyclization reaction was carried out for 8.5 hours under the same conditions as in Example 1 using 9.62 g (27.6 mmol) of the resulting amide. The resulting product was post-treated to obtain 8.73 g of 7-benzyl-2-(3,5-dimethylphenyl)hypoxanthine (yield 91%).

$^1$H-NMR (270 MHz, DMSO-d$_6$, δ ppm), 2.36 (6H, s, methyls), 5.62 (2H, s, methylene of benzyl group), 7.13 (1H, s, 4 position of dimethylphenyl group), 7.24–7.44 (5H, m, aromatic of benzyl group), 7.75 (2H, s, 2 and 6 positions of dimethylphenyl group), 8.29 (1H, S, 8 position of purine skeleton)

12.30 (1H, br. s, NH)

TOF-MS: 331 for $C_{20}H_{19}N_4O$ (M+H)

HPLC: Purity: 98.2%, Retention time: 20.1 min. (the same conditions as in Example 1)

EXAMPLE 11

7-Benzyl-2-(4-ethoxyphenyl)hypoxanthine

An amidation reaction and post-treatment were carried out according to the conditions of Example 1, using 2.35 g (10.9 mmol) of 4-amino-1-benzyl-5-imidazolecarboxamide prepared in Reference Example 2 and, instead of benzoyl chloride, 4-ethoxybenzoyl chloride which was separately prepared by a conventional method, to obtain a crude amide product.

A cyclization reaction was carried out for 8.5 hours under the same conditions as in Example 1 using the resulting crude amide. The resulting product was post-treated to obtain 2.99 g of 7-benzyl-2-(4-ethoxyphenyl)hypoxanthine. Yield 80% (2 steps).

$^1$H-NMR (270 MHz, DMSO-d$_6$, δ ppm), 1.35 (3H, t, J=6.9 Hz, methyl of ethoxy group), 4.11 (2H, t, J=6.9 Hz, methylene of ethoxy group)

5.58 (2H, s, methylene of benzyl group)

7.04 (2H, d, J=8.9 Hz, 3 and 5 positions of ethoxyphenyl group)

7.37 (5H, m, aromatic of benzyl group), 8.06 (2H, d, J=9.2 Hz, 2 and 6 positions of ethoxyphenyl group), 8.40 (1H, s, 8 position of purine skeleton)

12.34 (1H, br. s, NH)

TOF-MS: 347 for $C_{20}H_{19}N_4O_2$ (M+H)

HPLC: Purity: 99.0%, Retention time: 18.96 min. (the same conditions as in Example 1)

EXAMPLE 12

7-Benzyl-2-(4-butoxyphenyl)hypoxanthine

An amidation reaction and post-treatment were carried out according to the conditions of Example 1, using 2.01 g (9.30 mmol) of 4-amino-1-benzyl-5-imidazolecarboxamide prepared in Reference Example 2 and, instead of benzoyl chloride, 4-butoxybenzoyl chlorides which was separately prepared by a conventional method, to obtain a crude amide product.

A cyclization reaction was carried out for 8.5 hours under the same conditions as in Example 1 using the resulting crude amide. The resulting product was post-treated to obtain 3.00 g of 7-benzyl-2-(4-butoxyphenyl)hypoxanthine. Yield 86% (2 steps).

$^1$H-NMR (270 MHz, DMSO-d$_6$, δ ppm):

0.87 (3H, t, J=7.3 Hz, methyl of butoxy group), 1.38 (2H, m, methylene of butoxy group), 1.65 (2H, m, methylene of butoxy group), 3.97 (2H, t, J=6.5 Hz, O-bonded methylene of butoxy group), 5.51 (2H, s, methylene of benzyl group), 6.95 (2H, d, J=8.6 Hz, 3 and 5 positions of butoxyphenyl group), 7.21–7.30 (5H, m, aromatic of benzyl group), 8.01 (2H, d, J=8.6 Hz, 2 and 6 positions of butoxyphenyl group), 8.24 (1H, s, 8 position of purine skeleton), <NH was not observed>

TOF-MS: 375 for $C_{22}H_{23}N_4O_2$ (M+H)

HPLC: Purity: 99.5%, Retention time: 22.07 min. (the same conditions as in Example 1)

EXAMPLE 13

7-Benzyl-2-(2-fluorophenyl)hypoxanthine

An amidation reaction and post-treatment were carried out according to the conditions of Example 1, using 2.2 g (10 mmol) of 4-amino-1-benzyl-5-imidazolecarboxamide prepared in Reference Example 2 and 2-fluorobenzoyl chloride instead of benzoyl chloride to obtain a crude amide product. The crude amide product was purified by suspension in hot methanol to obtain 1.69 g of 4-(2-fluorobenzoylamino)-1-benzyl-5-imidazolecarboxamide (yield 97%).

A cyclization reaction was carried out for 7.5 hours under the same conditions as in Example 1 using 1.0 g (2.96 mmol) of the resulting amide. The resulting product was post-treated to obtain crude crystals, which were purified by suspension in hot methanol to obtain 0.68 g of 7-benzyl-2-(2-fluorophenyl)hypoxanthine (yield 72%).

$^1$H-NMR (300 MHz, DMSO-d$_6$, δ ppm)

5.60 (2H, methylene of benzyl group), 7.32–7.38 (7H, m, aromatic of benzyl group (5H), aromatic of 2-fluorophenyl group (2H)), 7.58–7.69 (1H, m, aromatic of 2-fluorophenyl), 7.71–7.74 (1H, m, 6 position of 2-fluorophenyl group), 8.46 (1H, s, 8 position of purine skeleton), 12.58 (1H, br. s, NH)

TOF-MS: 321 for $C_{18}H_{14}FN_4O$ (M+H)

HPLC: Purity: 99%, Retention time: 17.79 min. (the same conditions as in Example 1)

EXAMPLE 14

7-Benzyl-2-(4-methoxyphenyl)hypoxanthine

An amidation reaction and post-treatment were carried out according to the conditions of Example 1, using 1.52 g (7 mmol) of 4-amino-1-benzyl-5-imidazolecarboxamide prepared in Reference Example 2 and 4-methoxy benzoyl chloride separately prepared according to a conventional method, instead of benzoyl chloride, to obtain a crude amide product. The crude amide product was purified by suspension in hot methanol to obtain 1.31 g of 4-(4-methoxybenzoylamino)-1-benzyl-5-imidazolecarboxamide (yield 53%).

A cyclization reaction was carried out for 10 hours under the same conditions as in Example 1 using 1.3 g (3.71 mmol) of the resulting amide. The resulting product was post-treated to obtain crude crystals, which were purified by suspension in hot methanol to obtain 0.98 g of 7-benzyl-2-(4-methoxyphenyl)hypoxanthine (yield 80%).

$^1$H-NMR (300 MHz, DMSO-d$_6$, δ ppm):

3.83 (3H, s, methoxy group), 5.59 (2H, s, methylene of benzyl group), 7.04 (2H, d, J=10.2 Hz, 3 and 5 positions of 4-methoxyphenyl group), 7.25–7.41 (5H, m, aromatic of benzyl group), 8.09 (2H, d, J=10.2 Hz, 2 and 6 positions of 4-methoxyphenyl group), 8.36 (1H, s, 8 position of purine skeleton), 12.00 (1H, s, NH)

TOF-MS: 333 for $C_{19}H_{17}N_4O_2$ (M+H)

HPLC: Purity: 99%, Retention time: 17.78 min. (the same conditions as in Example 1)

EXAMPLE 15

7-Benzyl-2-(2-methoxyphenyl)hypoxanthine

An amidation reaction and post-treatment were carried out according to the conditions of Example 1, using 2.2 g (10 mmol) of 4-amino-1-benzyl-5-imidazolecarboxamide prepared in Reference Example 2 and 2-methoxybenzoyl chloride separately prepared according to a conventional method, instead of benzoyl chloride, to obtain a crude amide product. The crude amide product was purified by suspension in hot methanol to obtain 1.87 g of 4-(2-methoxybenzoylamino)-1-benzyl-5-imidazolecarboxamide (yield 53%).

A cyclization reaction was carried out for 10 hours under the same conditions as in Example 1 using 1.77 g (5.04 mmol) of the resulting amide. The resulting product was post-treated to obtain crude crystals, which were purified by suspension in hot methanol to obtain 1.14 g of 7-benzyl-2-(2-methoxyphenyl)hypoxanthine (yield 68%).

$^1$H-NMR (300 MHz, DMSO-d$_6$δ ppm):

3.84 (3H, s, methoxy group), 5.58 (2H, s, methylene of benzyl group), 7.07–7.65 (9H, m, aromatic of benzyl group (5H), aromatic of 2-methoxyphenyl(4H)).

8.43 (1H, s, 8 position of purine skeleton), 12.09 (3H, s, NH)

TOF-MS: 333 for $C_{19}H_{17}N_4O$ (M+H)

HPLC: Purity: 98%, Retention time, 18.16 min. (the same conditions as in Example 1)

EXAMPLE 16

7-Benzyl-2-(3-methoxyphenyl)hypoxanthine

An amidation reaction and post-treatment were carried out according to the conditions of Example 1, using 2.2 g (10 mmol) of 4-amino-1-benzyl-5-imidazolecarboxamide prepared in Reference Example 2 and 3-methoxybenzoyl chloride separately prepared according to a conventional method, instead of benzoyl benzoyl chloride, to obtain a crude amide product. The crude amide product was purified by suspension in hot methanol to obtain 0.91 g of 4-(3-methoxybenzoylamino)-1-benzyl-5-imidazolecarboxamide (yield 26%).

A cyclization reaction was carried out for 10 hours under the same conditions as in Example 1 using 0.86 g (2.46 mmol) of the resulting amide. The resulting product was post-treated to obtain crude crystals, which were purified by suspension in hot methanol to obtain 0.64 g of 7-benzyl-2-(3-methoxyphenyl)hypoxanthine (yield 78%).

$^1$H-NMR (300 MHz, DMSO-d$_6$, δ ppm):

3.85 (3H, s, methoxy group), 5.60 (2H, s, methylene of benzyl group), 7.08–7.11 (1H, m, 4 position of 3-methoxyphenyl group), 7.33–7.65 (6H, m, aromatic of benzyl group (5H), 5 position of 3-methoxyphenyl), 7.65–7.69 (2H, m, 2 and 6 positions of 3-methoxyphenyl group), 8.44 (1H, s, 8 position of purine skeleton), 12.50 (1H, s, NH)

TOF-MS: 333 for $C_{19}H_{17}N_4O_2$ (M+H)

HPLC: Purity: 99%, Retention time: 17.74 min. (the same conditions as in Example 1)

EXAMPLE 17

7-Benzyl-2-(3-pyridylmethyl)hypoxanthine 1.4 ml (10 mmol) of triethylamine, 1.5 g (11 mmol) of 1-hydroxybenzotriazole, and 2.3 g (12 mmol) of 1-(3-dimethylaminopropyl)-3-ethylcarbodiimide hydrochloride were added to a solution of 1.7 g (10 mmol) of 3-pyridylacetic acid hydrochloride in 100 ml of N,N-dimethylformamide under cooling with ice. The mixture was stirred for one hour while cooling with ice. 2.05 g (9.5 mmol) of 4-amino-1-benzyl-5-imidazole carboxamide which was obtained in Reference Example 2 was added to the reaction solution, followed by stirring overnight. The reaction solution was concentrated under vacuum and 5% aqueous solution of sodium hydrogencarbonate was added to the concentrate to deposite a solid precipitate. The precipitate was collected by filtration through a funnel with a glass filter. The resulting solid was washed with 5% aqueous solution of sodium hydrogencarbonate, then with distilled water, and dried under vacuum to obtain a crude product, which was recrystallized from hot methanol to obtain 1.83 g of 1-benzyl-4-(3-pyridylacetylamino)-5-imidazolecarboxamide (yield 57%).

A cyclization reaction was carried out for 2.5 hours using 0.67 g (2 mmol) of the resulting amide. The resulting product was post-treated under the same conditions as in Example 1. The resulting crude crystals were purified by suspension in hot methanol to obtain 0.45 g of 7-benzyl-2-(3-pyridylmethyl)hypoxanthine (yield 71%).

$^1$H-NMR (300 MHz, DMSO-d$_6$, δ ppm):

3.98 (2H, s, methylene of 3-pyridylmethyl group), 5.53 (2H, s, methylene of benzyl group), 7.32 (6H, m, aromatic of benzyl group (5H), 5 position of 3-pyridyl group), 7.73 (1H, s, 4 position of 3-pyridyl group), 8.43 (1H, s, 8 position of purine skeleton), 8.46 (1H, m, 6 position of 3-pyridyl group), 8.56 (1H, m, 2 position of 3-pyridyl group), 12.50 (1H, br, s, NH)

TOF-MS: 318 for $C_{18}H_{16}N_5O_2$ (M+H)

HPLC: Purity: 99%, Retention time: 12.97 min. (the same conditions as in Example 1)

EXAMPLE 18

7-Benzyl-2-methylhypoxanthine 2.2 g (10 mmol) of 4-amino-1-benzyl-5-imidazole carboxamide prepared in Reference Example 2 was dissolved in 200 ml of N,N-dimethylformamide. 2.1 ml (15 mmol) of triethylamine and 1.06 ml (15 mmol) of acetyl chloride were added to the mixture while cooling with ice, followed by stirring overnight. The reaction product was concentrated under vacuum to obtain a crude product, which was recrystallized from hot methanol to obtain 0.86 g of 4-acetylamino-1-benzyl-5-imidazolecarboxamide (yield 33%).

A cyclization reaction was carried out for four hours using 0.86 g (3.3 mmol) of the resulting amide. The resulting product was post-treated under the same conditions as in Example 1. The resulting crude crystals were purified by suspension in hot methanol to obtain 0.73 g of 7-benzyl-2-methylhypoxanthine (yield 92%).

$^1$H-NMR (300 MHz, DMSO-$d_6$, δ ppm):

2.32 (3H, s, methyl group), 5.53 (2H, s, methylene of benzyl group), 7.26–7.32 (5H, m, aromatic of benzyl group), 8.31 (1H, s, 8 position of purine skeleton), 12.17 (1H, br. s, NH)

TOF-MS: 241 for $C_{13}H_{13}N_4O$ (M+H)

HPLC: Purity: 99%, Retention time: 13.65 min. (the same conditions as in Example 1)

EXAMPLE 19

7-Benzyl-2-cyclopentylmethylhypoxanthine 4.14 ml (20 mmol) of diphenyl chlorophosphate and 2.8 ml (20 mmol) of triethylamine were added to a solution of 2.5 ml (20 mmol) of cyclopentylacetic acid in 20 ml of N,N-dimethylformamide while cooling with ice. The solution was stirred for one hour while cooling with ice. A solution of 2.2 g (10 mmol) of 4-amino-1-benzyl-5-imidazolecarboxamide prepared in Reference Example 2 in 200 ml of N,N-dimethylformamide was added to the reaction solution, followed by stirring overnight. After concentration under vacuum, 5% aqueous solution of sodium hydrogencarbonate was added to obtain a solid precipitate. The precipitate was collected by filtration using a funnel equipped with a glass filter, washed with 5% aqueous solution of sodium hydrogencarbonate and distilled water, and dried under vacuum to obtain a crude product. This crude product was purified by suspension in hot methanol to obtain 1.77 g of 1-benzyl-4-cyclopentylacetylamino-5-imidazolecarboxamide (yield 54%).

A cyclization reaction was carried out for 3.5 hours using 1.35 g (4.14 mmol) of the resulting amide. The resulting product was post-treated under the same conditions as in Example 1 to obtain 1.13 g of 7-benzyl-2-cyclopentylmethylhypoxanthine (yield 89%).

$^1$H-NMR (300 MHz, DMSO-$d_6$, δ ppm):

1.17–1.22 (2H, m, 2H in 4 methylene groups of cyclopentyl), 1.44–1.69 (6H, m, 6H in 4 methylene groups of cyclopentyl), 2.23–2.34 (1H, m, methine of cyclopentyl), 2.57 (2H, d, J=8.7 Hz, methylene bonded to 2 position of cyclopentylmethyl group), 5.53 (2H, s, methylene of benzyl group), 7.28–7.35 (5H, m, aromatic of benzyl group), 8.33 (1H, s, 8 position of purine skeleton), 12.14 (1H, br. s, NH)

TOF-MS: 309 for $C_{18}H_{21}N_4O$ (M+H)

HPLC: Purity: 99%, Retention time: 18.39 min. (the same conditions as in Example 1)

EXAMPLE 20

7-Benzyl-2-cyclohexylhypoxanthine

An amidation reaction and a post-treatment were carried out according to the conditions of Example 18, using 2.2 g (10 mmol) of 4-amino-1-benzyl-5-imidazolecarboxamide prepared in Reference Example 2 and cyclohexanecarbonyl chloride separately prepared according to a conventional method, instead of acetyl chloride, to obtain a crude crystals. The crude crystals were purified by suspension in hot methanol to obtain 1.62 g of 4-cyclohexylcarbonylamino-1-benzyl-5-imidazolecarboxamide (yield 49%).

A cyclization reaction was carried out for 4 hours under the same conditions as in Example 1 using 1.3 g (4 mmol) of the resulting amide. The resulting product was post-treated to obtain crude crystals, which were purified by suspension in hot methanol to obtain 1.1 g of 7-benzyl-2-cyclohexylhypoxanthine (yield 90%).

$^1$H-NMR (300 MHz, DMSO-$d_6$, δ ppm):

1.25–1.81 (10H, m, methylene of cyclohexyl group), 2.56 (1H, m, methine of cyclohexyl group), 5.52 (2H, s, methylene of benzyl group), 7.33–7.35 (5H, m, aromatic of benzyl group), 8.33 (1H, s, 8 position of purine skeleton), 12.06 (1H, br. s, W)

TOF-MS: 309 for $C_{18}H_{24}N_4O$ (M+H)

HPLC: Purity: 92%, Retention time: 15.59 min. (the same conditions as in Example 1)

EXAMPLE 21

7-Benzyl-2-ethylhypoxanthine 2.59 g (12 mmol) of 4-amino-1-benzyl-5-imidazole carboxamide prepared in Reference Example 2 was dissolved in 200 ml of N,N-dimethylformamide. 2.52 ml (18 mmol) of triethylamine and 2.5 ml (18 mmol) of propionic anhydride were added to the solution while cooling, followed by stirring overnight. The reaction solution was concentrated under vacuum, then 5% aqueous solution of sodium hydrogencarbonate was added to the concentrate to precipitate a crude product. The precipitate was collected by filtration using a funnel equipped with a glass filter, washed with 5% aqueous solution of sodium hydrogencarbonate and distilled water, and dried under vacuum to obtain a crude product. This crude product was purified by suspension in hot methanol to obtain 2.33 g of 1-benzyl-4-propanoylamino-5-imidazolecarboxamide (yield 62%).

A cyclization reaction was carried out for 5 hours using 1.91 g (7 mmol) of the resulting amide. The resulting product was post-treated under the same conditions as in Example 1 to obtain 1.26 g of 7-benzyl-2-ethylhypoxanthine (yield 71%).

$^1$H-NMR (300 MHz, DMSO-d$_6$, δ ppm):

1.20 (3H, t, J=8.1 Hz, methyl of ethyl group)

2.60 (2H, q, J=8.1 Hz, methylene of ethyl group), 5.53 (2H, s, methylene of benzyl group), 7.27–7.34 (5H, m, aromatic of benzyl group), 8.33 (1H, s, 8 position of purine skeleton), 12.15 (1H, br. s, NH)

TOF-MS: 254 calculated for C$_{14}$H$_{15}$N$_4$O (M+H) 255

HPLC: Purity: 99%, Retention time: 14.43 min. (the same conditions as in Example 1)

EXAMPLE 22

7-Hexyl-2-phenylhypoxanthine

N-alkylation and acid hydrolysis reactions were carried out following the conditions of Reference Example 2, using 6.00 g (28.0 mmol) of the intermediate material 4-benzylideneamino-5-imidazolecarboxamide obtained in the Reference Example 1 and 1-iodohexane, instead of benzyl chloride, to produce 3.82 g of 4-amino-1-hexyl-5-imidazolecarboxamide hydrochloride (yield 65%).

1.50 g (6.08 mmol) of the amine hydrochloride thus obtained was suspended in 20 ml of dry pyridine and 1.1 ml of benzoyl chloride was added, followed by stirring for two days at room temperature. After the addition of 100 ml of distilled water, the mixture was extracted twice using dichloromethane. The extract was washed once with a saturated aqueous solution of sodium chloride and dried over anhydrous magnesium sulfate. A crude amide was obtained by evaporating the solvent.

A cyclization reaction was carried out for 16 hours using the crude amide under the same conditions as in Example 1 and crude crystals obtained by a post-treatment were recrystallized from ethanol to produce 0.57 g of 7-hexyl-2-phenylhypoxanthine. Yield: 32% (2 steps).

$^1$H-NMR (270 MHz, CDCl$_3$, δ ppm):

0.86 (3H, m, methyl of hexyl group), 1.30 (6H, m, 3 methylenes of hexyl group), 1.95 (2H, m, methylene of hexyl group), 4.41 (2H, t, J=7.0 Hz, N-binding methylene of hexyl group), 7.54 (3H, m, 3,4 and 5 positions of phenyl group), 7.90 (1H, s, 8 position of purine skeleton), 8.22 (2H, m, 2 and 6 positions of phenyl group), 11.36 (1H, br. s, NH)

TOF-MS: 296 calculated for C$_{17}$H$_{21}$N$_4$O (M+H) 297

HPLC: Purity: 99.4%, Retention time: 19.2 min. (the same conditions as in Example 1)

EXAMPLE 23

7-Cyclohexylmethyl-2-phenylhypoxanthine

N-alkylation and acid hydrolysis reactions were carried out following the conditions of Reference Example 2, using 6.00 g (28.0 mmol) of the intermediate material 4-benzylideneamino-5-imidazolecarboxamide obtained in the Reference Example 1 and cyclohexylmethyl bromide, instead of benzyl chloride, to produce 1.38 g of 4-amino-1-hexyl-5-imidazolecarboxamide hydrochloride as a precipitation solid at the time of hydrolysis and 2.28 g of 4-amino-1-hexyl-5-imidazolecarboxamide after neutralization (total yield: 62%).

1.38 g (5.33 mmol) of the amine hydrochloride thus obtained was reacted with benzoyl chloride under the same conditions as in Example 22 and a crude amide was obtained after a post-treatment.

A cyclization reaction was carried out for 12 hours using the crude amide under the same conditions as in Example 1 and crude crystals obtained by a post-treatment were recrystallized from ethanol-hexane to produce 0.48 g of 7-cyclohexylmethyl-2-phenylhypoxanthine. Yield: 29% (2 steps).

$^1$H-NMR (270 MHz, DMSO-d$_6$, δ ppm):

0.9–1.3 (5H, m, 5H in the methylenes of cyclohexyl group), 1.4–1.7 (5H, m, 5H in the methylenes of cyclohexyl group), 1.87 (1H, m, methine of cyclohexyl group), 4.21 (2H, d, J=7.3 Hz, N-binding methylene of cyclohexylmethyl group), 7.54 (3H, m, 3,4 and 5 positions of phenyl group), 8.08 (2H, m, 2 and 6 positions of phenyl group), 8.23 (1H, s, 8 position of purine skeleton), 11.36 (1H, br. s, NH)

TOF-MS: 309 for C$_{18}$H$_{21}$N$_4$O (M+H)

HPLC: Purity: 99.0%, Retention time: 18.9 min. (the same conditions as in Example 1)

EXAMPLE 24

7-(2-Methylpropyl)-2-phenylhypoxanthine

N-alkylation and acid hydrolysis reactions were carried out following the conditions of Reference Example 2, using 6.01 g (28.1 mmol) of 4-benzylideneamino-5-imidazolecarboxamide obtained in the Reference Example 1 and 2-methyl-1-bromopropane, instead of benzyl chloride, to produce 1.84 g of 4-amino-1-(2-methylpropyl)-5-imidazolecarboxamide hydrochloride and 1.16 g of 4-amino-1-(2-methylpropyl)-5-imidazolecarboxamide after neutralization (total yield: 50%).

1.15 g (6.31 mmol) of the amine hydrochloride thus obtained was reacted and post-treated under the same conditions as in Example 22 to obtain 1.71 g of a crude amide.

A cyclization reaction was carried out for 6 hours using the crude amide under the same conditions as in Example 1 and crude crystals obtained by a post-treatment were recrystallized from ethanol-hexane mixed solvent to produce 0.54 g of 7-(2-methylpropyl)-2-phenylhypoxanthine. Yield: 32% (2 steps).

$^1$H-NMR (270 MHz, DMSO-d$_6$, δ ppm):

0.86 (6H, d, J=7.0 Hz, methyls of 2-methylpropyl group), 2.19 (1H, m, methine of 2-methylpropyl group), 4.17 (2H, d, J=7. 3 Hz, methylen of 2-methylpropyl group), 7.54 (3H, m, 3,4and 5 positions of phenyl group), 8.09 (2H, dd, J=7.8, 1.6 Hz, 2 and 6 positions of phenyl group), 8.25 The (1H, s, 8 position of purine skeleton), 12.47 (1H, br. s, NH)

TOF-MS: 269 for C$_{15}$H$_{17}$N$_4$O (M+H)

HPLC: Purity: 99.2%, Retention time: 15.6 min. (the same conditions as in Example 1)

EXAMPLE 25

7-Benzyl-2-(2,2-dimethylpropyl)hypoxanthine

A reaction and a post-treatment were carried out following the conditions of Example 19, using 2.2 g (10 mmol)

Reference Example 2 and 3,3-dimethylbutanoic acid, instead of cyclopentylacetic acid, to produce 1.65 g of 1-benzyl-4-(3,3-dimethylbutanoylamino)-5-imidazolecarboxamide (yield 52%).

A cyclization reaction was carried out for 7 hours using 1.65 g (5.25 mmol) of the amide obtained above under the same conditions as in Example 1. The resulting product was post-treated to obtain 1.2 g of 7-benzyl-2-(2,2-dimethylpropyl)hypoxanthine (yield 77%).

1H-NMR (300 MHz, DMSO-$d_6$, δ ppm):

0.96 (9H, s, methyls of dimethylpropyl group), 2.49 (2H, s, methylene of propyl group), 5.53 (2H, s, methylene of benzyl group), 7.33–7.35 (5H, m, aromatic of benzyl group), 8.32 (1H, s, 8 position of purine skeleton), 12.04 (1H, br. s, NH)

TOF-MS: 297 calculated for $C_{17}H_{21}N_4O$ (M+H)

HPLC: Purity: 99%, Retention time: 17.70 min. (the same conditions as in Example 1)

EXAMPLE 26

7-Benzyl-2-cyclopentylhypoxanthine

A reaction and a post-treatment were carried out following the conditions of Example 19, using 2.2 g (10 mmol) of 4-amino-1-benzyl-5-imidazolecarboxamide obtained in Reference Example 2 and cyclopentylcarboxylic acid, instead of cyclopentylacetic acid, to produce crude crystals, which were recrystallized from hot methanol to obtain 1.42 g of 1-benzyl-4-cyclopentylcarbonylamino-5-imidazole carboxamide (yield 46%).

A cyclization reaction was carried out for 4 hours using 1.24 g (4 mmol) of the amide obtained above under the same conditions as in Example 1. The resulting product was post-treated to obtain 1.0 g of 7-benzyl-2-cyclopentylhypoxanthine (yield 88%).

$^1$H-NMR (300 MHz, DMSO-$d_6$, δppm):

1.58–1.95 (8H, m, methylenes of cyclopentyl group), 3.03–3.19 (1H, m, methine of cyclopentyl group), 5.52 (2H, s, methylene of benzyl group), 7.28–7.33 (5H, m, aromatic of benzyl group), 8.30 (1H, s, 8 position of purine skeleton), 12.10 (1H, br. s, NH)

TOF-MS: 295 calculated for $C_{17}H_{19}N_4O$ (M+H)

HPLC: Purity: 97%, Retention time 14.49 min. (the same conditions as in Example 1)

EXAMPLE 27

7-Benzyl-2-propylhypoxanthine

An amidation reaction and a post-treatment were carried out following the conditions of Example 21, using 2.2 g (10 mmol) of 4-amino-1-benzyl-5-imidazolecarboxamide obtained in Reference Example 2 and butyric anhydride instead of propionic anhydride to produce a crude crystals, which were purified by suspension in hot methanol, thereby obtaining 1.36 g of 1-benzyl-4-butanoylamino-5-imidazolecarboxamide (yield 48%).

A cyclization reaction was carried out for 2.5 hours using 1.15 g (4 mmol) of the amide obtained above. The resulting product was post-treated and purified by suspension in hot methanol to obtain 0.91 g of 7-benzyl-2-propylhypoxanthine (yield 95%).

$^1$H-NMR (300 MHz, DMSO-$d_6$, δ ppm):

0.90 (3H, t, J=7.2 Hz, methyl of propyl group), 1.69 (2H, qt, J=7.2 Hz, 6.6 Hz, methylene of propyl group), 2.55 (2H, t, J=6.6 Hz, methylene of propyl group), 5.52 (2H, s, methylene of benzyl group), 7.27–7.32 (5H, m, aromatic of benzyl group), 8.31 (1H, s, 8 position of purine skeleton), 12.13 (1H, br. s, NH)

TOF-MS: 269 calculated for $C_{15}H_{17}N_4O$ (M+H)

HPLC: Purity: 100%, Retention time: 15.22 min. (the same conditions as in Example 1)

EXAMPLE 28

7-Benzyl-2-(4-chlorophenyl)hypoxanthine

A reaction and a post-treatment were carried out following the conditions of Example 22, using 1.27 g (5.81 mmol) of 4-amino-1-benzyl-5-imidazolecarboxamide obtained in Reference Example 2 and, instead of benzoyl chloride, 4-chlorobenzoyl chloride which was separately prepared by a conventional method to produce 1.84 g of 1-benzyl-4-(4-chlorobenzoylamino)-5-imidazolecarboxamide (yield 89%).

A cyclization reaction was carried out for 32 hours using 1.84 g (5.19 mmol) of the amide obtained above under the same conditions as in Example 1. The resulting product was post-treated to obtain 1.33 g of 7-benzyl-2-(4-chlorophenyl)hypoxanthine (yield 74%).

$^1$H-NMR (300 MHz, DMSO-$d_6$, δ ppm):

5.59 (2H, s, methylene of benzyl group), 7.29–7.40 (5H, m, aromatic of benzyl group), 7.40–7.53 (1H, m, aromatic of chlorophenyl group), 7.53–7.60 (3H, m, aromatic of chlorophenyl group), 8.44 (1H, s, 8 position of purine skeleton), 12.62 (1H, br. s, NH)

TOF-MS: 337 for $C_{18}H_{14}ClN_4O$ (M+H)

HPLC: Purity: 100%, Retention time: 17.42 min. (the same conditions as in Example 1)

EXAMPLE 29

7-Benzyl-2-(3-chlorophenyl)hypoxanthine

A reaction and a post-treatment were carried out following the conditions of Example 22, using 1.27 g (5.81 mmol) of 4-amino-1-benzyl-5-imidazolecarboxamide obtained in Reference Example 2 and 3-chlorobenzoyl chloride which was separately prepared to produce 1.84 g of 1-benzyl-4-(3-chlorobenzoylamino)-5-imidazolecarboxamide (yield 89%).

A cyclization reaction was carried out for 32 hours using 1.84 g (5.81 mmol) of the amide obtained above under the same conditions as in Example 1. The resulting product was post-treated to obtain 1.33 g of 7-benzyl-2-(3-chlorophenyl)hypoxanthine (yield 74%).

$^1$H-NMR (300 MHz, DMSO-$d_6$, δ ppm):

5.60 (2H, s, methylene of benzyl group), 7.32–7.38 (5H, m, aromatic of benzyl group), 7.58 (2H, d, J=8.6 Hz, 3 and 5 positions of 4-chlorophenyl group), 8.11 (2H, d, J=8.6 Hz, 2 and 6 positions of chlorophenyl group), 8.40 (1H, s, 8 position of purine skeleton), 12.55 (1H, br. s, NH)

TOF-MS: 337 for $C_{18}H_{14}ClN_{4O}$ (M+H)

HPLC: Purity: 100%, Retention time: 17.42 min. (the same conditions as in Example 1)

EXAMPLE 30

7-Benzyl-2-(3-hydroxyphenyl)hypoxanthine 1.00 g (3.01 mmol) of 7-benzyl-2-(3-methoxyphenyl) hypoxanthine prepared according to the same method as in Example 16 was dissolved in 20 ml of acetic acid. 3 ml of hydrobromic acid was added to the solution, followed by stirring for 35.5 hours at 100° C. Crystals obtained by cooling was separated by filtration and washed with distilled water and ethanol. The resulting crude crystals were purified by recrystallization from ethanol to obtain 0.64 g of 7-benzyl-2-(3-hydroxyphenyl)hypoxanthine (yield 67%).

$^1$H-NMR (300 MHz, DMSO-$d_6$, δ ppm):

5.62 (2H, s, methylene of benzyl group), 6.95 (1H, d, J=7.3 Hz, 4 position of 3-OH phenyl group), 7.27–7.43 (6H, m, aromatic of benzyl group, 5 position of 3-OH phenyl group), 7.49 (1H, d, J=7.3 Hz, 6 position of 3-OH phenyl group), 8.69 (1H, s, 8 position of purine skeleton), 9.60 (1H, br. s, OH), 12. 60 (1H, br. s, NH)

TOF-MS: 318 f or $C_{18}H_{15}N_4O_2$ (M+H) 319

HPLC: Purity: 97.2%, Retention time: 15.80 min. (the same conditions as in Example 1)

EXAMPLE 31

7-Benzyl-2-(2,4-dichlorophenyl)hypoxanthine

A reaction and a post-treatment were carried out following the conditions of Example 1, using 3.24 g (15 mol) of 4-amino-1-benzyl-5-imidazolecarboxamide obtained in Reference Example 2 and, instead of benzoyl chloride, 2,4-dichlorobenzoyl chloride which was separately prepared by a conventional method to produce crude crystals, which were purified by suspension in hot methanol, thereby obtaining 4.3 g of 1-benzyl-4-(2,4-dichlorobenzoylamino)-5-imidazole carboxamide (yield 74%).

A cyclization reaction was carried out for 20 hours using 4.0 g (10.28 mmol) of the amide obtained above under the same conditions as in Example 1. The resulting product was post-treated to obtain crude crystals, which were recrystallized from a solvent mixture of N,N-dimethylformamide and methanol, thereby producing 2.25 g of 7-benzyl-2-(2,4-dichlorophenyl)hypoxanthine (yield 59%).

$^1$H-NMR (300 MHz, DMSO-$d_6$, δ ppm):

5.88 (2H, s, methylene of benzyl group), 7.29–7.40 (6H, m, aromatic of benzyl group, 3 position of dichlorophenyl group), 7.55 (1H, d, J=9 Hz, 5 or 6 position of dichloro phenyl group), 7.64 (1H, d, J=9 Hz, 5 or 6 position of dichloro phenyl group), 8.46 (1H, s, 8 position of purine skeleton), 12.66 (1H, br. s, NH)

TOF-MS: 372 for $C_{18}H_{13}Cl_2N_4O$ (M+H)

HPLC: Purity: 94%, Retention time: 20.02 min. (the same conditions as in Example 1)

EXAMPLE 32

7-Benzyl-2-(4-methylaminosulfonylphenyl) hypoxanthine 2.8 ml (20 mmol) triethylamine was added to and dissolved in a suspension of 4.4 g (20 mmol) of 4-chlorosulfonylbenzoic acid in dichloromethane. To the solution 3.1 ml of 40% aqueous solution of methylamine was added and stirred at room temperature overnight. After the reaction solution was concentrated under vacuum, the residue was dissolved in ethyl acetate-5% sodium hydrogencarbonate aqueous solution. The water layer was washed with ethyl acetate and adjusted to 2–3 pH with citric acid. The organic layer obtained by extracting the water layer with ethyl acetate was washed with distilled water, then with saturated brine, dried over anhydrous magnesium sulfate. This solution was concentrated under vacuum and the residue was crystallized from ethyl acetate-hexane to obtain 2.9 g of 4 -methylaminosulfonylbenzoic acid (yield 67%).

An amidation reaction and a post-treatment were carried out following the conditions of Example 17, using 2.0 g (9.3 mmol) of 4-amino-1-benzyl-5-imidazolecarboxamide obtained in Reference Example 2 and 4-methylaminosulfonylbenzoic acid instead of 3-pyridylacetic acid hydrochloride to produce crude crystals, which were purified by suspension in hot methanol, thereby obtaining 2.16 g of 1-benzyl-4-(4-methylaminosulfonylbenzoylamino)-5-imidazolecarboxamide (yield 56%).

A cyclization reaction was carried out under the same conditions as in Example 1 for 10 hours using 2.16 g (5.2 mmol) of the amide obtained above. The resulting product was post-treated and purified by suspension in hot methanol to obtain 1.55 g of 7-benzyl-2-(4-methylaminosulfonylphenyl) hypoxanthine (yield 75%).

$^1$H-NMR (300 MHz, DMSO-$d_6$, δ ppm):

2.46 (3H, d, J=4 Hz, methyl of methylaminosulfonyl group), 5.61 (2H, s, methylene of benzyl group), 7.31–7.37 (5H, m, aromatic of benzyl group), 7.60 (1H, q, J=4 Hz, NH of methylaminosulfonyl group), 7.89 (2H, d, J=8.5 Hz, 2 and 6 positions of methylaminosulfonylphenyl group), 8.27 (2H, d, J=8.5 Hz, 3 and 5 positions of methylaminosulfonylphenyl group), 8.46 (1H, s, 8 position of purine skeleton), 12.69 (1H, br. s, NH)

TOF-MS: 396 for $C_{19}H_{18}N_5O_3S$ (M+H)

HPLC: Purity: 98%, Retention time 17.24 min. (The same conditions as in Example 1)

EXAMPLE 33

7-Benzyl-2-butylhypoxanthine

An amidation reaction and a post-treatment were carried out following the conditions of Example 21, using 3.2 g (15 mmol) of 4-amino-1-benzyl-5-imidazolecarboxamide obtained in Reference Example 2 and valeric anhydride instead of propionic anhydride to produce crude crystals, which were purified by suspension in a hot solvent mixture of ethyl acetate and hexane, thereby obtaining 3.23 g of 1-benzyl-4-pentanoylamino-5-imidazolecarboxamide (yield 72%).

A cyclization reaction was carried out for 3 hours following the conditions of Example 1 using 3.0 g (10 mmol) of the amide obtained above. The resulting product was post-treated and purified by suspension in hot methanol to obtain 2.16 g of 7-benzyl-2-butylhypoxanthine (yield 77%).

$^1$H-NMR (300 MHz, DMSO-d$_6$, δ ppm):

0.86 (3H, t, J=7.4 Hz, methyl of butyl group), 1.30 (2H, m, methylene of butyl group), 1.65 (2H, m, methylene of butyl group), 2.58 (2H, t, J=7.5 Hz, N-binding methylene of butyl group), 5.52 (2H, s, methylene of benzyl group), 7.27–7.37 (5H, m, aromatic of benzyl group), 8.31 (1H, s, 8 position of purine skeleton), 12.12 (1H, br. s, NH)

TOF-MS: 283 calculated for C$_{16}$H$_{19}$N$_4$O (M+H)

HPLC: Purity: 99%, Retention time: 16.29 min. (the same conditions as in Example 1)

EXAMPLE 34

7-Benzyl-2-pentylhypoxanthine

An amidation reaction and a post-treatment were carried out following the conditions of Example 21, using 3.2 g (15 mmol) of 4-amino-1-benzyl-5-imidazolecarboxamide obtained in Reference Example 2 and hexanoic anhydride instead of propionic anhydride to produce crude crystals, which were purified by suspension in a hot solvent mixture of ethyl acetate and hexane, thereby obtaining 4.10 g of 1-benzyl-4-hexanoylamino-5-imidazolecarboxamide (yield 97%).

A cyclization reaction was carried out for 3 hours following the conditions of Example 1 using 3.77 g (12 mmol) of the amide obtained above. The resulting product was post-treated and purified by suspension in hot methanol to obtain 2.23 g of 7-benzyl-2-pentylhypoxanthine (yield 63%).

$^1$H-NMR (300 MHz, DMSO-d$_6$, δ ppm):

0.86 (3H, t, J=7 Hz, methyl of pentyl group), 1.27–1.33 (4H, m, methylenes of pentyl group), 1.67 (2H, m, methylene of benzyl group), 2.57 (2H, t, J=7.5 Hz, N-binding methylene of pentyl group), 5.52 (2H, s, methylene of benzyl group), 7.25–7.39 (5H, m, aromatic of benzyl group), 8.31 (1H, s, 8 position of purine skeleton), 12.12 (1H, br. s, NH)

TOF-MS: 297 calculated for C$_{17}$H$_{22}$N$_4$O (M+H)

HPLC: Purity: 99%, Retention time: 16.21 min. (the same conditions as in Example 1)

EXAMPLE 35

7-Benzyl-2-(3-(4-morpholinoethyloxy)1phenyl) hypoxanthine 4.14 g (30 mmol) of 3-hydroxybenzoic acid was dissolved in 250 ml of N,N-dimethylformamide, and 2.49 g (18 mmol) of potassium carbonate and 3.8 ml (33 mmol) of benzyl chloride were added, followed by stirring at room temperature overnight. After the reaction solution was concentrated under vacuum, the residue was dissolved in ethyl acetate and 5% aqueous solution of sodium hydrogencarbonate. The organic layer was washed with 5% aqueous solution of sodium hydrogencarbonate, distilled water, and then with saturated brine, dried over anhydrous magnesium sulfate. This solution was concentrated under vacuum and the residue was crystallized from ethyl acetate-hexane to obtain 3.96 g of benzyl 3-hydroxybenzoate (yield 58%).

3.88 g (17 mmol) of the phenol compound obtained was dissolved in 340 ml of N,N-dimethylformamide, and 2.49 g (18 mmol) of potassium carbonate and 4.04 g (25.5 mmol) of N-(2-chloroethyl)morpholine hydrochloride were added, followed by stirring at room temperature overnight. After vacuum concentration, the concentrate was dissolved in ethyl acetate and distilled water. The organic layer was washed with distilled water, an aqueous solution of 1 N sodium hydroxide, then saturated brine, and dried over anhydrous magnesium sulfate. After vacuum concentration, 5.91 g of an oily product of 3-(4-morpholinoethyloxy) benzyl benzoate was obtained (yield 100%).

5.91 g of the ester thus obtained was dissolved in 100 ml methanol and 0.3 g of 5% Pd/C was added to the solution, followed by stirring for four hours at room temperature in a hydrogenous atmosphere. After separation of Pd/C by filtration, the filtrate was concentrated under vacuum and crystallized from an ethyl acetate-hexane mixture to obtain 2.55 g of 3-(4-morpholinoethyloxy)benzoic acid (yield 60%).

An amidation reaction and a post-treatment were carried out following the conditions of Example 18, using 2.2 g (10 mmol) of 4-amino-1-benzyl-5-imidazolecarboxamide obtained in Reference Example 2 and, instead of acetic chloride, 3-(4-morpholinoethyloxy)benzoyl chloride which was separately prepared, to produce crude crystals. The crude crystals were purified by silica gel column chromatography and recrystallization to obtain 1.34 g of 4-(3-(4-morpholinoethyloxy)benzoylamino)-1-benzyl-5-imidazole carboxamide (yield 41%).

A cyclization reaction was carried out under the same conditions as in Example 1 for 6 hours using 1.3 g (2.89 mmol) of the amide compound obtained in the above procedure to obtain 0.83 g of 7-benzyl-2-(3-(4-morpholinoethyloxy)phenyl) hypoxanthine (yield 67%).

$^1$H-NMR (300 MHz, CDCl$_3$, δ ppm):

2.57 (4H, t, J=4.2 Hz, N-binding methylenes of morpholine), 2.79 (2H, t, J=5.7 Hz, N-binding methylene of morpholinoethyloxy group), 3.73 (4H, t, J=4.2 Hz, O-binding methylenes of morpholine), 4.17 (2H, t, J=5.7 Hz, O-binding methylene of morpholinoethyloxy group), 5.61 (2H, s, methylene of benzyl group), 7.04–7.07 (1H, m, 4 position of 3-(4-morpholinoethyloxy) phenyl group), 7.25–7.61 (6H, m, aromatic (5H) of benzyl group, 5 position of 3-(4-morpholinoethyloxy)phenyl group), 7.61–7.77 (2H, m, 2 and 6 positions of 3-(4-morpholinoethyloxy)phenyl group), 7.89 (1H, s, 8 position of purine skeleton), 10.79 (1H, br. s, NH)

TOF-MS: 432 for C$_{24}$H$_{26}$N$_5$O$_3$ (M+H)

HPLC: Purity: 90%, Retention time: 15.01 min. (the same conditions as in Example 1)

EXAMPLE 36

7-Benzyl-2-(4-(4-morpholinoethyloxy)phenyl) hypoxanthine 4.45 g of 4-(4-morpholinoethyloxy)benzoic acid was prepared in the same manner as in Example 35, except for using 4.04 g (17.7 mmol) of benzyl 4-hydroxybenzoate instead of benzyl 3-hydroxybenzoate (yield 100%).

An amidation reaction and a post-treatment were carried out following the conditions of Example 18, using 2.2 g (10 mmol) of 4-amino-1-benzyl-5-imidazolecarboxamide obtained in Reference Example 2 and 4-(4-morpholinoethyloxy)benzoyl chloride instead of acetyl chloride to produce crude crystals, which were purified by crystallizing from a solvent mixture of ethyl acetate and hexane, thereby producing 2.57 g of 4-(4-(4-morpholinoethyloxy)benzoylamino)-1-benzyl-5-imidazole carboxamide (yield 57%).

A cyclization reaction was carried out for 8 hours following the conditions of Example 1 using 2.5 g (5.56 mmol) of the amide obtained above. The resulting product was post-treated to obtain 0.56 g of 7-benzyl-2-(4-(4-morpholinoethyloxy)phenyl)hypoxanthine(yield 23%).

$^1$H-NMR (300 MHz, CDCl$_3$, δ ppm):

2.56 (4H, t, J=4.2 Hz, N-binding methylenes of morpholine), 2.80 (2H, t, J=5.7 Hz, N-binding methylene of morpholinoethyloxy group), 3.73 (4H, t, J=4.2 Hz, O-binding methylenes of morpholine), 4.11 (2H, t, J=5.7 Hz, O-binding methylene of morpholinoethyloxy group), 5.60 (2H, s, methylene of benzyl group), 6.94 (2H, d, J=8.7 Hz, 3 and 5 positions of 4-(4-morpholinoethyloxy)phenyl group), 7.34 (5H, m, aromatic of benzyl group (5H)), 7.88 (1H, s, 8 position of purine skeleton), 8.10 (2H, d, J=8.7 Hz, 2 and 6 positions of 4-(4-morpholinoethyloxy)phenyl group), 10.89 (1H, br. s, NH)

TOF-MS: 433 calculated for C$_{24}$H$_{26}$N$_5$O$_3$ (M+H) 432

HPLC: Purity: 90%, Retention time: 14.69 min. (the same conditions as in Example 1)

EXAMPLE 37

7-Benzyl-2-(2-chlorophenyl)hypoxanthine

An amidation reaction and a post-treatment were carried out following the conditions of Example 22, using 2.16 g (9.98 mmol) of 4-amino-1-benzyl-5-imidazolecarboxamide obtained in Reference Example 2 and 2-chlorobenzoyl chloride prepared seperately to produce 1.89 g of 4-(2-chlorobenzoylamino)-1-benzyl-5-imidazolecarboxamide (yield 92%).

A cyclization reaction was carried out for 32 hours following the conditions of Example 1 using 1.89 g (5.33 mmol) of the amide compound obtained above. The resulting product was post-treated to obtain 1.33 g of 7-benzyl-2-(2-chlorophenyl)hypoxanthine (yield 74%).

$^1$H-NMR (300 MHz, DMSO-d$_6$, δ ppm):

5.59 (2H, s, methylene of benzyl group), 7.29–7.40 (5H, m, aromatic of benzyl group), 7.40–7.53 (1H, m, aromatic of 2-chlorophenyl group), 7.53–7.60 (3H, m, aromatic of 2-chlorophenyl group), 8.44 (1H, s, 8 position of purine skeleton), 12.62 (1H, br. s, NH)

TOF-MS: 337 for C$_{18}$H$_{14}$ClN$_4$O (M+H)

HPLC: Purity: 100%, Retention time: 17.42 min. (the same conditions as in Example 1)

EXAMPLE 38

7-Benzyl-2-(4-hydroxyphenyl)hypoxanthine 1.52 g (4.57 mmol) of 7-benzyl-2-(4-methoxyphenyl) hypoxanthine prepared by the same method as in Example 14 was dissolved in 25 ml of acetic acid. After the addition of 3 ml of hydrobromic acid, the mixture was stirred for 58.5 hours at 100° C. After cooling, 10 ml of triethylamine and 100 ml of distilled water were added to the reaction mixture. The crystals produced were separated by filtration and washed with distilled water and ethanol to obtain 0.57 g of 7-benzyl-2-(4-hydroxyphenyl)hypoxanthine (yield 39%).

$^1$H-NMR (300 MHz, DMSO-d$_6$, δ ppm):

5.56 (2H, s, methylene of benzyl group), 6.84 (2H, d, J=7.8 Hz, 3 and 5 positions of 4-hydrophenyl group), 7.26–7.40 (5H, m, aromatic of benzyl group), 7.94 (2H, d, J=8.7 Hz, 2 and 6 positions of 4-hydrophenyl group), 8.36 (1H, s, 8 position of purine skeleton), NH and OH were not observed.

TOF-MS: 319 for C$_{18}$H$_{15}$N$_4$O$_2$ (M+H)

HPLC: Purity: 94.6%, Retention time: 15.87 min. (the same conditions as in Example 1)

EXAMPLE 39

7-Benzyl-2-(2-hydroxyphenyl)hypoxanthine 1.36 g (4.09 mmol) of 7-benzyl-2-(2-methoxyphenyl) hypoxanthine prepared by the same method as in Example 15 was dissolved in 20 ml of acetic acid. After the addition of 3 ml of hydrobromic acid, the mixture was stirred for 35.5 hours at 100° C. After cooling, the produced crystals were separated by filtration and washed with distilled water and ethanol. The crude crystals were purified by suspension in hot ethanol to obtain 0.88 g of 7-benzyl-2-(2-hydroxyphenyl)hypoxanthine (yield 68%).

$^1$H-NMR (300 MHz, DMSO-d$_6$, δ ppm), 5.59 (2H, s, methylene of benzyl group), 6.90–7.00 (2H, m, 3 and 5 positions of 2-hydrophenyl group), 7.28–7.40 (6H, m, aromatic of benzyl group, 4 position of 2-hydrophenyl group), 8.11 (1H, d, J=7.2 Hz, 6 position of 2-hydrophenyl group), 8.45 (1H, s, 8 position of purine skeleton), 12.3–12.8 (2H, br, NH, OH)

TOF-MS: 319 for C$_{18}$H$_{15}$N$_4$O$_2$ (M+H)

HPLC: Purity: 99.6%, Retention time: 18.42 min. (the same conditions as in Example 1)

EXAMPLE 40

7-Benzyl-2-(3-5-dimethoxyphenyl) hypoxanthine

A reaction and a post-treatment were carried out following the conditions of Example 22, using 2.16 g (9.98 mmol) of 4-amino-1-benzyl-5-imidazolecarboxamide obtained in Reference Example 2 and 3,5-dimethoxybenzoyl chloride which was separately prepared to produce 2.65 g of 4-(3,5-dimethoxybenzoylamino)-1-benzyl-5-imidazolecarboxamide (yield 70%).

A cyclization reaction was carried out under the same conditions as in Example 1 for 15.5 hours using 2.65 g (6.97 mmol) of the amide obtained above. The resulting product was post-treated to obtain 2.26 g of 7-benzyl-2-(3,5-dimethoxyphenyl)hypoxanthine (yield 90%).

$^1$H-NMR (300 MHz, DMSO-d$_6$, δ ppm):

3.82 (6H, s, MeO X2), 5.59 (2H, s, methylene of benzyl group), 6.64 (1H, s, 4 position of 3,5-dimethoxyphenyl group), 7.54 (7H, m, aromatic of benzyl group H, 2 and 6 positions of 3,5-dimethoxyphenyl group), 8.42 (1H, s, 8 position of purine skeleton), NH was not observed.

TOF-MS: 363 for $C_{20}H_{19}N_4O_3$ (M+H)

HPLC: Purity: 99.0%, Retention time: 18.77 min. (the same conditions as in Example 1)

EXAMPLE 41

7-Benzyl-2-(4-ethylaminosulfonylphenyl) hypoxanthine

A reaction was carried out following the conditions of Example 32 using 4.4 g (20 mmol) of 4-chlorosulfonylbenzoic acid and an ethylamine solution instead of the 40% aqueous solution of methylamine. The reaction product was post-treated to obtain 2.92 g of 4-ethylaminosulfonylbenzoic acid (yield 64%).

An amidation reaction and a post-treatment were carried out following the conditions of Example 17, using 2.0 g (9.3 mmol) of 4-amino-1-benzyl-5-imidazolecarboxamide obtained in Reference Example 2 and, instead of 3-pyridylacetic acid hydrochloride, 4-ethylaminosulfonylbenzoic acid which was produced in the above procedure. The crude crystals obtained were purified by suspension in hot methanol, thereby obtaining 3.68 g of 1-benzyl-4-(4-ethylaminosulfonylbenzoylamino)-5-imidazolecarboxamide (yield 92%).

A cyclization reaction was carried out under the same conditions as in Example 1 for 6 hours using 3.68 g (8.6 mmol) of the amide obtained above. The resulting product was post-treated and purified by suspension in hot methanol to obtain 2.33 g of 7-benzyl-2-(4-ethylaminosulfonylphenyl) hypoxanthine (yield 66%).

$^1$H-NMR (300 MHz, DMSO-d$_6$, δ ppm):

1.00 (3H, t, J=6.6 Hz, methyl of ethylaminosulfonyl group), 2.83 (2H, m, methyl of ethylaminosulfonyl group), 5.61 (2H, s, methylene of benzyl group), 7.17 (1H, t, J=3.6 Hz, NH of ethylaminoulfonyl group), 7.31–7.35 (5H, m, aromatic of benzyl group), 7.90 (2H, d, J=9 Hz, 2 and 6 positions of ethylaminosulfonyl phenyl group), 8.27 (2H, d, J=9 Hz, 3 and 5 positions of ethylaminosulfonylphenyl group), 8.46 (1H, s, 8 position of purine skeleton), 12.68 (1H, br. s, NH)

TOF-MS: 410 for $C_{20}H_{20}N_5O_3S$ (M+H)

HPLC: Purity: 99%, Retention time: 18.07 minutes (the same conditions as in Example 1)

EXAMPLE 42

7-Benzyl-2-methoxymethylhypoxanthine

An amidation reaction and post-treatment were carried out following the conditions of Example 18, using 3.24 g (15 mmol) of 4-amino-1-benzyl-5-imidazolecarboxamide obtained in Reference Example 2 and methoxyacetyl chloride instead of acetyl chloride to produce 1.85 g of 1-benzyl-4-methoxyacetylamino-5-imidazolecarboxamide (yield 43%).

A cyclization reaction was carried out for 4 hours following the conditions of Example 1 using 1.85 g (6.42 mmol) of the amide obtained above. The resulting product was post-treated and recrystallized from methanol to obtain 1.01 g of 7-benzyl-2-methoxymethylhypoxanthine (yield 58%).

$^1$H-NMR (300 MHz, DMSO-d$_6$, δ ppm):

3.34 (3H, s, methyl of methoxymethyl group), 4.29 (2H, s, methylene of methoxymethyl group), 5.55 (2H, s, methylene of benzyl group), 7.27–7.34 (5H, m, aromatic of benzyl group), 8.37 (1H, s, 8 position of purine skeleton), 12.23 (1H, br. s, NH)

TOF-MS: 271 calculated for $C_{14}H_{15}N_4O_2$ (M+H)

HPLC: Purity: 96%, Retention time: 14.54 minutes (the same conditions as in Example 1)

EXAMPLE 43

7-Benzyl-2-(3,5-dihydroxyphenyl)hypoxanthine 1.20 g (3.31 mmol) of 7-benzyl-2-(3,5-dimethoxy phenyl) hypoxanthine which was produced in Example 40 was dissolved in 15 ml of acetic acid. After the addition of 3 ml of hydrobromic acid, the mixture was stirred for 17 hours at 100° C. Crystals produced by cooling were separated by filtration and washed with distilled water and ethanol to obtain 0.75 g of 7-benzyl-2-(3,5-dihydroxyphenyl) hypoxanthine (yield 68%).

$^1$H-NMR (300 MHz, DMSO-d6, δ ppm):

5.57 (2H, s, methylene of 3,5-dihydroxyphenyl group), 6.37 (1H, s, 4 position of 3,5-dihydroxyphenyl group), 6.89 (2H, s, 2 and6 of positions of 3,5-dihydroxyphenyl group), 7.26–7.38 (5H, m, 3, 4and 5 positions of phenyl group), 8.39 (1H, s, 8 position of purine skeleton), 9.53 (2H, s, OH×2), 12.24 (1H, m, NH)

TOF-MS: 335 for $C_{18}H_{15}N_4O_3$ (M+H)

HPLC: Purity: 97.8%, Retention time: 15.27 minutes (the same conditions as in Example 1)

EXAMPLE 44

7-Benzyl-2-(2-aminoethyl)hypoxanthine

An amidation reaction and a post-treatment were carried out following the conditions of Example 19 using 2.2 g (10 mmol) of 4-amino-1-benzyl-5-imidazolecarboxamide obtained in Reference Example 2 and 3-t-butoxycarbonylaminopropionic acid instead of cyclopentylacetic acid to produce a crude product, which was purified by silica gel column chromatography and crystallization from a mixed solvent of ethyl acetate-hexane to obtain 2.98 g of 1-benzyl-4-(3-t-butoxycarbonylaminopropanoylamino)-5-imidazolecarboxamide (yield 77%).

A cyclization reaction was carried out for 4.5 hours following the conditions of Example 1 using 2.9 g (7.49 mmol) of the amide obtained above. The resulting product was post-treated and purified by silica gel column chromatography to obtain 1.2 g of 7-benzyl-2-(2-t-butoxycarbonylaminoethyl) hypoxanthine (yield 43%).

1.1 g (2.97 mmol) of this hypoxanthine derivative was dissolved in 80 ml of dioxane containing 4 N hydrogen chloride and stirred for one hour at 0° C. The reaction solution was concentrated under vacuum and the concentrate was recrystallized from ether to obtain 1.15 g of 7-benzyl-2-(2-aminoethyl)hypoxanthine hydrochloride.

$^1$H-NMR (300 MHz, DMSO-$d_6$, δ ppm):

3.04 (2H, t, 7.5 Hz, hypoxanthine side methylene of aminoethyl group), 3.16–3.23 (2H, m, amino group side methylene of aminoethyl group), 5.59 (2H, s, methylene of benzyl group), 7.29–7.39 (5H, m, aromatic of benzyl group), 8.21 (2H, br. s, amino group), 8.82 (1H, s, 8 position of purine skeleton), 12.62 (1H, br. s, NH)

TOF-MS=270 for $C_{14}H_{16}N_5O$ (M+H)

HPLC: Purity: 94%, Retention time: 12.66 minutes (the same conditions as in Example 1)

EXAMPLE 45

7-Benzyl-2-(3-ethoxyphenyl)hypoxanthine

A reaction and a post-treatment were carried out following the conditions of Example 1, using 2.34 g (10.8 mmol) of 4-amino-1-benzyl-5-imidazolecarboxamide obtained in Reference Example 2 and, instead of benzoyl-chloride, 3-ethoxybenzoyl chloride which was separately prepared by a conventional method, to produce 2.16 g of 1-benzyl-4-(3-ethoxybenzoylamino)-5-imidazolecarboxamide (yield 55%).

A cyclization reaction was carried out for 7 hours using 1.82 g (5 mmol) of the amide obtained above under the same conditions as in Example 1 to produce crude crystals, which were purified by suspension in hot methanol to obtain 1.52 g of 7-benzyl-2-(3-ethoxyphenyl)hypoxanthine (yield 88%).

$^1$H-NMR (300 MHz, DMSO-$d_6$, δ ppm):

1.36 (3H, t, J=7.2 Hz, methyl of ethoxy group), 4.12 (2H, q, J=7.2 Hz, methylene of ethoxy group), 5.58 (2H, s, methylene of benzyl group), 7.06–7.08 (1H, m, 4 position of 3-ethoxyphenyl), 7.28–7.42 (6H, m, aromatic of benzyl group (5H), 5 position of 3-methoxy phenyl), 7.61–7.66 (2H, m, 2 and 6 positions of 3-ethoxyphenyl), 8.41 (1H, s, 8 position of purine skeleton), 12.24 (1H, 1 r. s, NH)

TOF-MS: 347 for $C_{20}H_{19}N_4O_2$ (M+H)

HPLC: Purity: 97%, Retention time: 17.89 minutes (the same conditions as in Example 1)

EXAMPLE 46

7-Benzyl-2-(3-butoxyphenyl) hypoxanthine

A reaction and a post-treatment were carried out following the conditions of Example 1, using 1.08 g (5 mmol)of 4-amino-1-benzyl-5-imidazolecarboxamide obtained in Reference Example 2 and, instead of benzoyl chloride, 3-butoxybenzoyl chloride which was separately prepared by a conventional method, to produce crude crystals. The crude crystals were purified by suspension in hot methanol to obtain 0.93 g of 1-benzyl-4-(3-butoxybenzoylamino)-5-imidazole carboxamide (yield 47%).

A cyclization reaction was carried out for 7 hours using 0.90 g (2.3 mmol) of the amide obtained above under the same conditions as in Example 1 to produce crude crystals, which were purified by suspension in hot methanol to obtain 0.74 g of 7-benzyl-2-(3-butoxyphenyl)hypoxanthine (yield 87%).

$^1$H-NMR (300 MHz, DMSO-$d_6$, δ ppm):

0.95 (3H, t, J=7.2 Hz, methyl of butoxy group), 1.48 (2H, m, methylene of butoxy group), 1.73 (2H, tt, J=7.4 Hz, 6.2 Hz, methylene of butoxy group), 4.06 (2H, q, J=6.2 Hz, methylene of butoxy group), 5.58 (2H, s, methylene of benzyl group), 7.06–7.09 (1H, m, 4 position of 3-butoxyphenyl), 7.28–7.41 (6H, m, aromatic of benzyl group (5H), 5 position of 3-butoxyphenyl), 7.62–7.66 (2H, m, 2 and 6 positions of 3-butoxyphenyl), 8.41 (1H, s, 8 position of purine skeleton), 12.45 (1H, br. s, NH)

TOF-MS: 375 for $C_{22}H_{23}N_4O_2$ (M+H)

HPLC: Purity: 95%, Retention time: 22.89 minutes (the same conditions as in Example 1)

EXAMPLE 47

7-Benzyl-2-(3-hexyloxyphenyl) hypxanthine

A reaction and a post-treatment were carried out following the conditions of Example 1, using 1.73 g (8 mmol) of 4-amino-1-benzyl-5-imidazolecarboxamide obtained in Reference Example 2 and, instead of benzoyl chloride, 3-hexyloxybenzoyl chloride which was separately prepared by a conventional method, to produce crude crystals. The crude crystals were purified by suspension in hot methanol to obtain 2 g of 1-benzyl-4-(3-hexyloxybenzoylamino)-5-imidazolecarboxamide (yield 59%).

A cyclization reaction was carried out for 7 hours using 1.84 g (4.5 mmol) of the amide obtained above under the same conditions as in Example 1 to produce crude crystals, which were purified by suspension in hot methanol to obtain 0.63 g of 7-benzyl-2-(3-hexyloxyphenyl)hypoxanthine (yield 35%).

$^1$H-NMR (300 MHz, DMSO-$d_6$, δ ppm):

0.88 (3H, t, J=7 Hz, methyl of hexyloxy group), 1.31–1.46 (6H, m, methylenes of hexyloxy group), 1.73 (2H, m, methylene of hexyloxy group), 4.05 (2H, q, J=6.6 Hz, methylene of hexyloxy group), 5.58 (2H, s, methylene of benzyl group), 7.06–7.08 (1H, m, 4 position of 3-hexyloxyphenyl), 7.28–7.41 (6H, m, aromatic of benzyl group (5H), 5 position of 3-hexyloxyphenyl), 7.62–7.66 (2H, m, 2 and 6 positions of 3-hexyloxy phenyl), 8.41 (1H, s, 8 position of purine skeleton), 12.45 (1H, br. s, NH)

TOF-MS: 403 for $C_{24}H_{27}N_4O_2$ (M+H)

HPLC: Purity: 97%, Retention time: 27.08 minutes (the same conditions as in Example 1)

EXAMPLE 48

7-Benzyl-2-aminomethylhypoxanthine

A reaction and a post-treatment were carried out following the conditions of Example 17, using 2.9 g (13.4 mmol)

of 4-amino-1-benzyl-5-imidazolecarboxamide obtained in Reference Example 2 and, instead of 3-pyridylacetic acid hydrochloride, 2-t-butoxycarbonylaminoacetic acid. The reaction product was purified by silica gel column chromatography and crystallization from a mixed solvent of ethyl acetate and hexane to obtain 4.28 g of 1-benzyl-4-(3-t-butoxycarbonylaminoacetylamino)-5-imidazole carboxamide (yield 86%).

A cyclization reaction was carried out under the same conditions as in Example 1 for 3 hours using 4.28 g (11.46 mmol) of the amide obtained above. The resulting product was post-treated and purified by suspension in hot methanol to obtain 3.2 g of 7-benzyl-2-(2-t-butoxycarbonylaminomethyl)hypoxanthine (yield 79%).

2 g (5.62 mmol) of the resulting hypoxanthine derivative was dissolved in 50 ml of dioxane containing 4 N hydrogen chloride and the solution was stirred for 1.5 hours at 0° C. After concentration under vacuum, the residue was recrystallized from ether to obtain 2.03 g 7-benzyl-2-aminomethylhypoxanthine hydrochloride.

$^1$H-NMR (300 MHz, DMSO-d$_6$, δ ppm):

4.04–4.06 (2H, m, methylene of aminomethyl group), 5.56 (2H, s, methylene of benzyl group), 7.27–7.34 (5H, m, aromatic of benzyl group), 8.47 (1H, s, 8 position of purine skeleton), 8.52 (2H, br. s, amino group), 12.67 (1H, br. s, NH)

TOF-MS: 256 for $C_{13}H_{14}N_5O$ (M+H)

HPLC: Purity: 98%, Retention time: 12.66 minutes (the same conditions as in Example 1)

EXAMPLE 49

7-Benzyl-2-(3-aminopropyl)hypoxanthine

A reaction and a post-treatment were carried out following the conditions of Example 17, using 2.38 g (11 mmol) of 4-amino-1-benzyl-5-imidazolecarboxamide obtained in Reference Example 2 and, instead of 3-pyridylacetic acid hydrochloride, 4-t-butoxycarbonylaminobutanoic acid to obtain 3.88 g of 1-benzyl-4-(4-t-butoxycarbonylaminobutanoylamino)-5-imidazolecarboxamide (yield 88%).

A cyclization reaction was carried out under the same conditions as in Example 1 for 2 hours using 3.88 g (9.66 mmol) of the amide obtained above. The resulting product was post-treated and purified by suspension in hot methanol to obtain 3 g of 7-benzyl-2-(3-t-butoxycarbonylaminopropyl) hypoxanthine was produced (yield 81%).

2 g (5.21 mmol) of the resulting hypoxanthine derivative was dissolved in 50 ml of dioxane containing 4 N hydrogen chloride and the solution was stirred for 1.5 hours at 0° C. After concentration under vacuum, the residue was recrystallized from ether to obtain 2.15 g of 7-benzyl-2-(3-aminopropyl)hypoxanthine hydrochloride.

$^1$H-NMR (300 MHz, DMSO-d$_6$, δ ppm):

2.00 (2H, tt, J=7.5 Hz, 7.0 Hz, central methylene of aminopropyl group), 2.74 (2H, t, J=7.0 Hz, hypoxanthine side methylene of aminopropyl group), 2.81–2.88 (2H, m, amino group side methylene of aminopropyl group), 5.58 (2H, s, methylene of benzyl group), 7.27–7.39 (5H, m, aromatic of benzyl group), 8.10 (2H, br. s, amino group), 8.75 (1H, s, 8 position of purine skeleton), 12.58 (1H, br. s, NH)

TOF-MS: 284 for $C_{15}H_{18}N_5O$ (M+H)

HPLC: Purity: 97%, Retention time: 12.34 minutes (the same conditions as in Example 1)

EXAMPLE 50

7-Benzyl-2-methylaminomethylhypoxanthine

A reaction and a post-treatment were carried out following the conditions of Example 17, using 2.92 g (13.5 mmol) of 4-amino-1-benzyl-5-imidazolecarboxamide obtained in Reference Example 2 and, instead of 3-pyridylacetic acid hydrochloride, N-t-butoxycarbonyl-N-methylaminoacetic acid. The reaction product was purified by silica gel column chromatography and crystallization from a mixed solvent of ethyl acetate and hexane to obtain 4.71 g of 1-benzyl-4-(N-t-butoxycarbonyl-N-methylaminoacetylamino)-5-imidazole carboxamide (yield 90%).

A cyclization reaction was carried out under the same conditions as in Example 1 for 3.5 hours using 4.71 g (12.2 mmol) of the amide obtained above. The resulting product was post-treated to obtain 3.79 g of 7-benzyl-2-(N-t-butoxycarbonyl-N-methylaminomethyl)hypoxanthine (yield 84%).

2 g (5.41 mmol) of the resulting hypoxanthine derivative was dissolved in 50 ml of dioxane containing 4 N hydrogen chloride and the solution was stirred for 2 hours at 0° C. After concentration under vacuum, the residue was recrystallized from ether to obtain 2.24 g of 7-benzyl-2-methylaminomethylhypoxanthine hydrochloride.

$^1$H-NMR (300 MHz, DMSO-d$_6$, δ ppm):

2.64 (3H, d, J=5.1 Hz, methyl of methylaminomethyl group), 4.16–4.19 (2H, m, methylene of methylaminomethyl group), 5.57 (2H, s, methylene of benzyl group), 7.25–7.35 (5H, m, aromatic of benzyl group), 8.51 (1H, s, 8 position of purine skeleton), 9.40 (1H, m, NH of methylaminomethyl group), 12.67 (1H, br. s, NH)

TOF-MS: 270 for $C_{14}H_{16}N_5O$ (M+H)

HPLC: Purity: 100%, Retention time: 13.21 minutes (the same conditions as in Example 1)

EXAMPLE 51

7-(3-Chlorobenzyl-2-phenylhypoxanthine

An N-alkylation reaction, acid hydrolysis, and neutralization were carried out following the conditions of Reference Example 2 using 2.00 g (9.33 mmol) of 4-benzylideneamino-5-imidazolecarboxamide obtained in Reference Example 1 and, instead of benzyl chloride, 3-chloro benzyl chloride to obtain 1.80 g of 4-amino-1-(3-chlorobenzyl)-5-imidazolecarboxamide (yield 77%).

1.20 g (4.79 mmol) of the resulting amine was reacted under the same conditions as in Example 22 and post-treated to obtain 1.21 g of 4-benzoylamino-1-(3-chlorobenzyl)-5-imidazolecarboxamide (yield 71%).

A cyclization reaction was carried out under the same conditions as in Example 1 for 8 hours using 1.21 g (3.41 mmol) of the amide obtained above. The resulting product was post-treated to obtain 1.13 g of 7-(3-chlorobenzyl)-2-phenylhypoxanthine (yield 98%).

¹H-NMR (300 MHz, DMSO-d$_6$, δ ppm):

5.59 (2H, s, methylene of 3-chlorobenzyl group), 7.30–7.54 (7H, m, 3, 4and 5 positions of phenyl group, aromatic of 3-chlorobenzyl group), 8.07 (2H, dd, J=7.5 Hz, 1.8 Hz, 2 and 6 positions of phenyl group), 8.45 (1H, s, 8 position of purine skeleton), 12.51 (1H, s, NH)

TOF-MS: 337 for $C_{18}H_{14}ClN_4O$ (M+H)

HPLC: Purity: 99.0%, Retention time: 19.4 minutes (the same conditions as in Example 1)

EXAMPLE 52

7-(4-Chlorobenzyl)-2-phenylhypoxanthine

An N-alkylation reaction, acid hydrolysis, and neutralization were carried out following the conditions of Reference Example 2 using 2.00 g (9.33 mmol) of 4-benzylideneamino-5-imidazolecarboxamide obtained in Reference Example 1 and, instead of benzyl chloride, 4-chloro benzyl chloride to obtain 1.61 g of 4-amino-1-(4-chlorobenzyl)-5-imidazolecarboxamide (yield 69%).

1.20 g (4.79 mmol) of the resulting amine was reacted under the same conditions as in Example 22 and post-treated to obtain 1.27 g of 4-benzoylamino-1-(4-chlorobenzyl)-5-imidazolecarboxamide (yield 75%).

A cyclization reaction was carried out under the same conditions as in Example 1 for 17 hours using 1.27 g (3.58 mmol) of the amide obtained above. The resulting product was post-treated to obtain 1.05 g of 7-(4-chlorobenzyl)-2-phenylhypoxanthine (yield 88%).

¹H-NMR (300 MHz, DMSO-d$_6$, δ ppm):

5.58 (2H, s, methylene of 4-chlorobenzyl group), 7.41 (4H, m, aromatic of 4-chlorobenzyl group), 7.49–7.54 (3H, m, 3,4and 5 positions of phenyl group), 8.06 (2H, dd, J=8.1 Hz, 2.1 Hz, ortho position of phenyl group), 8.42 (1H, s, 8 position of purine skeleton), 12.50 (1H, br. s, NH)

TOF-MS: 337 for $C_{18}H_{14}ClN_4O$ (M+H)

HPLC: 98.7%, Retention time: 19.50 minutes (the same conditions as in Example 1)

EXAMPLE 53

7-(4-Methoxybenzyl)-2-phenylhypoxanthine

An N-alkylation reaction, acid hydrolysis, and neutralization were carried out following the conditions of Reference Example 2 using 2.00 g (9.33 mmol) of 4-benzylideneamino-5-imidazolecarboxamide obtained in Reference Example 1 and, instead of benzyl chloride, 4-methoxybenzyl chloride to obtain 2.13 g of 4-amino-1-(4-methoxybenzyl)-5-imidazolecarboxamide (yield 93%).

1.20 g (4.87 mmol)of the resulting amine was reacted under the same conditions as in Example 22 and post-treated to obtain 0.98 g of 4-benzoylamino-1-(4-methoxybenzyl)-5-imidazolecarboxamide (yield 57%).

A cyclization reaction was carried out under the same conditions as in Example 1 for 9 hours using 0.98 g (2.80 mmol) of the amide obtained above. The resulting product was post-treated to obtain 0.70 g of 7-(4-methoxybenzyl)-2-phenylhypcxanthine (yield 75%).

¹H-NMR (300 MHz, DMSO-d$_6$, δ ppm):

3.71 (3H, , methyl of 4-methoxybenzyl group), 5.50 (2H, s, methylene of 4-methoxybenzyl group), 6.90 (2H, d, J=8.7 Hz, 3 and5 positions of4-methoybenzyl group), 7.37 (2H, d, J=8.1 Hz, 2 and 6 positions of 4-methoxybenzyl group), 7.49–7.54 (3H, m, 3,4 and 5 positions of phenyl group), 8.06 (2H, m, 2 and 6 positions of phenyl group), 8.39 (1H, s, 8 position of purine skeleton), 12.48 (1H, br. s, NH)

TOF-MS: 333 for $C_{17}H_{15}N_4O_2$ (M+H)

HPLC: Purity: 97.9%, Retention time: 17.46 minutes (the same conditions as in Example 1)

EXAMPLE 54

7-Benzyl-2-(3-aminophenyl)hypoxanthine

A reaction and a post-treatment were carried out following the conditions of Example 17 using 1.73 g (8 mmol) of 4-amino-1-benzyl-5-imidazolecarboxamide obtained in Reference Example 2 and, instead of 3-pyridylacetic acid hydrochloride, 3-t-butoxycarbonylaminobenzoic acid. The reaction product was purified by silica gel column chromatography and crystallization from a mixed solvent of ethyl acetate and hexane to obtain 1.17 g of 1-benzyl-4-(3-t-butoxycarbonylaminobenzoylamino)-5-imidazolecarboxamide (yield 34%).

A cyclization reaction was carried out under the same conditions as in Example 1 for 6 hours using 1.09 g (2.5 mmol) of the amide obtained above. The resulting product was post-treated to obtain 0.90 g of 7-benzyl-2-(3-t-butoxycarbonylaminophenyl)hypoxanthine (yield 86%).

0.84 g (2 mmol) of the resulting hypoxanthine derivative was dissolved in 7.5 ml of dioxane containing 4 N hydrogen chloride and the solution was stirred for 6 hours at 0° C. After concentration under vacuum, the residue was recrystallized from ether to obtain 0.85 g of 7-benzyl-2-(3-aminophenyl)hypoxanthine hydrochloride.

¹H-NMR (300 MHz, DMSO-d$_6$, δ ppm):

5.63 (2H, s, methylene of benzyl group), 6.45 (2H, br. s, amino group of 3-aminophenyl group), 7.27–7.42 (5H, m, aromatic of benzyl group), 7.54–7.65 (2H, m, 4 and 5 positions of 3-aminophenyl group), 8.04–8.09 (2H, m, 2 and 6 positions of 3-aminophenyl group), 8.74 (1H, s, 8 position of purine skeleton), 12.91 (1H, br. s, NH)

TOF-MS: 318 for $C_{18}H_{16}N_5O$ (M+H)

HPLC: Purity: 92%, Retention time: 18.48 minutes (the same conditions as in Example 1)

EXAMPLE 55

7-Benzyl-2-(3,5-dimethyl-4-(4-morpholinoethyloxy) phenyl)hypoxanthine

A reaction and a post-treatment were carried out in the same manner as in Example 35, except for using 2.59 g (15.6 mmol) of 3,5-dimethyl-4-hydroxybenzoic acid instead of 3-hydroxybenzoic acid to obtain 1.64 g of 3,5-dimethyl-4-(4-morpholinoethyloxy)benzoic acid (yield 38%).

An amidation reaction and a post-treatment were carried out following the conditions of Example 18, using 0.97 g (4.52 mmol) of 4-amino-1-benzyl-5-imidazolecarboxamide obtained in Reference Example 2 and, instead of acetyl chloride, 3,5-dimethyl-4-(4-morpholinoethyloxy) benzoyl chloride which was separately prepared according to a conventional method to obtain 0.94 g of 1-benzyl-4-(3-5-dimethyl-4-(4-morpholinoethyl)benzoylamino)-5-imidazolecarboxamide (yield 33%).

A cyclization reaction was carried out under the same conditions as in Example 1 for 6 hours using 0.94 g (1.97 mmol) of the amide obtained above. The resulting product was post-treated to obtain 0.67 g of 7-benzyl-2-(3,5-dimethyl-4-(4-morpholinoethyloxy)phenyl)hypoxanthine (yield 74%).

$^1$H-NMR (300 MHz, CDCl$_3$, δ ppm):

2.30 (6H, s, methyls), 2.54 (4H, t, J=4.2 Hz, N-binding methylenes of morpholine), 2.75 (2H, t, J=5.7 Hz, N-binding methylene of morpholinoethyloxy group), 3.73 (4H, t, J=4.2 Hz, O-binding methylenes of morpholine), 3.84 (2H, t, J=5.7 Hz, O-binding methylene of morpholinoethyloxy group), 5.59 (2H, s, methylene of benzyl group), 7.30–7.34 (5H, m, aromatic of benzyl group), 7.85–7.86 (3H, m, 8 position of purine skeleton, 2 and 6 positions of 3, 5-dimethyl-4-(4-morpholinoethyloxy) phenyl group), 11.54 (1H, br. s, NH)

TOF-MS: 460 calculated for $C_{26}H_{30}N_5O_3$ (M+H)

HPLC: Purity: 96%, Retention time: 15.63 minutes (the same conditions as in Example 1)

EXAMPLE 56

7-(2-Phenylethyl)-2-phenylhypoxanthine

An N-alkylation reaction, acid hydrolysis, and neutralization were carried out following the conditions of Reference Example 2, using 2.00 g (9.33 mmol) of 4-benzylideneamino-5-imidazolecarboxamide obtained in Reference Example 1 and, instead of benzyl chloride, 2-phenylethyl bromide to obtain 1.25 g of 4-amino-1-(2-phenylethyl)-5-imidazolecarboxamide (yield 58%).

1.20 g (5.21 mmol) of the resulting amine was reacted under the same conditions as in Example 22 and post-treated to obtain crude 4-benzoylamino-1-(2-phenylethyl)-5-imidazolecarboxamide.

The resulting crude amide was cyclized for 8.5 hours following the conditions of Example 1 and post-treated to obtain 0.90 g of 7-(2-phenylethyl)-2-phenylhypoxanthine (yield 55%, 2 steps).

$^1$H-NMR (300 MHz, DMSO-d$_6$, δ ppm):

3.17 (2H, t, J=6.9 Hz, methylene of phenethyl group), 4.58 (2H, t, J=6.9 Hz, N-binding methylene of phenethyl group), 7.12–7.30 (5H, m, aromatic of phenethyl group), 7.48–7.75 (3H, m, 3, 4 and 5 positions of phenyl group), 7.99 (1H, s, 8 position of purine skeleton), 8.08 (2H, dd, J=7.5 Hz, 1.5 Hz, 2 and 6 positions of phenyl group), 12.50 (1H, br. s, NH)

TOF-MS: 317 for $C_{17}H_{15}N_4O$ (M+H)

HPLC: 99.2%, Retention time: 18.11 minutes (the same conditions as in Example 1)

EXAMPLE 57

7-(4-t-Butylbenzyl)-2-phenylhypoxanthine

An N-alkylation reaction, acid hydrolysis, and neutralization were carried out following the conditions of Reference Example 2, using 2.00 g (9.33 mmol) of 4-benzylideneamino-5-imidazolecarboxamide obtained in Reference Example 1 and, instead of benzyl chloride, 4-t-butyl benzyl bromide to obtain 0.90 g of 4-amino-1-(4-t-butylbenzyl)-5-imidazole carboxamide (yield 36%).

0.81 g (2.97 mmol) of the resulting amine was reacted under the same conditions as in Example 22 and post-treated to obtain 0.87 g 4-benzoylamino-1-(4-t-butylbenzyl)-5-imidazole carboxamide (yield 78%).

0.87 g (2.31 mmol) of the resulting amide was cyclized for 9 hours following the conditions of Example 1 and post-treated to obtain 0.56 g of 7-(4-t-butylbenzyl)-2-phenylhypoxanthine (yield 67%).

$^1$H-NMR (300 MHz, DMSO-d$_6$, δ ppm):

1.24 (9H, s, t-butyl group), 5.55 (2H, s, methylene of t-butylbenzyl group), 7.31 (2H, d, J=8.7 Hz, aromatic of t-butylbenzyl group), 7.36 (2H, d, J=8.7 Hz, aromatic of t-butylbenzyl group), 7.52 (3H, m, 3, 4 and 5 positions of phenyl group), 8.06 (2H, d, J=7.2 Hz, 2 and 6 positions of phenyl group), 8.40 (1H, s, 8 position of purine skeleton), 12.46 (1H, br. s, NH)

TOF-MS: 359 for $C_{22}H_{23}N_4O$ (M+H)

HPLC: Purity: 98.8%, Retention time: 22.48 minutes (the same conditions as in Example 1)

EXAMPLE 58

7-(4-Fluorobenzyl)-2-phenylhypoxanthine

An N-alkylation reaction, acid hydrolysis, and neutralization were carried out following the conditions of Reference Example 2, using 2.00 g (9.33 mmol) of 4-benzylideneamino-5-imidazolecarboxamide obtained in Reference Example 1 and, instead of benzyl chloride, 4-fluorobenzyl chloride to obtain 1.61 g of 4-amino-1-(4-fluorobenzyl)-5-imidazolecarboxamide (yield 73%).

1.50 g (6.40 mmol) of the resulting amine was reacted under the same conditions as in Example 22 and post-treated to obtain 1.23 g of 4-benzoylamino-1-(4-fluorobenzyl)-5-imidazole carboxamide (yield 57%), 1.39 g (3.58 mmol) of the resulting amide was cyclized for 8 hours following the conditions of Example 1 and post-treated to obtain crude crystals, which were recrystallized twice from ethanol to obtain 0.66 g of 7-(4-fluorobenzyl)-2-phenylhypoxanthine (yield 73%).

$^1$H-NMR (300 MHz, DMSO-d$_6$, δ ppm):

5.57 (2H, s, methylene of 4-fluorobenzyl group), 7.19 (2H, t, J=9.0 Hz, 3 and 5 positions of 4-fluorobenzyl group), 7.42–7.53 (5H, m, 2 and 6 positions of 4-fluorobenzyl group, 3,4and 5 positions of phenyl group), 8.06 (2H, dd, J=7.8 Hz, 1.5 Hz, 2 and 6 positions of phenyl group), 8.42 (1H, s, 8 position of purine skeleton), 12.49 (1H, br. s, NH)

TOF-MS: 321 for $C_{18}H_{14}FN_4O$ (M+H)

HPLC: Purity: 97.5%, Retention time: 18.12 minutes (the same conditions as in Example 1)

EXAMPLE 59

7-Benzyl-2-(4-aminophenyl)hypoxanthine

A reaction and a post-treatment were carried out following the conditions of Example 19, using 1.73 g (8 mmol) of 4-amino-1-benzyl-5-imidazolecarboxamide obtained in Reference Example 2 and, instead of cyclopentylacetic acid, 4-t-butoxycarbonylaminobenzoic acid. The reaction product was purified by silica gel column chromatography and crystallization from a mixed solvent of ethyl acetate and hexane to obtain 0.69 g of 1-benzyl-4-(4-t-butoxycarbonylaminobenzoylamino)-5-imidazole carboxamide (yield 20%).

A cyclization reaction was carried out under the same conditions as in Example 1 for 7 hours using 0.69 g (1.58 mmol) of the amide obtained above. The resulting product was post-treated to obtain 0.55 g of 7-benzyl-2-(4-t-butoxycarbonylaminophenyl)hypoxanthine (yield 83%).

0.55 g (1.32 mmol) of the resulting hypoxanthine derivative was dissolved in 10 ml of dioxane containing 4 N hydrogen chloride, and the solution was stirred overnight at 0° C. After concentration under vacuum, the residue was recrystallized from ether to 0.27 g of 7-benzyl-2-(4-aminophenyl)hypoxanthine hydrochloride.

$^1$H-NMR (300 MHz, DMSO-$d_6$, δ ppm):

5.55 (2H, s, methylene of benzyl group), 5.72 (2H, s, $NH_2$ of 4-aminophenyl group), 6.60 (2H, d, J=10 Hz, 3 and 5 positions of 4-aminophenyl group), 7.25–7.35 (5H, m, aromatic of benzyl group), 7.83 (2H, d, J=10 Hz, 2 and 6 positions of 4-aminophenyl group), 8.32 (1H, s, 8 position of purine skeleton), 12.00 (1H, br. s, NH)

TOF-MS: 318 for $C_{18}H_{16}N_5O$ (M+H)

HPLC: Purity: 93%, Retention time: 14.64 minute (the same conditions as in Example 1)

EXAMPLE 60

7-(2-Pyridylmethyl)-2-propylhypoxanthine

An N-alkylation reaction and acid hydrolysis were carried out following the conditions of Reference Example 2, using 3 g (14 mmol) of 4-benzylideneamino-5-imidazole carboxamide obtained in Reference Example 1 and, instead of benzyl chloride, 2-chloromethylpyridine hydrochloride to obtain 1.22 g of 4-amino-1-(2-pyridyl)methyl-5-imidazole carboxamide hydrochloride (yield 36%).

1 g (3.45 mmol) of the resulting amide hydrochloride was reacted under the same conditions as in Example 21 using butyric anhydride instead of propionic anhydride, and the product was post-treated to obtain crude 4-butanoylamino-1-(2-pyridyl)methyl-5-imidazolecarboxamide.

The crude amide was cyclized for 4 hours following the conditions of Example 1 and post-treated to obtain 0.72 g of 7-(2-pyridylmethyl)-2-propylhypoxanthine (yield 77%).

$^1$H-NMR (300 MHz, DMSO-$d_6$, δ ppm):

0.90 (3H, t, J=7.4 Hz, methyl of propyl group), 1.70 (2H, m, methylene of propyl group), 2.55 (2H, t, J=7.2 Hz, hypoxanthine side methylene of propyl group), 5.64 (2H, s, methylene of pyridylmethyl group), 7.20 (1H, d, J=8.0 Hz, 3 position of pyridyl group), 7.28 (1H, dd, J=7.2 Hz, 4.4 Hz, 5 position of pyridyl group), 7.77 (1H, dd, J=8.0 Hz, 7.2 Hz, 4 position of pyridyl group), 8.24 (1H, s, 8 position of purine skeleton), 8.48 (1H, d, J=4.4 Hz, 6 position of pyridyl group), 12.67 (1H, br. s, NH)

TOF-MS: 270 for $C_{14}H_{16}N_5O$ (M+H)

HPLC: Purity: 98%, Retention time: 11.09 minutes (the same conditions as in Example 1)

EXAMPLE 61

2-(2-Acetylaminoethyl)-7-benzylhypoxanthine 1 g (3.7 mmol) of the compound prepared in Example 44 was dissolved in 50 ml of N,N-dimethylformamide and 5 ml of distilled water, and neutralized with triethylamine while cooling with ice.

1.78 g (8.67 mmol) of N-hydroxysuccinimide acetate was added to the reaction solution and the mixture was stirred for 2 days. The reaction solution was concentrated under vacuum and the concentrate was suspended in ethyl acetate and distilled water. Insoluble components were collected by filtration. The residue was washed with distilled water and dried under vacuum to obtain 0.76 g of 2-(2-acetylaminoethyl)-7-benzylhypoxanthine (yield 66%).

$^1$H-NMR (300 MHz, DMSO-$d_6$, δ ppm):

1.76 (3H, s, acetyl group), 2.72 (2H, t, J=6.6 Hz, hypoxanthine side methylene of acetylaminoethyl group), 3.42 (2H, m, amino group side methylene of acetylaminoethyl group), 5.53 (2H, s, methylene of benzyl group), 7.27–7.34 (5H, m, aromatic of benzyl group), 7.91 (1H, t, J=6.3 Hz, NH of amino group), 8.33 (1H, s, 8 position of purine skeleton), 12.17 (m, br. s, NH)

TOF-MS: 312 for $C_{16}H_{18}N_5O_2$ (M+H)

HPLC: Purity: 96%, Retention time: 13.62 minutes (the same conditions as in Example 1)

EXAMPLE 62

7-Benzyl-2-(1-methylethyl)hypoxanthine 3.23 g (14.59 mmol) of 4-amino-1-benzyl-5-imidazole carboxamide which was prepared in the Reference Example 2 was dissolved in 50 ml of dry pyridine, and 2 ml of iso-butyryl chloride was added to the solution while cooling with ice, followed by stirring at room temperature overnight. After removing the solvent by evaporation, saturated sodium bicarbonate solution was added to obtain the precipitate, which was separated by filtration. White solid precipitate thus obtained was washed with water and ethanol, and dried under reduced pressure to obtain 2.69 g of crude amide.

A cyclization reaction was carried out using the resulting crude amide for 7.5 hours under the same conditions as in Example 1. 1.83 g of 7-benzyl-2-(1-methylethyl) hypoxanthine was obtained by a post-treatment of the cyclized product. Yield 47% (2 steps).

$^1$H-NMR (300 MHz, DMSO-d$_6$, δ ppm):

1.22 (6H, d, J=6.3 Hz, methyls of isopropyl group), 2.90 (1H, sept, J=6.6 Hz, methine of isopropyl group), 5.53 (2H, s, methylene of benzyl group), 7.26–7.35 (5H, m, aromatic of benzyl group), 8.33 (1H, s, 8 position of purine skeleton), 12.10 (1H, br. s, NH)

TOF-MS: 269 for $C_{15}H_{17}N_4O$ (M+H)

HPLC: Purity: 99.0%, Retention time: 15.85 minutes (the same conditions as in Example 1)

EXAMPLE 63

7-(4-Pyridylmethyl)-2-propylhypoxanthine

An N-alkylation reaction and acid hydrolysis were carried out following the conditions of Reference Example 2, using 3 g (14 mmol) of 4-benzylideneamino-5-imidazole carboxamide obtained in Reference Example 1 and, instead of benzyl chloride, 4-chloromethylpyridine hydrochloride to obtain 1.67 g of 4-amino-1-(4-pyridyl)methyl-5-imidazole carboxamide hydrochloride (yield 49%).

1 g (3.45 mmol) of the resulting amine hydrochloride was reacted under the same conditions as in Example 21 using butyric anhydride instead of propionic anhydride, and post-treated to obtain crude 4-butanoylamino-1-(4-pyridyl)methyl-5-imidazole carboxamide.

The crude amide was cyclized for 8 hours following the conditions of Example 1 and post-treated to obtain 0.36 g of 7-(4-pyridylmethyl)-2-propylhypoxanthine. Yield 21% (2 steps).

$^1$H-NMR (300 MHz, DMSO-d$_6$, δ ppm):

0.90 (3H, t, J=7.5 Hz, methyl of propyl group), 1.70 (2H, m, methylene of propyl group), 2.56 (2H, t, J=7.2 Hz, hypoxanthine side methylene of propyl group), 5.58 (2H, s, methylene of pyridylmethyl group), 7.18 (2H, d, J=5.9 Hz, 3 and 5 positions of pyridyl group), 8.33 (1H, s, 8 position of purine skeleton), 8.51 (2H, d, J=5.9 Hz, 2 and 6 positions of pyridyl group), 12.67 (1H, br. s, NH)

TOF-MS: 270 for $C_{14}H_{16}N_5O$ (M+H)

HPLC: Purity: 98%, Retention time: 11.09 minute (the same conditions as in Example 1)

EXAMPLE 64

7-(2,4-Dichlorobenzyl)-2-phenylhypoxanthine

An N-alkylation reaction, acid hydrolysis, and neutralization were carried out following the conditions of Reference Example 2, using 2.00 g (9.33 mmol) of 4-benzylideneamino-5-imidazolecarboxamide obtained in Reference Example 1 and, instead of benzyl chloride, 2,4-dichlorobenzyl chloride to obtain 1.92 g of 4-amino-1-(2,4-dichlorobenzyl)-5-imidazolecarboxamide (yield 73%).

1.20 g (4.21 mmol) of the resulting amine was reacted under the same conditions as in Example 22 and post-treated to obtain 1.39 g of 4-benzoylamino-1-(2,4-dichlorobenzyl)-5-imidazolecarboxamide (yield 85%).

1.39 g (3.58 mmol) of the resulting amide was cyclized for 17 hours following the conditions of Example 1 and post-treated to obtain crude crystals, which were recrystallized twice from ethanol to obtain 0.92 g of 7-(2,4-dichlorobenzyl)-2-phenylhypoxanthine (yield 70%).

$^1$H-NMR (300 MHz, DMSO-d$_6$, δ ppm), 5.68 (2H, s, methylene of benzyl group), 7.00 (1H, d, J=9.0 Hz, 6 position of benzyl group), 7.39 (1H, dd, J=8.7 Hz, 1.8 Hz, 5 position of benzyl group), 7.50–7.54 (3H, m, 3, 4and 5 positions of phenyl group), 7.70 (1H, d, J=1.5 Hz, 3 position of benzyl group), 8.06 (2H, dd, J=8.1 Hz, 2.1 Hz, 2 and 6 positions of phenyl group), 8.31 (1H, s, 8 position of purine skeleton), 12.49 (1H, br. s, NH)

TOF-MS: 371 for $C_{18}H_{13}Cl_2N_4O$ (M+H)

HPLC: Purity: 93.9%, Retention time: 20.96 minutes (the same conditions as in Example 1)

EXAMPLE 65

7-Propyl-2-phenylhypoxanthine

An N-alkylation reaction, acid hydrolysis, and neutralization were carried out following the conditions of Reference Example 2, using 2.01 g (9.38 mmol)of 4-benzylideneamino-5-imidazolecarboxamide obtained in Reference Example 1 and, instead of benzyl chloride, 1-iodopropane to obtain 0.82 g of 4-amino-1-propyl-5-imidazole carboxamide (yield 53%).

0.82 g (4.87 mmol)of the resulting amine was reacted under the same conditions as in Example 22 and post-treated to obtain crude amide.

The crude amide thus obtained was cyclized for 8.5 hours following the conditions of Example 1 and post-treated to obtain crude crystals, which were recrystallized from ethanol-hexane mixed solvent to obtain 0.42 g of 7-propyl-2-phenylhypoxanthine (2 steps, yield 34%).

$^1$H-NMR (300 MHz, DMSO-d$_6$, δ ppm):

0.85 (3H, t, J=7.2 Hz, terminus methyl of propyl group), 1.86 (2H, m, methylene of propyl group), 4.30 (2H, t, J=6.9 Hz, N-bonding methylene of propyl group), 7.46–7.75 (3H, m, 3, 4 and 5 positions of phenyl group), 8.08 (1H, s, 8 position of purine skeleton), 8.25 (2H, dd, J=8.1 Hz, 2.4 Hz, 2 and 6 positions of phenyl group)

12.46 (1H, br. s, NH)

TOF-MS: 255 for $C_{14}H_{15}N_4O$ (M+H)

HPLC: Purity: 98.8%, Retention time: 14.49 minutes (the same conditions as in Example 1)

EXAMPLE 66

7-Butyl-2-phenylhypoxanthine

An N-alkylation reaction, acid hydrolysis, and neutralization were carried out following the conditions of Reference Example 2, using 2.01 g (9.38 mmol) of 4-benzylideneamino-5-imidazolecarboxamide obtained in Reference Example 1 and, instead of benzyl chloride, 1 iodobutane to obtain 1.19 g of 4-amino-1-butyl-5-imidazole carboxamide (yield 70%).

1.19 g (6.53 mmol) of the resulting amine was reacted under the same conditions as in Example 22 and post-treated to obtain crude amide.

The crude amide thus obtained was cyclized for 7.5 hours following the conditions of Example 1 and post-treated to obtain crude crystals, which were recrystallized from ethanol-hexane mixed solvent to obtain 0.76 g of 7-butyl-2-phenylhypoxanthine. Yield 43% (2 steps).

$^1$H-NMR (300 MHz, DMSO-d$_6$, δ ppm):

0.90 (3H, t, J=7.2 Hz, terminus methyl of butyl group), 1.27 (2H, m, methylene of butyl group), 1.82 (2H, m, methylene of butyl group), 4.34 (2H, t, J=6.9 Hz, N-bonding methylene of butyl group), 7.49–7.54 (3H, m, 3, 4and 5 positions of phenyl group), 8.08 (2H, dd, J=8.1 Hz, 3.0 Hz, 2 and 6 positions of phenyl group), 8.26 (1H, s, 8 position of purine skeleton), 12.45 (1H, br. s, NH)

TOF-MS: 269 for $C_{15}H_{17}N_4O$ (M+H)

HPLC: Purity: 99.6%, Retention time: 16.07 minutes (the same conditions as in Example 1)

EXAMPLE 67

7-Pentyl-2-phenylhypoxanthine

An N-alkylation reaction, acid hydrolysis, and neutralization were carried out following the conditions of Reference Example 2, using 2.00 g (9.33 mmol) of 4-benzylideneamino-5-imidazolecarboxamide obtained in Reference Example 1 and, instead of benzyl chloride, 1-iodopentane to obtain 1.05 g of 4-amino-1-pentyl-5-imidazole carboxamide (yield 58%).

1.05 g (5.35 mmol) of the resulting amine was reacted under the same conditions as in Example 22 and post-treated to obtain crude amide.

The crude amide thus obtained was cyclized for 13 hours following the conditions of Example 1 and post-treated to obtain crude crystals, which were recrystallized from ethanol-hexane mixed solvent to obtain 1.06 g of 7-pentyl-2-phenylhypoxanthine. Yield 70% (2 steps).

$^1$-H-NMR (300 MHz, DMSO-d$_6$, δ ppm) :

0.86 (3H, t, J=7.2 Hz, terminus methyl of pentyl group), 1.20–1.33 (4H, m, 2 methylenes of pentyl group), 1.84 (2H, m, methylene of pentyl group), 4.33 (2H, t, J=6.9 Hz, N-bonding methylene of pentyl group), 7.48–7.55 (3H, m, 3, 4 and 5 positions of phenyl group), 8.08 (2H, dd, J=7.2 Hz, 1.5 Hz, 2 and 6 positions of phenyl group), 8.26 (1H, s, 8 position of purine skeleton), 12.45 (1H, br. s, NH)

TOF-MS: 283 for $C_{16}H_{19}N_4O$ (M+H)

HPLC: Purity: 99.5%, Retention time: 17.79 minutes, (the same conditions as in Example 1)

EXAMPLE 68

7-(2-Chlorobenzyl)-2-phenylhypoxanthine

An N-alkylation reaction, acid hydrolysis, and neutralization were carried out following the conditions of Reference Example 2, using 2.00 g (9.33 mmol) of 4-benzylideneamino-5-imidazolecarboxamide obtained in Reference Example 1 and, instead of benzyl chloride, 2-chlorobenzyl chloride to obtain 2.04 g of 4-amino-1-(2-chlorobenzyl)-5-imidazole carboxamide (yield 86%).

1.01 g (4.03 mmol) of the resulting amine was reacted under the same conditions as in Example 22 and post-treated to obtain crude amide.

The crude amide thus obtained was cyclized for 16 hours following the conditions of Example 1 and post-treated to obtain crude crystals, which were recrystallized from ethanol-hexane mixed solvent to obtain 0.70 g of 7-(2-chlorobenzyl)-2-phenylhypoxanthine. Yield 52% (2 steps).

$^1$H-NMR (300 MHz, DMSO-d$_6$, δ ppm):

5.71 (2H, s, methylene of 2-chlorobenzyl group), 6.92–6.97 (1H, m, 3 position of 2-chlorobenzyl group), 7.26–7.38 (2H, m, 4 and 5 positions of 2-chlorobenzyl group), 7.46–7.54 (4H, m, 3, 4 and 5 positions of phenyl group, 6 position of 2-chlorobenzyl group), 8.08 (2H, dd, J=8.1 Hz, 2.1 Hz, 2 and 6 positions of phenyl group), 8.29 (1H, s, 8 position of purine skeleton), 12.48 (1H, br. s, NH)

TOF-MS: 338 for $C_{16}H_{14}ClN_4O$ (M+H)

HPLC: Purity: 94.7%, Retention time: 18.66 minutes (the same conditions as in Example 1)

EXAMPLE 69

2-Ethyl-7-(3,4,5-trimethoxybenzyl)hypoxanthine 1.65 g (7.7 mmol) of 4-benzylideneamino-5-imidazole carboxamide, 4.26 g (30.8 mmol) of potassium carbonate, and 3.84 g (23 mmol) of 3,4,5-trimethoxybenzyl chloride were reacted in the same manner as in Reference Example 2 to obtain 1.7 g of 4-amino-1-(3,4,5-trimethoxybenzyl)-5-imidazole carboxamide (yield 73%).

1.6 g (5.22 mmol) of the amide compound obtained, 1.1 ml (7.83 mmol) of triethylamine, and 1 ml (7.83 mmol) of propionic anhydride were reacted following the conditions of Example 21 to obtain 0.55 g of 4-propanoylamino-1-(3, 4,5-trimethoxybenzyl)-5-imidazolecarboxamide (yield 29%).

0.54 g (1.49 mmol) of the amide compound thus obtained was cyclized under the same conditions as in Example 1 to obtain 0.47 g of 7-(3,4,5-trimethoxybenzyl)-2-ethylhypoxanthine (yield 92%).

$^1$H-NMR (300 MHz, DMSO-d$_6$, δ ppm):

1.20 (3H, t, J=7.2 Hz, methyl of ethyl group), 2.60 (2H, q, J=7.2 Hz, methylene of ethyl group), 3.61 (3H, s, 4 position methoxy of benzyl group), 3.73 (6H, s, 3 and 5 position methoxy of benzyl group), 5.41 (2H, s, methylene of benzyl group), 6.85 (2H, s, 2 and 6 positions of benzyl group), 8.35 (1H, s, 8 position of purine skeleton), 12.20 (1H, br. s, NH)

TOF-MS: 345 for $C_{17}H_{21}N_4O_4$ (M+H)

HPLC: Purity: 98%, Retention time: 14.47 minute (the same conditions as in Example 1)

EXAMPLE 70

7-(3,4-Dimethoxybenzyl-2-ethylhypoxanthine

A dimethyl sulfoxide solution of 4.29 ml (30 mmol) veratryl alcohol (3,4-dimethoxybenzyl alcohol) was treated in 22.86 ml (180 mmol) trimethylsilyl chloride at room temperature for 1 hour. The resulting product was dissolved in ethyl acetate, washed with distilled water and saturated brine, and dried over anhydrous magnesium sulfate. After concentration under vacuum, the resulting residue was reacted with 2.14 g (10 mmol) of 4-benzylideneamino-5-imidazole carboxamide and 5.52 (40 mmol) of potassium carbonate in the same manner as in Reference Example 2 to obtain 1.73 g of 4-amino-1-(3,4-dimethoxybenzyl)-5-imidazolecarboxamide (yield 63%).

1.5 g (5.43 mmol) of this amide compound, 1.14 ml (8.15 mmol) of triethylamine, and 1.04 ml (8.15 mmol) of propionic anhydride were reacted in the same manner as in Example 21 to obtain 0.69 g of 4-propanoylamino-1-(3,4-dimethoxybenzyl)-5-imidazolecarboxamide (yield 38%).

0.66 g (1.99 mmol) of the resulting amino compound was cyclized following the procedure of Example 1 to obtain 0.43 g of 7-(3,4-dimethoxybenzyl)-2-ethylhypoxanthine (yield 71%).

$^1$H-NMR (300 MHz, DMSO-$d_6$, δ ppm):

1.19 (3H, t, J=7.3 Hz, methyl of ethyl group), 2.60 (2H, q, J=7.3 Hz, methylene of ethyl group), 3.72 (3H, s, methoxy of benzyl group), 3.75 (3H, s, methoxy of benzyl group), 5.42 (2H, s, methylene of benzyl group), 6.86–6.92 (2H, m, 5 and 6 positions of benzyl group), 7.15 (1H, s, 2 position of benzyl group), 8.30 (1H, s, 8 position of purine skeleton), 12.30 (1H, br. s, NH)

TOF-MS: 315 for $C_{16}H_{19}N_4O_3$ (M+H)

HPLC: Purity: 98%, Retention time: 13.91 minute (the same conditions as in Example 1)

EXAMPLE 71

7-(4-Benzyloxy-3,5-dimethylbenzyl)-2-ethylhypoxanthine 0.48 ml of dimethylsulfoxide was added to a solution of 1.49 g (6.15 mmol) of 4-benzyloxy-3,5-dimethylbenzyl alcohol in 40 ml of chlorotrimethylsilane, and the mixture was stirred at room temperature for 2 hours. The reaction solution was concentrated under vacuum. The concentrate was dissolved in ethyl acetate, washed with distilled water and saturation brine, and dried over anhydrous magnesium sulfate. The residue obtained by concentrating the dry product under vacuum was dissolved in 30 ml of N,N-dimethylformamide. This solution was mixed with a suspension of 0.88 g (4.1 mmol) of 4-benzylideneamino-5-imidazolecarboxamide and 2.27 g (16.4 mmol) of potassium carbonate in 30 ml of N,N-dimethylformamide. After the addition of 1.64 ml of distilled water, the mixture was heated for 10 minutes and stirred overnight. The reaction solution was concentrated under vacuum and distilled water was added to the concentrate to precipitate a crude product. The precipitate was collected by filtration using a funnel glass filter. The solid obtained was washed with distilled water and toluene, and dried under vacuum to obtain 4-benzylidene amino-1-(4-benzyloxy-3,5-dimethylbenzyl)-5-imidazole carboxamide. The resulting compound was suspended in 25 ml of 1,4-dioxane and 25 ml of 1N aqueous solution of hydrochloric acid was added, followed by stirring overnight. The reaction solution was washed with ether, added 25 ml of methanol, and neutralized with 4N aqueous solution of sodium hydroxide. The organic solvent was evaporated under vacuum and the residue was allowed to stand overnight in a refrigerator. The precipitated solid was collected by filtration, washed with distilled water, and dried to obtain 1.10 g of 4-amino-1-(4-benzyloxy-3,5-dimethylbenzyl)-5-imidazole carboxamide (yield 86%).

0.59 ml(4.28 mmol) of triethylamine and 0.55 ml (4.28 mmol) of propionic anhydride were added to the solution of 1 g (2.85 mmol) of this amide compound in 30 ml of N,N-dimethylformamide while cooling with ice, and the mixture was stirred overnight. The reaction solution was concentrated under vacuum, and 5% aqueous solution of sodium hydrogencarbonate was added to precipitate a crude product. The precipitate was collected by filtration using a funnel glass filter. The resulting solid was washed with 5% aqueous solution of sodium hydrogencarbonate and distilled water in this order, and dried under vacuum to obtain a crude product. The crude product was recrystallized from hot methanol to obtain 0.77 g of 4-propanoylamino-1-(4-benzyloxy-3,5-dimethylbenzyl)-5-imidazole carboxamide (yield 66%).

0.75 g (1.85 mmol) of the compound obtained was added to an ethanol solution (40 ml) of 0.21 g (3.7 mmol) potassium hydroxide, followed by refluxing for four hours. After the addition of 40 ml of distilled water, the mixture was neutralized using acetic acid. The solid was collected by filtration to obtain 0.67 g of 7-(4-benzyloxy-3,5-dimethylbenzyl)-2-ethylhypoxanthine (yield 93%)

$^1$H-NMR (270 MHz, DMSO-$d_6$, δ ppm):

1.20 (3H, t, J=7.5 Hz, methyl of ethyl group), 2.20 (6H, s, 2 methyls of N-benzyl group), 2.61 (2H, q, J=7.5 Hz, methylene of ethyl group), 4.74 (2H, s, methylene of O-benzyl group), 5.43 (2H, s, methylene of N-benzyl group), 7.07 (2H, s, 2 and 6 positions of N-benzyl group), 7.34–7.48 (5H, m, aromatic hydrogen of O-benzyl group), 8.31 (1H, s, 8 position of purine skeleton), 12.33 (1H, br. s, NH)

TOF-MS: 389 for $C_{23}H_{25}N_4O_2$ (M+H)

HPLC: Purity: 83%, Retention time:: 21.28 minutes (the same conditions as in Example 1)

EXAMPLE 72

2-Ethyl-7-(4-hydroxy-3,5-dimethylbenzyl) hypoxanthine 0.1 g of 10% palladium carbon was added to a solution of 0.57 g (1.47 mmol) of the compound prepared by the method of Example 71 in 50 ml of N,N-dimethylformamide. After the mixture was stirred overnight under a hydrogen atmosphere, palladium carbon was removed by filtration, the residue was concentrated under vacuum to obtain a crude product. The crude product was recrystallized from hot methanol to obtain 0.4 g of 2-ethyl-7-(4-hydroxy-3,5-dimethylbenzyl)hypoxanthine (yield 91%).

$^1$H-NMR (270 MHz, DMSO-$d_6$, δ ppm):

1.19 (3H, t, J=7.6 Hz, methyl of ethyl group), 2.10 (6H, s, 2 methyls of benzyl group), 2.60 (2H, q, J=7.5 Hz, methylene of ethyl group), 5.34 (2H, s, methylene of benzyl group), 6.96 (2H, s, 2 and 6 positions of benzyl group), 8.25 (1H, s, 8 position of purine skeleton), 8.28 (1H, br. s, NH), 12.33 (1H, br. s, NH)

TOF-MS: 299 for $C_{16}H_{19}N_4O_2$ (M+H)

HPLC: Purity: 91%, Retention time: 14.07 minutes (the same conditions as in Example 1)

EXAMPLE 73

2-Ethyl-7-(4-hydroxy-3,5-di-t-butylhenzyl) hypoxanthine

A reaction and post-treatment were conducted following the conditions of Example 71 using 5.40 g (13.65 mmol) of 4-benzyloxy-di-t-butylbenzyl alcohol, 80 ml of chlorotrimethylsilane, and 1.07 ml of dimethylsulfoxide, to obtain 4-benzyloxy-di-t-butylbenzyl chloride.

The benzylidation reaction in N,N-dimethylformamide-distilled water, benzylidene de-protection reaction with hydrochloric acid, and neutralization reaction of hydrochloride with sodium hydroxide were carried out in the same manner as in Example 71, using the benzyl chloride, 1.95 g (9.1 mmol) of 4-benzylideneamino-5-imidazolecarboxamide, and 5.03 g (36.4 mmol) of potassium carbonate, to obtain 2.44 g of 4-amino-1-(4-benzyloxy-3,5-di-t-butylbenzyl)-5-imidazolecarboxamide (yield 77%).

An amidation reaction and post-treatment were conducted following the conditions of Example 21, using 2.3 g (5.29 mmol) of the amide compound and 1.02 ml (7.94 mmol) of propionic anhydride to obtain 1.26 g of 4-propanoylamino-1-(4-benzyloxy-3,5-di-t-butylbenzyl)-5-imidazolecarboxamide (yield 48%).

A cyclization reaction was carried out using 1.05 g (2.14 mmol) of the amide obtained above. The resulting product was post-treated to obtain 0.98 g of 7-(4-benzyloxy-3,5-di-t-butylbenzyl)-2-ethylhypoxanthine (yield 96%).

0.2 g of 10% palladium carbon was added to a solution of 0.9 g (1.90 mmol) of the resulting hypoxanthine compound in 50 ml of methanol and the mixture was stirred overnight in a hydrogen atmosphere. Palladium carbon was removed by filtration and the residue was concentrated under vacuum to obtain 0.64 g of 2-ethyl-7-(4-hydroxy-3,5-di-t-butylbenzyl)hypoxanthine (yield 100%).

$^1$H-NMR (270 MHz, DMSO-$d_6$, $\delta$ ppm):

1.19 (3H, t, J=7.6 Hz, methyl of ethyl group), 2.10 (18H, s, 2 t-butyls of benzyl group), 2.60 (2H, q, J=7.6 Hz, methylene of ethyl group), 5.34 (2H, s, methylene of benzyl group), 6.96 (2H, s, 2 and 6 positions of benzyl group), 8.25 (1H, s, 8 position of purine skeleton), 8.28 (1H, br. s, NH), 12.33 (1H, br. s, NH)

TOF-MS: 383 for $C_{22}H_{31}N_4O_2$ (M+H)

HPLC: Purity: 95%, Retention time: 25.18 minutes (the same conditions as in Example 1)

EXAMPLE 74

2-Ethyl-7-14-hydroxybenzyl)hypoxanthine

A reaction and post-treatment were carried out following the conditions of Example 71 using 3 g (14 mmol) of 4-benzyloxybenzyl alcohol, 80 ml of chlorotrimethylsilane, 1.09 ml of dimethylsulfoxide, to obtain 4-benzyloxybenzyl chloride.

The benzylidation reaction in N,N-dimethylformamide-distilled water, benzylidene de-protection reaction with hydrochloric acid, and neutralization reaction of hydrochloride with sodium hydroxide were carried out in the same manner as in Example 71, using 4-benzyoxybenzyl chloride prepared above, 1.5 g (7 mmol) of 4-benzylideneamino-5-imidazolecarboxamide, and 3.87 g (28 mmol) of potassium carbonate, to obtain 0.6 g of 4-amino-1-(4-benzyloxybenzyl)-5-imidazolecarboxamide (yield 33%).

An amidation reaction and post-treatment were carried out following the conditions of Example 21, using 0.59 g (1.83 mmol) of the amide compound and 0.35 ml (2.75 mmol) of propionic anhydride to obtain 0.50 g of 4-propanoylamino-1-(4-benzyloxybenzyl)-5-imidazolecarboxamide (yield 72%).

A cyclization reaction was carried out for 0.49 g (1.24 mmol) of the amide obtained above. The resulting product was post-treated to obtain 0.45 g of 7-(4-benzyloxybenzyl)-2-ethylhypoxanthine (yield 97%).

0.2 g of 10% palladium carbon was added to a solution of 0.45 g (1.25 mmol) of the resulting hypoxanthine compound in 100 ml of methanol and the mixture was stirred overnight in a hydrogen atmosphere. Palladium carbon was removed by filtration and the residue was concentrated under vacuum to obtain 0.26 g of 2-ethyl-7-(4-hydroxybenzyl) hypoxanthine (yield 77%).

$^1$H-NMR (270 MHz, DMSO-$d_6$, $\delta$ ppm):

1.19 (3H, t, J=7.5 Hz, methyl of ethyl group), 2.60 (2H, q, J=7.5 Hz, methylene of ethyl group), 5.39 (2H, s, methylene of benzyl group), 6.70 (2H, d, J=8.5 Hz, 3 and 5 positions of benzyl group), 7.22 (2H, d, J=8.5 Hz, 2 and 6 positions of benzyl group), 8.27 (1H, s, 8 position of purine skeleton), 9.47 (1H, br. s, NH), 12.14 (1H, br. s, NH)

TOF-MS: 272 for $C_{14}H_{15}N_4O_2$ (M+H)

HPLC: Purity: 95%, Retention time: 12.24 minutes (the same conditions as in Example 1)

EXAMPLE 75

2-Propyl-7-(3-pyridylmethyl)hypoxanthine

An alkylation reaction and acid hydrolysis were carried out following the conditions of Reference Example 2, using 3.00 g (14.0 mmol) of 4-benzylideneamino-5-imidazolecarboxamide obtained as in Reference Example 1 and, instead of benzyl chloride, 3-(chloromethyl)pyridine hydrochloride to obtain 1.67 g of 4-amino-1-(3-pyridylmethyl)-5-imidazolecarboxamide dihydrochloride. Yield 42% (2 steps).

1.02 g (3.52 mmol) of the resulting amine dihydrochloride was reacted under the amidation reaction conditions of Example 21 except for using butanyric anhydride instead of propionic anhydride, and post-treated to obtain crude 4-butanoylamino-1-(3-pyridylmethyl)-5-imidazolecarboxamide. The resulting crude amide was cyclized for 14 hours following the conditions of Example 1 and post-treated to obtain 0.43 g of 2-propyl-7-(3-pyridylmethyl)hypoxanthine. Yield 45% (2 steps)

$^1$H-NMR (300 MHz, DMSO-$d_6$, $\delta$ ppm):

0.89 (3H, t, J=7.2 Hz, methyl of propyl group), 1.68 (2H, tq, J=7.5, 7.2 Hz, 2 position methylene of propyl group), 2.55 (2H, t, J=7.5 Hz, 1 position methylene of propyl group), 5.56 (2H, s, methylene of pyridylmethyl group), 7.33–7.38 (1H, m, 5 position of 3-pyridyl group), 8.39 (1H, dd, J=8.1, 1.5 Hz, 6 position of 3-pyridyl group), 8.44 (1H, s, 8 position of purine skeleton), 8.70 (1H, d, J=5.1 Hz, 4 position of 3-pyridyl group), 9.18 (1H, d, J=1.5 Hz, 2 position of 3-pyridyl group), 12.71 (1H, br. s, NH)

TOF-MS: 270 for $C_{14}H_{16}N_5O$ (M+H)

HPLC (under the same conditions as in Example 1): Purity: 98.7%, Retention time: 11.50 minutes

EXAMPLE 76

7-(4-t-Butylbenzyl)-2-ethylhypoxanthine

An amidation reaction and post-treatment were carried out following the conditions of Example 21, using 0.80 g (2.9 mmol) of 4-amino-1-(4-t-butylbenzyl)-5-imidazolecarboxamide prepared in the same manner as in Example 57 to obtain 0.87 g of 1-(4-t-butylbenzyl)-4-propanoylamino-5-imidazole carboxamide (yield 90%).

A cyclization reaction was carried out for 3 hours under the same conditions as in Example 1, using 0.87 g (2.6 mmol) of the amide obtained above. The resulting product was post-treated to obtain 0.47 g of 7-(4-t-butylbenzyl)-2-ethylhypoxanthine (yield 58%).

$^1$H-NMR (300 MHz, DMSO-$d_6$, δ ppm):

1.19 (3H, t, J=7.7 Hz, methyl of ethyl group), 1.22 (9H, s, methyl of t-butyl group), 2.59 (2H, q, J=7.7 Hz, methylene of ethyl group), 5.48 (2H, s, methylene of 4-t-butylbenzyl group), 7.25 (2H, d, J=8.0 Hz, 3 and 5 positions of 4-t-butylbenzyl group), 7.34 (2, d, J=8.0 Hz, 2 and 6 positions of 4-t-butylbenzyl group), 8.30 (1H, s, 8 position of purine skeleton), 12.10 (1H, br. s, NH)

TOF-MS: 311 for $C_{18}H_{23}N_4O$ (M+H)

HPLC (under the same conditions as in Example 1) Purity: 97%, Retention time: 19.61 minutes

EXAMPLE 77

7-Benzyl-2-(3-fluorophenyl)hypoxanthine

An amidation reaction and post-treatment were carried out under the same conditions as in Example 1, using 2.16 g (9.99 mmol) of 4-amino-1-benzyl-5-imidazolecarboxamide which was prepared in the same manner as in Reference Example 2 and 3-fluorobenzoyl chloride, instead of benzoyl chloride, to obtain 2.63 g of 1-benzyl-4-(3-fluorobenzoylamino)-5-imidazolecarboxamide (yield 78%).

A cyclization reaction was carried out for 6 hours under the same conditions as in Example 1, using 2.62 g (7.74 mmol) of the amide obtained above. The resulting product was post-treated to obtain 1.95 g of 7-benzyl-2-(3-fluorophenyl)hypoxanthine (yield 79%).

$^1$H-NMR (300 MHz, DMSO-$d_6$, δ ppm):

5.60 (2H, s, methylene of benzyl group), 7.28–7.43 (6H, m, aromatic H (5H) of benzyl group, 4 position of 3-fluorophenyl group), 7.52–7.60 (1H, m, 5 position of 3-fluorophenyl group), 7.87–7.96 (2H, m, 2 and 6 positions of 3-fluorophenyl group), 8.44 (1H, s, 8 position of purine skeleton), 12.57 (1H, br. s, NH)

TOF-MS: 321 for $C_{18}H_{14}FN_4O$ (M+H)

HPLC (under the same conditions as in Example 1) Purity: 100%, Retention time: 18.12 minutes

EXAMPLE 78

7-Benzyl-2-(4-fluorophenyl)hypoxanthine

An amidation reaction and post-treatment were carried out under the same conditions as in Example 1, using 2.16 g (9.99 mmol) of 4-amino-1-benzyl-5-imidazolecarboxamide which was prepared in the same manner as in Reference Example 2 and 4-fluorobenzoyl chloride, instead of benzoyl chloride, to obtain 2.63 g of 1-benzyl-4-(4-fluorobenzoylamino)-5-imidazolecarboxamide (yield 78%).

A cyclization reaction was carried out for 6 hours under the same conditions as in Example 1, using 2.62 g (7.74 mmol) of the amide obtained above. The resulting product was post-treated to obtain 1.89 g of 7-benzyl-2-(4-fluorophenyl)hypoxanthine (yield 76%).

$^1$H-NMR (300 MHz, DMSO-$d_6$, δ ppm):

5.59 (2H, s, methylene of benzyl group), 7.27–7.38 (7H, m, aromatic H (5H) of benzyl group, 3 and 5 positions of 4-fluorophenyl group), 8.13 (2H, dd, J=8.4, 5.4 Hz, 2 and 6 positions of 4-fluorophenyl group), 8.42 (1H, s, 8 position of purine skeleton), 12.52 (1H, br. s, NH)

TOF-MS: 321 for $C_{18}H_{14}FN_4O$ (M+H)

HPLC (under the same conditions as in Example 1) Purity: 100%, Retention time: 17.87 minutes

EXAMPLE 79

7-Benzyl-2-(3-trifluoromethylphenyl)hypoxanthine

An amidation reaction and post-treatment were carried out under the same conditions as in Example 1, using 2.16 g (9.99 mmol) of 4-amino-1-benzyl-5-imidazolecarboxamide which was prepared in the same manner as in Reference Example 2 and 3-trifluoromethylbenzoyl chloride, instead of benzoyl chloride, to obtain 3.56 g 1-benzyl-4-(3-trifluoromethylbenzoylamino)-5-imidazolecarboxamide (yield 92%).

A cyclization reaction was carried out for 10 hours under the same conditions as in Example 1, using 3.11 g (8.01 mmol) of the amide obtained above. The resulting product was post-treated to obtain 2.51 g of 7-benzyl-2-(3-trifluoromethylphenyl)hypoxanthine (yield 85%).

$^1$H-NMR (300 MHz, DMSO-$d_6$, δ ppm):

5.60 (2H, s, methylene of benzyl group), 7.27–7.39 (5H, m, aromatic H of benzyl group), 7.75 (1H, t, J=7.5 Hz, 5 position of 3-trifluoromethylphenyl group), 7.90 (1H, d, J=7.5 Hz, 4 position of 3-trifluoromethylphenyl group), 8.38 (1H, d, J=7.5 Hz, 6 position of 3-trifluoromethylphenyl group), 8.43 (1H, s, 8 position of purine skeleton), 8.44 (1H, s, 2 position of 3-trifluoromethylphenyl group), 12.74 (1H, br. s, NH)

TOF-MS: 371 for $C_{19}H_{14}F_3N_4O$ (M+H)

HPLC (under the same conditions as in Example 1) Purity: 99%, Retention time: 20.21 minutes

EXAMPLE 80

7-(2-Chlorobenzyl)-2-phenylhypoxanthine

An alkylation reaction, acid hydrolysis, and neutralization were carried out following the conditions of Reference Example 2, using 2.00 g (9.33 mmol) of 4-benzylideneamino-5-imidazolecarboxamide obtained in the same manner as in Reference Example 1 and 2-chlorobenzyl chloride, instead of benzyl chloride, to obtain 2.04 g of 4-amino-1-(2-chlorobenzyl)-5-imidazolecarboxamide (yield 86%, 3 steps).

An amidation reaction and post-treatment were carried out following the conditions of Example 22, using 1.01 g (4.03 mmol) of the amine produced above to obtain crude 4-benzoylamino-1-(2-chlorobenzyl)-5-imidazolecarboxamide.

The crude amide was cyclized for 16 hours under the same conditions as in Example 1 and post-treated to obtain 0.72 g of 7-(2-chlorobenzyl)-2-phenylhypoxanthine (yield 52%, 2 steps).

$^1$H-NMR (300 MHz, DMSO-$d_6$, δ ppm):

5.71 (2H, s, methylene of benzyl group), 6.92–6.97 (1H, m, 3 position of 2-chlorobenzyl group), 7.26–7.38 (2H, m, 4 and 5 positions of 2-chlorobenzyl group), 7.46–7.54 (4H, m, 6 position of 2-chlorobenzyl group, 3,4 and 5 positions of 2 position phenyl group), 8.08 (2H, dd, J=8.1, 2.1 Hz, 2 and 6 positions of 2 position phenyl group), 8.29 (1H, s, 8 position of purine skeleton), 12.48 (1H, br. s, NH)

TOF-MS: 337 for $C_{18}H_{14}ClN_4O$ (M+H)

HPLC (under the same conditions as in Example 1): Purity: 94.7%, Retention time: 18.66 minutes

EXAMPLE 81

7-(3-Methoxybenzyl)-2-phenylhypoxanthine

An alkylation reaction, acid hydrolysis, and neutralization were carried out following the conditions of Reference Example 2, using 2.00 g (9.33 mmol) of 4-benzylideneamino-5-imidazolecarboxamide obtained in the same manner as in Reference Example 1 and 3-methoxybenzyl chloride, instead of benzyl chloride, to obtain 2.11 g of 4-amino-1-(3-methoxybenzyl)-5-imidazolecarboxamide. Yield 91% (3 steps).

An amidation reaction and post-treatment were carried out following the conditions of Example 22, using 1.20 g (4.87 mmol) of the amine produced above to obtain 1.37 g 4-benzoylamino-1-(3-methoxybenzyl)-5-imidazolecarboxamide (yield 80%).

1.37 g (3.91 mmol) of the amide thus prepared was cyclized for 8 hours under the same conditions as in Example 1 and post-treated to obtain 0.82 g of 7-(3-methoxybenzyl)-2-phenylhypoxanthine (yield 63%).

$^1$H-NMR (300 MHz, DMSO-$d_6$, δ ppm):

3.73 (3H, s, methoxy group), 5.55 (2H, s, methylene of 3-methoxybenzyl group), 6.86 (1H, d, J=8.1 Hz, 4 position of 3-methoxybenzyl group), 6.93 (1H, d, J=7.5 Hz, 6 position of 3-methoxybenzyl group), 7.01 (1H, s, 2 position of 3-methoxybenzyl group), 7.26 (1H, t, J=7.8 Hz, 5 position of 3-methoxybenzyl group), 7.49–7.54 (3H, m, 3,4 and 5 positions of 2 position phenyl group), 8.07 (2H, dd, J=7.5, 1.5 Hz, 2 and 6 positions of 2 position phenyl group), 8.41 (1H, s, 8 position of purine skeleton), 12.49 (1H, br. s, NH)

TOF-MS: 333 for $C_{19}H_{17}N_4O_2$ (M+H)

HPLC (under the same conditions as in Example 1): Purity: 95.8%, Retention time: 17.64 minutes

EXAMPLE 82

7-(3-Fluorobenzyl)-2-phenyhypoxanthine

An alkylation reaction, acid hydrolysis, and neutralization were carried out following the conditions of Reference Example 2, using 2.00 g (9.33 mmol) of 4-benzylideneamino-5-imidazolecarboxamide obtained in the same manner as in Reference Example 1 and 3-fluorobenzyl chloride, instead of benzyl chloride, to obtain 1.98 g of 4-amino-1-(3-fluorobenzyl)-5-imidazolecarboxamide. Yield 90% (3 steps).

An amidation reaction and post-treatment were carried out following the conditions of Example 22, using 1.00 g (4.27 mmol) of the amine produced above to obtain 1.15 g of 4-benzoylamino-1-(3-fluorobenzyl)-5-imidazolecarboxamide (yield 80%).

1.15 g (3.40 mmol) of the amide thus prepared was cyclized for 8 hours under the same conditions as in Example 1 and post-treated to obtain 0.80 g of 7-(3-fluorobenzyl)-2-phenylhypoxanthine (yield 74%).

$^1$H-NMR (300 MHz, DMSO-$d_6$, δ ppm):

5.60 (2H, s, methylene of 3-fluorobenzyl group), 7.10–7.28 (3H, m, aromatic H of 3-fluorobenzyl group), 7.35–7.45 (1H, m, aromatic H of 3-fluorobenzyl group), 7.48–7.54 (3H, m, 3, 4 and 5 positions of 2 position phenyl group), 8.07 (2H, dd, J=7.5, 1.5 Hz, 2 and 6 positions of 2 position phenyl group), 8.43 (1H, s, 8 position of purine skeleton), 12.49 (1H, br. s, NH)

TOF-MS: 321 for $C_{18}H_{14}FN4O$ (M+H)

HPLC (under the same conditions as in Example 1): Purity: 99.6%, Retention time: 17.80 minutes

EXAMPLE 83

7-Ethyl-2-phenylhypoxanthine

An alkylation reaction, acid hydrolysis, and neutralization were carried out following the conditions of Reference Example 2, using 2.00 g (9.33 mmol) of 4-benzylideneamino-5-imidazolecarboxamide obtained in the same manner as in Reference Example 1 and ethyl bromide, instead of benzyl chloride, to obtain 0.89 g of 4-amino-1-ethyl-5-imidazolecarboxamide (yield 62%, 3 steps).

An amidation reaction and post-treatment were carried out following the conditions of Example 22, using 0.88 g (5.7 mmol) of the amine produced above to obtain crude 4-benzoylamino-1-ethyl-5-imidazolecarboxamide.

The crude amide thus prepared was cyclized for 17 hours under the same conditions as in Example 1 and post-treated to obtain 0.55 g of 7-ethyl-2-phenylhypoxanthine (yield 40%, 2 steps).

$^1$H-NMR (300 MHz, DMSO-$d_6$, δ ppm):

1.44 (3H, t, J=6.9 Hz, methyl of ethyl group), 4.36 (2H, q, J=6.9 Hz, methylene of ethyl group), 7.50 (3H, m, 3, 4 and 5 positions of phenyl group), 8.08 (2H, dd, J=7.5, 1.5 Hz, 2 and 6 positions of phenyl group), 8.25 (1H, s, 8 position of purine skeleton), 12.47 (1H, br. s, NH)

TOF-MS: 241 for $C_{13}H_{13}N_4O$ (M+H)

HPLC (under the same conditions as in Example 1): Purity: 98.0%, Retention time: 13.13 minutes

EXAMPLE 84

7-Benzyl-2-(N-ethylaminomethyl)hypoxanthine

An amidation reaction and post-treatment were carried out under the same conditions as in Example 17, using 10.81 g (50.5 mmol) of 4-amino-1-benzyl-5-imidazolecarboxamide which was prepared in the same manner as in Reference Example 2 and N-t-butyloxycarbonyl-N-ethylglycine, instead of 3-pyridylacetic acid hydrochloride, to obtain 13.24 g of 4-(N-t-butyloxycarbonyl-N-ethylaminoacetylamino)-1-benzyl-5-imidazolecarboxamide (yield 66%).

A cyclization reaction was carried out for 4 hours using 2.00 g (4.98 mmol) of the amide obtained above. The resulting product was post-treated to obtain 1.85 g of 7-benzyl-2-(N-t-butyloxycarbonyl-N-ethylaminomethyl)hypoxanthine (yield 96%).

0.80 g (2.1 mmol) of the carbamate thus prepared was treated with 7.9 ml of 1,4-dioxane containing 4N hydrogen chloride to obtain 0.74 g of 7-benzyl-2-(N-ethylaminomethyl)hypoxanthine hydrochloride (yield 100%).

1H-NMR (270 MHz, DMSO-$d_6$, δ ppm):

1.24 (3H, t, J=7.7 Hz, methyl of N-ethyl group), 3.05 (2H, qt, J=7.7, 6.0 Hz, methylene of N-ethyl group), 4.17 (2H, t, J=5.4 Hz, N-methylene), 5.57 (2H, s, methylene of benzyl group), 7.29–7.36 (5H, m, benzyl group), 8.49 (1H, s, 8 position of purine skeleton), 9.35 (2H, m, NH$_2$), 12.69 (1H, br. s, NH)

TOF-MS: 284 for $C_{15}H_{18}N_5O$ (M+H)

HPLC (under the same conditions as in Example 1): Purity: 99.4%, Retention time: 12.68 minutes

EXAMPLE 85

7-Benzyl-2-(2-(N-methylamino)ethyl)hypoxanthine

An amidation reaction and post-treatment were carried out under the same conditions as in Example 17, using 1.92 g (8.96 mmol) of 4-amino-1-benzyl-5-imidazolecarboxamide which was prepared in the same manner as in Reference Example 2 and 3-(N-t-butyloxycarbonyl-N-methylamino)propionic acid, instead of 3-pyridylacetic acid hydrochloride, to obtain 2.56 g of 4-(3-(N-t-butyloxycarbonyl-N-methylamino)propanoylamino)-1-benzyl-5-imidazole carboxamide (yield 72%).

A cyclization reaction was carried out for 2.5 hours using 2.00 g (4.98 mmol) of the amide obtained above. The resulting product was post-treated to obtain 1.57 g of 7-benzyl-2-(2-(N-t-butyloxycarbonyl-N-methylamino)ethyl)hypoxanthine (yield 82%).

0.80 g (2.1 mmol) of the carbamate thus prepared was treated with 7.9 ml of 1,4-dioxane containing 4N hydrogen chloride to obtain 0.74 g of 7-benzyl-2-(2-(N-methylamino)ethyl)hypoxanthine hydrochloride (yield 100%).

$^1$H-NMR (270 MHz, DMSO-$d_6$, δ ppm):

2.56 (3H, t, J=7.7 Hz, N-methyl group), 3.05 (2H, t, J=6.8 Hz, 1 position methylene of aminoethyl group), 3.30 (2H, tt, J=6.8, 5.8 Hz, 2 position methylene of aminoethyl group), 5.56 (2H, s, methylene of benzyl group), 7.25–7.36 (5H, m, benzyl group), 8.53 (1H, s, 8 position of purine skeleton), 8.86 (2H, m, NH$_2$), 12.48 (1H, br. s, NH)

TOF-MS: 284 for $C_{15}H_{18}N_5O$ (M+H)

HPLC (under the same conditions as in Example 1): Purity: 99%, Retention time: 12.84 minutes

EXAMPLE 86

7-Benzyl-2-(3-(N-methylamino)propyl) hypoxanthine

An amidation reaction and post-treatment were carried out under the same conditions as in Example 17, using 1.44 g (6.72 mmol) of 4-amino-1-benzyl-5-imidazolecarboxamide which was prepared in the same manner as in Reference Example 2 and 4-(N-t-butyloxycarbonyl-N-methylamino)butanoic acid, instead of 3-pyridylacetic acid hydrochloride, to obtain 1.86 g of 4-(4-(N-t-butyloxycarbonyl-N-methylamino)butanoylamino)-1-benzyl-5-imidazole carboxamide (yield 67%).

A cyclization reaction was carried out for 7 hours using 1.58 g (3.80 mmol) of the amide obtained above. The resulting product was post-treated to obtain 1.21 g of 7-benzyl-2-(3-(N-t-butyloxycarbonyl-N-methylamino)propyl)hypoxanthine (yield 80%).

0.80 g (2.0 mmol) of the carbamate thus prepared was treated with 7.6 ml of 1,4-dioxane containing 4N hydrogen chloride to obtain 0.74 g of 7-benzyl-2-(3-(N-methylamino)propyl)hypoxanthine hydrochloride (yield 99%).

$^1$H-NMR (270 MHz, DMSO-$d_6$, δ ppm):

2.05 (2H, tt, J=8.1, 7.3 Hz, 2position methylene of amino propyl group), 2.51 (3H, t, J=5.1 Hz, N-methyl group), 2.73 (2H, t, J=7.3 Hz, 1 position methylene of aminopropyl group), 2.94 (2H, tt, J=8.1, 5.1 Hz, 3 position methylene of aminopropyl group), 5.57 (2H, s, methylene of benzyl group), 7.28–7.39 (5H, m, benzyl group), 8.03 (1H, s, 8 position of purine skeleton),
8.39 (2H, m, $NH_2$),
12.43 (1H, br. s, NH)
TOF-MS: 297 for $C_{16}H_{20}N_5O$ (M+H)
HPLC (under the same conditions as in Example 1): Purity: 99%, Retention time:: 12.89 minutes

EXAMPLE 87

2-Ethyl-7-(4-methylbenzyl)hypoxanthine

An alkylation reaction, acid hydrolysis, and neutralization were carried out following the conditions of Reference Example 2, using 3.00 g (14.0 mmol) of 4-benzylideneamino-5-imidazolecarboxamide obtained in the same manner as in Reference Example 1 and α-chloro-p-xylene, instead of benzyl chloride, to obtain 1.40 g of 4-amino-1-(4-methylbenzyl)-5-imidazolecarboxamide (yield 61%, 3 steps).

An amidation reaction and post-treatment were carried out following the conditions of Example 21, using 0.69 g (3.00 mmol) of the amine produced above to obtain 0.65 g of 1-(4-methylbenzyl)-4-propanoylamino-5-imidazolecarboxamide (yield 76%).

0.60 g (2.1 mmol) of the amide thus prepared was cyclized for 4 hours under the same conditions as in Example 1 and post-treated to obtain 0.46 g of 2-ethyl-7-(4-methylbenzyl) hypoxanthine (yield 82%).

$^1$H-NMR (300 MHz, DMSO-$d_6$, δ ppm):
1.19 (3H, t, J=7.2 Hz, methyl of ethyl group),
2.25 (3H, s, methyl group of 4-methylbenzyl),
2.59 (2H, q, J=7.2 Hz methylene of ethyl group),
5.46 (2H, s, methylene of 4-methylbenzyl group),
7.12 (2H, d, J=8.1 Hz, 3 and 5 positions of 4-methylbenzyl group),
7.22 (2H, d, J=8.1 Hz, 2 and 6positions of4-methylbenzyl group),
8.28 (1H, s, 8 position of purine skeleton),
12.11 (1H, br. s, NH)
TOF-MS: 269 for $C_{15}H_{27}N_4O$ (M+H)
HPLC (under the same conditions as in Example 1): Purity: 92%, Retention time: 16.15 minutes

EXAMPLE 88

2-Ethyl-7-(2,4-dimethylbenzyl hypoxanthine

An alkylation reaction, acid hydrolysis, and neutralization were carried out following the conditions of Reference Example 2, using 3.00 g (14.0 mmol) of 4-benzylideneamino-5-imidazolecarboxamide obtained in the same manner as in Reference Example 1 and 2,4-dimethylbenzyl chloride, instead of benzyl chloride, to obtain 1.71 g of 4-amino-1-(2,4-dimethylbenzyl)-5-imidazolecarboxamide (yield 76%, 3 steps).

An amidation reaction and post-treatment were carried out following the conditions of Example 21, using 0.73 g (3.0 mmol) of the amine produced above to obtain 0.77 g of 1-(2,4-dimethylbenzyl)-4-propanoylamino-5-imidazole carboxamide (yield 85%).

0.60 g (2.0 mmol) of the amide thus prepared was cyclized for 4 hours under the same conditions as in Example 1 and post-treated to obtain 0.46 g of 2-ethyl-7-(2,4-dimethylbenzyl)hypoxanthine (yield 82%).

$^1$H-NMR (300 MHz, DMSO-$d_6$, δ ppm):
1.23 (3H, t, J=7.2 Hz, methyl of ethyl group),
2.25 (3H, s, methyl group of 2,4-dimethylbenzyl),
2.29 (3H, s, methyl group of 2,4-dimethylbenzyl),
2.60 (2H, q, J=7.2 Hz, methylene of ethyl group),
5.51 (2H, s, methylene of 2,4-dimethylbenzyl group),
6.68 (1H, d, J=7.2 Hz, 6 position of 2,4-dimethylbenzyl group),
6.91 (1H, d, J=7.2 Hz, 5 position of 2,4-dimethylbenzyl group),
7.01 (1H, s, 3 position of 2,4-dimethylbenzyl group),
8.08 (1H, s, 8 position of purine skeleton),
12.11 (1H, br. s, NH)
TOF-MS: 283 for $C_{16}H_{19}N_4O$ (M+H)
HPLC (under the same conditions as in Example 1): Purity: 89%, Retention time: 17.22 minutes

EXAMPLE 89

2-Ethyl-7-(2-morpholinoethyl)hypoxanthine

An alkylation reaction and acid hydrolysis were carried out following the conditions of Reference Example 2, using 2.14 g (9.99 mmol) of 4-benzylideneamino-5-imidazolecarboxamide obtained in the same manner as in Reference Example 1 and N-(2-chloroethyl)morpholine, instead of benzyl chloride, to obtain 2.59 g of 4-amino-1-(2-morpholinoethyl)-5-imidazole carboxamide dihydrochloride (yield 83%, 2 steps).

An amidation reaction and post-treatment were carried out following the conditions of Example 21, using 2.33 g (7.46 mmol) of the amine produced above to obtain crude 1-(2-morpholinoethyl)-4-propanoylamino-5-imidazolecarboxamide.

The resulting crude amide was cyclized for 14 hours under the same conditions as in Example 1 and post-treated to obtain 0.50 g of 2-ethyl-7-(2-morpholinoethyl) hypoxanthine (yield 24%, 2 steps).

$^1$H-NMR (300 MHz, $CDCl_3$, δ ppm):
1.41 (3H, t, J=7.3 Hz, methyl of ethyl group),
2.50 (4H, t, J=4.5 Hz, methylene on the N side of morpholine ring),
2.81 (2H, t, J=6.2 Hz, methylene of the morpholine ring side),
2.82 (2H, q, J=7.3 Hz, methylene of ethyl group),
3.67 (4H, t, J=4.5 Hz, methylene on the O side of morpholine ring),
4.48 (2H, t, J=6.2 Hz, methylene of the purine ring side),
7.96 (1H, s, 8 position of purine skeleton),
11.81 (1H, br. s, NH)
TOF-MS: 278 for $C_{13}H_{20}N_5O_2$ (M+H)
HPLC (under the same conditions as in Example 1): Purity: 98%, Retention time: 11.3 minutes

EXAMPLE 90

2-Ethyl-7-(2-phenylethyl)hypoxanthine

An amidation reaction and post-treatment were carried out following the conditions of Example 21 using 0.80 g (3.5 mmol) of 4-amino-1-(2-phenylethyl)-5-imidazolecarboxamide which was prepared in the same manner as in Example 56 to obtain 0.67 g of 1-(2-phenylethyl)-4-propanoylamino-5-imidazole carboxamide (yield 67%).

0.66 g (2.3 mmol) of the amide thus prepared was cyclized for 4 hours under the same conditions as in Example 1 and post-treated to obtain 0.49 g of 2-ethyl-7-(2-phenylethyl)hypoxanthine (yield 79%).

$^1$H-NMR (300 MHz, DMSO-d$_6$, δ ppm):

1.20 (3H, t, J=7.6 Hz, methyl of ethyl group), 2.61 (2H, q, J=7.6 Hz, methylene of ethyl group), 3.12 (2H, t, J=7.2 Hz, 2 position methylene of phenethyl group), 4.50 (2H, t, J=7.5 Hz, 1 position methylene of phenethyl group), 7.10–7.28 (5H, m, phenyl), 7.88 (1H, s, 8 position of purine skeleton), 12.14 (1H, br. s, NH)

TOF-MS: 269 for C$_{15}$H$_{17}$N$_4$O (M+H)

HPLC (under the same conditions as in Example 1): Purity: 99.1%, Retention time: 15.33 minutes

EXAMPLE 91

7-(3-Chlorobenzyl)-2-ethylhypoxanthine

An amidation reaction and post-treatment were carried out following the conditions of Example 21 using 0.60 g (2.4 mmol) of 4-amino-1-(3-chlorobenzyl)-5-imidazolecarboxamide which was prepared in the same manner as in Example 51 to obtain 0.67 g of 1-(3-chlorobenzyl)-4-propanoylamino-5-imidazole carboxamide (yield 92%).

0.66 g (2.2 mmol) of the amide thus prepared was cyclized for 3 hours under the same conditions as in Example 1 and post-treated to obtain 0.39 g of 7-(3-chlorobenzyl)-2-ethylhypoxanthine (yield 63%).

$^1$H-NMR (300 MHz, DMSO-d$_6$, δ ppm):

1.19 (3H, t, J=7.7 Hz, methyl of ethyl group), 2.60 (2H, q, J=7.7 Hz, methylene of ethyl group), 5.52 (2H, s, methylene of 3-chlorobenzyl group), 7.29–7.44 (4H, m, 3-chlorobenzyl group), 8.34 (1H, s, 8 position of purine skeleton), 12.16 (1H, br. s, NH)

TOF-MS: 289 for C$_{14}$H$_{14}$ClN$_4$O (M+H)

HPLC (under the same conditions as in Example 1): Purity: 92.3%, Retention time: 16.53 minutes

EXAMPLE 92

7-Benzyl-2-(3-methylphenyl)hypoxanthine

An amidation reaction and post-treatment were carried out following the conditions of Example 1, using 1.08 g (4.99 mmol) of 4-amino-1-benzyl-5-imidazolecarboxamide obtained as in Reference Example 2 and, instead of acetyl chloride, 3-methylbenzoyl chloride which was separately prepared according to a conventional method to obtain 1.21 g of 1-benzyl-4-(3-methylbenzoylamino)-5-imidazolecarboxamide (yield 72%).

A cyclization reaction was carried out under the same conditions as in Example 1 for 7 hours using 1.20 g (3.59 mmol) of the amide obtained above. The resulting product was post-treated to obtain 1.03 g of 7-benzyl-2-(3-methylphenyl)hypoxanthine (yield 90%).

$^1$H-NMR (270 MHz, DMSO-d$_6$, δ ppm):

2.39 (3H, s methyl group), 5.59 (2H, s, methylene of benzyl group), 7.29–7.43 (7H, m, aromatic H (5H) of benzyl group, 4 and 5 positions of 3-methylphenyl group), 7.87 (1H, d, J=7.3 Hz, 6 position of 3-methylphenyl group), 7.93 (1H, s, 2 position of 3-methylphenyl group), 8.42 (1H, s, 8 position of purine skeleton), 12.43 (1H, br. s, NH)

TOF-MS: 317 for C$_{19}$H$_{17}$N$_4$O (M+H)

HPLC (under the same conditions as in Example 1): Purity: 99%, Retention time: 18.46 minutes

EXAMPLE 93

7-(4-Trifluoromethylbenzyl)-2-phenylhypoxanthine

An alkylation reaction, acid hydrolysis, and neutralization were carried out following the conditions of Reference Example 2, using 1.50 g (7.00 mmol) of 4-benzylideneamino-5-imidazolecarboxamide obtained in the same manner as in Reference Example 1 and 4-trifluoromethyl benzyl bromide, instead of benzyl chloride, to obtain 1.59 g of 4-amino-1-(4-trifluoromethylbenzyl)-5-imidazole carboxamide (yield 80%, 3 steps).

An amidation reaction and post-treatment were carried out following the conditions of Example 22, using 1.59 g (5.59 mmol) of the amine produced above to obtain 1.55 g of 4-benzoylamino-1-(4-trifluoromethylbenzyl)-5-imidazole carboxamide (yield 72%).

1.55 g (3.99 mmol) of the amide thus prepared was cyclized for 22 hours under the same conditions as in Example 1 and post-treated to obtain 1.12 g of 2-phenyl-7-(4-trifluoromethylbenzyl)hypoxanthine (yield 76%).

$^1$H-NMR (270 MHz, DMSO-d$_6$, δ ppm):

5.71 (2H, s, methylene of 4-trifluoromethylbenzyl group), 7.50–7.57 (5H, m, 2 and 6 positions 4-trifluoromethylbenzyl group, 3, 4 and 5 positions of 2 position phenyl group), 7.74 (2H, d, J=7.8 Hz, 3 and 5 positions of 4-trifluoromethylbenzyl group), 8.08 (2H, dd, J=7.6, 1.6 Hz, 2 and 6 positions of 2 position phenyl group), 8.47 (1H, s, 8 position of purine skeleton), 12.53 (1H, br. s, NH)

TOF-MS: 371 for C$_{19}$H$_{14}$F$_3$N$_4$O (M+H)

HPLC (under the same conditions as in Example 1): Purity: 98.1%, Retention time: 20.15 minutes

EXAMPLE 94

7-(3-Trifluoromethylbenzyl)-2-phenylhypoxanthine

An alkylation reaction, acid hydrolysis, and neutralization were carried out following the conditions of Reference Example 2, using 1.50 g (7.00 mmol) of 4-benzylideneamino-5-imidazolecarboxamide obtained in the same manner as in Reference Example 1 and 3-trifluoromethylbenzyl chloride instead of benzyl chloride to obtain 1.57 g of 4-amino-1-(3-trifluoromethylbenzyl)-5-imidazolecarboxamide (yield 79%, 3 steps).

An amidation reaction and post-treatment were carried out following the conditions of Example 22, using 1.57 g (5.52 mmol) of the amine produced above to obtain 1.54 g of 4-benzoylamino-1-(3-trifluoromethylbenzyl)-5-imidazole carboxamide (yield 72%).

1.54 g (3.96 mmol) of the amide thus prepared was cyclized for 22 hours under the same conditions as in Example 1 and post-treated to obtain 1.13 g of 2-phenyl-7-(3-trifluoromethylbenzyl)hypoxanthine (yield 77%).

$^1$H-NMR (270 MHz, DMSO-$d_6$, δ ppm):

5.68 (2H, s, methylene of 3-trifluoromethylbenzyl group), 7.48–7.71 (6H, m, 4, 5 and 6 positions of 3-trifluoromethylbenzyl group, 3, 4 and 5 positions of 2 position phenyl group), 7.87 (1H, m, aromatic 2 position of 3-trifluoromethylbenzyl group), 8.08 (2H, dd, J=7.6, 2.2 Hz, 2 and 6 positions of 2 position phenyl group), 8.49 (1H, s, 8 position of purine skeleton), 12.55 (1H, br. s, NH)

TOF-MS: 371 for $C_{19}H_{14}F_3N_4O$ (M+H)

HPLC (under the same conditions as in Example 1): Purity: 99.0%, Retention time: 19.93 minutes

EXAMPLE 95

7-Benzyl-2-(3-(N-methylamino)phenyl) hypoxanthine

An amidation reaction and post-treatment were carried out under the same conditions as in Example 17, using 0.65 g (3.0 mmol) of 4-amino-1-benzyl-5-imidazolecarboxamide which was prepared in the same manner as in Reference Example 2 and 3-(N-t-butyloxycarbonyl-N-methylamino) benzoic acid, instead of 3-pyridylacetic acid hydrochloride, to obtain 1.09 g of 1-benzyl-4-(3-(N-t-butyloxycarbonyl-N-methylamino)benzoylamino)-5-imidazole carboxamide (yield 81%).

A cyclization reaction was carried out under the same conditions as in Example 1 for 9 hours using 1.08 g (2.40 mmol) of the amide obtained above. The resulting product was post-treated to obtain 0.77 g of 7-benzyl-2-(3-(N-t-butyloxycarbonyl-N-methylamino)phenyl)hypoxanthine (yield 74%). 0.76 g (1.8 mmol) of the carbamate thus prepared was treated with 5.3 ml of 1,4-dioxane containing 4N hydrogen chloride and neutralized to obtain 0.54 g of 7-benzyl-2-(3-(N-methylamino)phenyl)hypoxanthine (yield 93%).

$^1$H-NMR (300 MHz, DMSO-$d_6$, δ ppm):

2.74 (3H, d, J=5.1 Hz, methyl group), 5.58 (2H, s, methylene of benzyl group), 6.69 (1H, d, J=8.1 Hz, 4 position of 3-methylaminophenyl group), 7.15–7.38 (8H, m, aromatic H of benzyl group, 2, 5 and 6 positions of 3-methylaminophenyl group), 8.39 (1H, 4s, 8 position of purine skeleton), 12.30 (1H, br. s, NH)

TOF-MS: 332 for $C_{19}H_{18}N_5O$ (M+H)

HPLC (under the same conditions as in Example 1): Purity: 98%, Retention time: 14.38 minutes

EXAMPLE 96

7-(4-Fluorobenzyl)-2-(2-fluorophenyl)hypoxanthine

An amidation reaction and post-treatment were carried out under the same conditions as in Example 1, using 2.12 g (9.01 mmol) of 4-amino-i-(4-fluorobenzyl)-5-imidazole carboxamide which was prepared in the same manner as in Example 58 and 2-fluorobenzoyl chloride instead of benzoyl chloride to obtain 2.61 g of 4-(2-fluorobenzoylamino)-1-(4-fluorobenzyl)-5-imidazolecarboxamide (yield 82%).

A cyclization reaction was carried out under the same conditions as in Example 1 for 12 hours using 2.50 g (7.00 mmol) of the amide obtained above. The resulting product was post-treated to obtain 1.93 g of 7-(4-fluorobenzyl)-2-(2-fluorophenyl)hypoxanthine(yield 81%).

$^1$H-NMR (300 MHz, DMSO-$d_6$, δ ppm):

5.57 (2H, s, methylene of 4-fluorobenzyl group), 7.19 (2H, t, J=8.7 Hz, 3 and 5 positions of 4-fluorobenzyl group), 7.35 (2H, dd, J=8.6, 6.0 Hz, 2 and 6 positions of 4-fluorobenzyl group), 7.44–7.49 (2H, m, 3 and 5 positions of 2-fluorophenyl group), 7.54–7.62 (1H, m, 4 position of 2-fluorophenyl group), 7.67–7.73 (1H, m, 6 position of 2-fluorophenyl group), 8.45 (1H, s, 8 position of purine skeleton), 12.57 (1H, br. s, NH)

TOF-MS: 339 for $C_{18}H_{13}F_2N_4O$ (M+H)

HPLC (under the same conditions as in Example 1): Purity: 99%, Retention time: 17.53 minutes

EXAMPLE 97

7-(3-Chlorobenzyl)-2-(2-fluorophenyl)hypoxanthine

An amidation reaction and post-treatment were carried out under the same conditions as in Example 1, using 2.0 g (8.0 mmol) of 4-amino-i-(3-chlorobenzyl)-5-imidazolecarboxamide which was prepared in the same manner as in Example 51 and 2-fluorobenzoyl chloride instead of benzoyl chloride to obtain 2.91 g of 1-(3-chlorobenzyl)-4-(2-fluorobenzoylamino)-5-imidazolecarboxamide (yield 98%).

A cyclization reaction was carried out under the same conditions as in Example 1 for 15 hours using 2.90 g (7.78 mmol) of the amide obtained above. The resulting product was post-treated to obtain 2.59 g of 7-(3-chlorobenzyl)-2-(2-fluorophenyl)hypoxanthine (yield 94%).

$^1$H-NMR (300 MHz, DMSO-$d_6$, δ ppm):

5.59 (2H, s, methylene of 3-chlorobenzyl group), 7.31–7.43 (6H, m, 3-chlorobenzyl group, 3 and 5 positions of 2-fluorophenyl group), 7.50–7.61 (1H, m, 4 position of 2-fluorophenyl group), 7.68–7.74 (1H, m, 6 position of 2-fluorophenyl group), 8.46 (1H, s, 8 position of purine skeleton), 12.58 (1H, br. s, NH)

TOF-MS: 355 for $C_{18}H_{13}ClFN_4O$ (M+H)

HPLC (under the same conditions as in Example 1): Purity: 99%, Retention time: 18.67 minutes

EXAMPLE 98

7-(4-t-Butylbenzyl)-2-(2-fluorophenyl) hypoxanthine

An amidation reaction and post-treatment were carried out under the same conditions as in Example 1, using 1.91 g (7.01 mmol) of 4-amino-1-(4-t-butylbenzyl)-5-imidazolecarboxamide which was prepared in the same manner as in Example 57 and 2-fluorobenzoyl chloride instead of benzoyl chloride to obtain 2.47 g of 1-(4-t-butylbenzyl)-4-(2-fluorobenzoylamino)-5-imidazolecarboxamide (yield 89%).

A cyclization reaction was carried out under the same conditions as in Example 1 for 7 hours using 2.47 g (6.26 mmol) of the amide obtained above. The resulting product was post-treated to obtain 1.27 g of 7-(4-t-butylbenzyl)-2-(2-fluorophenyl)hypoxanthine (yield 54%).

$^1$H-NMR (300 MHz, DMSO-$d_6$, δ ppm):

1.24 (9H, s, methyls of t-butyl group), 5.55 (2H, s, methylene of 4-t-butylbenzyl group), 7.26–7.38 (6H, m, 3 and 5 positions of 2-fluorophenyl group, aromatic H of 4-t-butylbenzyl group), 7.54–7.59 (1H, m, 4 position of 2-fluorophenyl group), 7.67–7.72 (1H, m, 6 position of 2-fluorophenyl group), 8.44 (1H, s, 8 position of purine skeleton), 12.55 (1H, br. s, NH)

TOF-MS: 377 for $C_{22}H_{22}FN_4O$ (M+H)

HPLC (under the same conditions as in Example 1): Purity: 97%, Retention time: 21.49 minutes

EXAMPLE 99

7-(4-fluorobenzyl)-2-(3-pyridyl)hypoxanthine

An amidation reaction and post-treatment were carried out under the same conditions as in Example 19, using 1.50 g (6.38 mmol) of 4-amino-1-(4-fluorobenzyl)-5-imidazole carboxamide which was prepared in the same manner as in Example 58 and nicotinic acid instead of cyclopentylacetic acid to obtain 1.70 g of 1-(4-fluorobenzyl)-4-(3-pyridylcarbonylamino)-5-imidazolecarboxamide (yield 79%).

A cyclization reaction was carried out under the same conditions as in Example 1 for 5 hours using 1.7 g (5.0 mmol) of the amide obtained above. The resulting product was post-treated to obtain 1.07 g of 7-(4-fluorobenzyl)-2-(3-pyridyl)hypoxanthine (yield 67%).

$^1$H-NMR (270 MHz, DMSO-$d_6$, δ ppm):

5.59 (2H, s, methylene of 4-fluorobenzyl group), 7.20 (2H, t, J=8.7 Hz, 3 and 5 positions of 4-fluorobenzyl group), 7.46 (2H, d, J=8.7 Hz, 2 and 6positions of 4-fluorobenzyl group), 7.56 (1H, dd, J=7.9, 4.7 Hz, 5 position of 3-pyridyl group), 8.40 (1H, ddd, J=7.9, 1.6, 1.6 Hz, 6position of3-pyridyl group), 8.47 (1H, s, 8 position of purine skeleton), 8.72 (1H, dd, J=4.7, 1.6 Hz, 4 position of 3-pyridyl group), 9.19 (1H, d, J=1.6 Hz, 2 position of 3-pyridyl group), 12.74 (1H, br. s, NH)

TOF-MS: 322 for $C_{17}H_{13}FN_5O$ (M+H)

HPLC (under the same conditions as in Example 1): Purity: 98%, Retention time: 14.47 minutes

EXAMPLE 100

7-(3-Chlorobenzyl)-2-(3-pyridyl)hypoxanthine

An amidation reaction and post-treatment were carried out under the same conditions as in Example 19, using 1.50 g (5.98 mmol) of 4-amino-1-(3-chlorobenzyl)-5-imidazole carboxamide which was prepared in the same manner as in Example 51 and nicotinic acid instead of cyclopentylacetic acid to obtain 1.65 g of 1-(3-chlorobenzyl)-4-(3-pyridylcarbonylamino)-5-imidazolecarboxamide (yield 78%).

A cyclization reaction was carried out under the same conditions as in Example 1 for 7 hours using 1.65 g (4.64 mmol) of the amide obtained above. The resulting product was post-treated to obtain 1.07 g of 7-(3-chlorobenzyl)-2-(3-pyridyl)hypoxanthine (yield 68%).

$^1$H-NMR (270 MHz, DMSO-$d_6$, δ ppm):

5.61 (2H, s, methylene of 3-chlorobenzyl group), 7.33–7.44 (3H, m, 3-chlorobenzyl group), 7.52–7.58 (2H, m, 3-chlorobenzyl group, 5 position of 3-pyridyl group), 8.41 (1H, ddd, J=8.1, 1.8, 1.3 Hz, 6position of3-pyridyl group), 8.50 (1H, s, 8 position of purine skeleton), 8.72 (1H, dd, J=4.8, 1.3 Hz, 4 position of 3-pyridyl group), 9.20 (1H, d, J=1.8 Hz, 2 position of 3-pyridyl group), 12.76 (1H, br. s, NH)

TOF-MS: 338 for $C_{17}H_{13}ClN_5O$ (M+H)

HPLC (under the same conditions as in Example 1): Purity: 92%, Retention time: 15.56 minutes

EXAMPLE 101

7-(4-t-Butylbenzyl)-2-(3-pyridyl)hypoxanthine

An amidation reaction and post-treatment were carried out under the same conditions as in Example 19, using 1.50 g (5.51 mmol) of 4-amino-1-(4-t-butylbenzyl)-5-imidazole carboxamide which was prepared in the same manner as in Example 57 and nicotinic acid instead of cyclopentyl acetic acid to obtain 1.45 g of 1-(4-t-butylbenzyl)-4-(3-pyridylcarbonylamino)-5-imidazolecarboxamide (yield 70%).

A cyclization reaction was carried out under the same conditions as in Example 1 for 12 hours using 1.45 g (3.84 mmol) of the amide obtained above. The resulting product was post-treated to obtain 1.18 g of 7-(4-t-butylbenzyl)-2-(3-pyridyl)hypoxanthine (yield 85%).

$^1$H-NMR (270 MHz, DMSO-$d_6$, δ ppm):

1.23 (9H, s, methyls of t-butyl group), 5.56 (2H, s, methylene of t-butylbenzyl group), 7.32 (2H, d, J=8.5 Hz, 3 and 5 positions of 4-t-butylbenzyl group), 7.37 (2H, d, J=8.5 Hz, 2 and 6 positions of 4-t-butylbenzyl group), 7.54 (1H, dd, J=7.8, 4=7 Hz, 5 position of 3-pyridyl group), 8.39–8.43 (1H, m, 6 position of 3-pyridyl group), 8.43 (1H, s, 8 position of purine skeleton), 8.70 (1H, dd, J=4.7, 1.8 Hz, 4 position of 3-pyridyl group), 9.21 (1H, d, J=1.8 Hz, 2 position of 3-pyridyl group), 12.74 (1H, br. s, NH)

TOF-MS: 360 for $C_{21}H_{22}N_5O$ (M+H)

HPLC (the same conditions as in Example 1): Purity: 96%, Retention time: 18.66 minutes

EXAMPLE 102

2-Ethyl-7-(4-phenylbenzyl)hypoxanthine

An alkylation reaction, acid hydrolysis, and neutralization were carried out following the conditions of Reference Example 2, using 2.14 g (9.99 mmol) of 4-benzylideneamino-5-imidazolecarboxamide obtained in the same manner as in Reference Example 1 and 4-chloromethylbiphenyl instead of benzyl chloride to obtain 2.48 g of 4-amino-1-(4-phenylbenzyl)-5-imidazolecarboxamide (yield 85%, 3 steps)

An amidation reaction and post-treatment were carried out following the conditions of Example 21, using 1.50 g (5.13 mmol) of the amine produced above to obtain 1.71 g of 1-(4-phenylbenzyl)-4-propanoylamino-5-imidazolecarboxamide (yield 96%).

1.31 g (3.76 mmol) of the amide thus prepared was cyclized for 5 hours under the same conditions as in Example 1 and post-treated to obtain 1.21 g of 2-ethyl-7-(4-phenylbenzyl)hypoxanthine (yield 97%).

$^1$H-NMR (300 MHz, DMSO-$d_6$, δ ppm):

1.20 (3H, t, J=7.6 Hz, methyl of ethyl group),
2.60 (2H, q, J=7.2 Hz, methylene of ethyl group),
5.57 (2H, s, methylene of benzyl group),
7.29–7.63 (9H, m, biphenyl group),
8.35 (1H, s, 8 position of purine skeleton),
12.18 (1H, br. s, NH)
TOF-MS: 331 for $C_{20}H_{19}N_4O$ (M+H)
HPLC (the same conditions as in Example 1): Purity: 95%, Retention time: 19.48 minutes

EXAMPLE 103

2-(2-Fluorophenyl)-7-(2-phenylethyl)hypoxanthine

An amidation reaction and post-treatment were carried out following the conditions of Example 22 using 2.00 g (8.69 mmol) of 4-amino-1-(2-phenylethyl)-5-imidazolecarboxamide which was prepared in the same manner as in Example 56 and 2-fluorobenzoyl chloride instead of benzoyl chloride to obtain crude 4-(2-fluorobenzoylamino)-1-(2-phenylethyl)-5-imidazolecarboxamide.

The crude amide thus prepared was cyclized for 14 hours under the same conditions as in Example 1 and post-treated to obtain 0.94 g of-2-(2-fluorophenyl)-7-(2-phenylethyl)hypoxanthine (yield 32%, 2 steps).

$^1$NMR (300 MHz, DMSO-$d_6$, δ ppm):

3.17 (2H, t, J=7.4 Hz, methylene bonding to phenyl group of 2-phenylethyl),
4.58 (2H, t, J=6.9 Hz, methylene bonding to purine ring of 2-phenylethyl group),
7.14–7.41 (7H, m, aromatic H (5H) of2-phenylethyl group, aromatic H(2H) of 2-fluorophenyl group),
7.54–7.61 (1H, m, aromatic H of 2-fluorophenyl group),
7.72 (1H, t-like, J=7.7 Hz, 6 position of 2-fluorophenyl group),
8.03 (1H, s, 8 position of purine skeleton),
12.56 (1H, br. s, NH)
TOF-MS: 335 for $C_{19}H_{16}FN_4O$ (M+H)
HPLC (the same conditions as in Example 1): Purity: 98.8%, Retention time: 18.13 minutes

EXAMPLE 104

2-Ethyl-7-(3-methoxybenzyl)hypoxanthine

An amidation reaction and post-treatment were carried out following the conditions of Example 21, using 1.97 g (8.00 mmol) of 4-amino-1-(3-methoxybenzyl)-5-imidazolecarboxamide prepared in the same manner as in Example 81 to obtain 2.22 g of 1-(3-methoxybenzyl)-4-propanoylamino-5-imidazole carboxamide (yield 92%).

A cyclization reaction was carried out for 6 hours under the same conditions as in Example 1 using 2.21 g (7.31 mmol) of the amide obtained above. The resulting product was post-treated to obtain 1.57 g of 2-ethyl-7-(3-methoxybenzyl)hypoxanthine (yield 75%).

$^1$H-NMR (300 MHz, DMSO-$d_6$, δ ppm):

1.19 (3H, t, J=7.7 Hz, methyl of ethyl group),
2.60 (2H, q, J=7.7 Hz, methylene of ethyl group),
3.70 (3H, s, methoxy group),
5.48 (2H, s, methylene of 3-methoxybenzyl group),
6.85 (1H, d, J=9.0 Hz, 4 position of 3-methoxybenzyl group),
6.87 (1H, d, J=9.0 Hz, 6 position of 3-methoxybenzyl group),
6.96 (1H, s, 2 position of 3-methoxybenzyl group),
7.24 (1H, t, J=9.0 Hz, 5 positions of 3-methoxybenzyl group),
8.30 (1H, s, 8 position of purine skeleton),
11.90 (1H, br. s, NH)
TOF-MS: 285 for $C_{15}H_{17}N_4O_2$ (M+H)
HPLC (the same conditions as in Example 1): Purity: 98%, Retention time: 14.50 minutes

EXAMPLE 105

2-(2-Fluorophenyl)-7-(3-methoxybenzyl)hypoxanthine

An amidation reaction and post-treatment were carried out following the conditions of Example 1, using 1.97 g (8.00 mmol) of 4-amino-1-(3-methoxybenzyl)-5-imidazolecarboxamide prepared in the same manner as in Example 81 and 2-fluorobenzoyl chloride instead of benzoyl chloride to obtain 2.42 g of 4-(2-fluorobenzoylamino)-1-(3-methoxybenzyl)-5-imidazole carboxamide (yield 82%).

A cyclization reaction was carried out for 9 hours under the same conditions as in Example 1 using 2.41 g (6.54 mmol) of the amide obtained above. The resulting product was post-treated to obtain 2.00 g of 2-(2-fluorophenyl)-7-(3-methoxybenzyl)hypoxanthine (yield 87%).

$^1$H-NMR (300 MHz, DMSO-$d_6$, δ ppm):

3.73 (3H, s, methoxy group),
5.48 (2H, s, methylene of 3-methoxybenzyl group),
6.87 (1H, d, J=7.7 Hz, 4 position of 3-methoxybenzyl group),
6.93 (1H, d, J=7.7 Hz, 6 position of 3-methoxybenzyl group),
7.00 (1H, s, 2 position of 3-methoxybenzyl group),
7.26 (1H, t, J=7.7 Hz, 5 position of 3-methoxybenzyl group),
7.30–7.39 (2H, m, 3 and 5 positions of 2-fluorophenyl group),
7.54–7.61 (1H, m, 4 position of 2-fluorophenyl group),
7.68–7.73 (1H, m, 6 position of 2-fluorophenyl group),
8.44 The (1H, s, 8 position of purine skeleton),
12.57 (1H, br. s, NH)
TOF-MS: 351 for $C_{19}H_{16}FN_4O_2$ (M+H)
HPLC (the same conditions as in Example 1): Purity: 99%, Retention time: 17.32 minutes

EXAMPLE 106

7-(3-Methoxybenzyl)-2-(3-pyridyl)hypoxanthine

An amidation reaction and post-treatment were carried out under the same conditions as in Example 19, using 2.96 g (12.0 mmol) of 4-amino-1-(3-methoxybenzyl)-5-imidazole carboxamide which was prepared in the same manner as in Example 81 and nicotinic acid instead of cyclopentylacetic acid to obtain 2.61 g of 1-(3-methoxybenzyl)-4-(3-pyridylcarbonylamino)-5-imidazolecarboxamide (yield 62%).

A cyclization reaction was carried out under the same conditions as in Example 1 for 14 hours using 2.60 g (7.40 mmol) of the amide obtained above. The resulting product was post-treated to obtain 1.86 g of 7-(3-methoxybenzyl)-2-(3-pyridyl)hypoxanthine (yield 75%).

$^1$H-NMR (300 MHz, DMSO-d$_6$, δ ppm):

3.73 (3H, s, methoxy group), 5.56 (2H, s, methylene of 3-methoxybenzyl group), 6.86 (1H, d, J=8.1 Hz, 4 position of 3-methoxy benzyl group), 6.93 (1H, d, J=8.1 Hz, 6 position of 3-methoxybenzyl group), 7.01 (1H, s, 2 position of 3-methoxybenzyl group), 7.23 (1H, t, J=8.1 Hz, 5 position of 3-methoxybenzyl group), 7.54 (1H, dd, J=8.1, 5.1 Hz, 5 position of 3-pyridyl group), 8.39 (1H, dd, J=8.1, 1.5 Hz, 6 position of 3-pyridyl group), 8.44 (1H, s, 8 position of purine skeleton), 8.70 (1H, d, J=5.1 Hz, 4 position of 3-pyridyl group), 9.18 (1H, d, J=1.5 Hz, 2 position of 3-pyridyl group), 12.51 (1H, br. s, NH)

TOF-MS: 334 for $C_{18}H_{16}N_5O_2$ (M+H)

HPLC (the same conditions as in Example 1): Purity: 98.7%, Retention time: 14.38 minutes

EXAMPLE 107

7-(3-Methoxybenzyl)-2-(N-methylaminomethyl)hypoxanthine

An amidation reaction and post-treatment were carried out following the conditions of Example 17, using 1.97 g (8.00 mmol) of 4-amino-1-(3-methoxybenzyl)-5-imidazolecarboxamide prepared in the same manner as in Example 81 and 2-(N-t-butyloxycarbonyl-N-methylamino)acetic acid instead of 3-pyridylacetic acid hydrochloride to obtain 2.12 g of 4-(2-(N-t-butyloxycarbonyl-N-methylamino)acetylamino)-1-(3-methoxybenzyl)-5-imidazolecarboxamide (yield 63%).

A cyclization reaction was carried out for 3 hours under the same conditions as in Example 1 using 2.11 g (5.05 mmol) of the amide obtained above. The resulting product was post-treated to obtain 1.92 g of 2-(N-t-butyloxycarbonyl-N-methylaminomethyl)-7-(3-methoxybenzyl)hypoxanthine (yield 95%).

1.91 g (4.78 mmol) of the carbamate thus prepared was treated with 18 ml of 1,4-dioxane containing 4N hydrogen chloride to obtain 1.70 g of 7-(3-methoxybenzyl)-2-(N-methylaminomethyl)hypoxanthine hydrochloride (yield 96%).

$^1$H-NMR (300 MHz, DMSO-d$_6$, δ ppm):

2.65 (3H, t, J=4.5 Hz, N-methyl group), 3.73 (3H, s, methoxy group), 4.18 (2H, t, J=3.6 Hz, N-methylene), 5.55 (2H, s, methylene of 3-methoxybenzyl group), 6.86 (1H, d, J=7.5 Hz, 4 position of 3-methoxybenzyl group), 6.90 (1H, d, J=7.5 Hz, 6 position of 4-methoxybenzyl group), 6.97 (1H, s, 2 position of 3-methoxybenzyl group), 7.25 (1H, t, J=7.5 Hz, 5 position of 3-methoxy benzyl group), 8.51 (1H, s, 8 position of purine skeleton), 9.42 (2H, qt, J=4.5, 3.6 Hz, NH$_2$), 12.51 (1H, br. s, NH)

TOF-MS: 300 for $C_{15}H_{18}N_5O_2$ (M+H)

HPLC (the same conditions as in Example 1): Purity: 99%, Retention time: 12.87 minutes

EXAMPLE 108

7-(4-Fluorobenzyl)-2-(N-methylaminomethyl)hypoxanthine

An amidation reaction and post-treatment were carried out following the conditions of Example 17, using 2.12 g (9.01 mmol) of 4-amino-1-(4-fluorobenzyl)-5-imidazolecarboxamide prepared in the same manner as in Example 58 and 2-(N-t-butyloxycarbonyl-N-methylamino)acetic acid instead of 3-pyridylacetic acid hydrochloride to obtain 2.63 g of 4-(2-(N-t-butyloxycarbonyl-N-methylamino)acetylamino)-1-(4-fluorobenzyl)-5-imidazolecarboxamide (yield 72%).

A cyclization reaction was carried out for 5 hours under the same conditions as in Example 1 using 2.62 g (6.45 mmol) of the amide obtained above. The resulting product was post-treated to obtain 2.38 g of 2-(N-t-butyloxycarbonyl-N-methylaminomethyl)-7-(4-fluorobenzyl)hypoxanthine (yield 95%).

2.37 g (6.12 mmol) of the carbamate thus prepared was treated with 23 ml of 1,4-dioxane containing 4N hydrogen chloride to obtain 2.20 g of 7-(4-fluorobenzyl)-2-(N-methylaminomethyl)hypoxanthine hydrochloride (yield 100%). $^1$H-NMR (300 MHz, DMSO-d$_6$, δ ppm):

2.65 (3H, t, J=3.9 Hz, N-methyl group), 4.18 (2H, t, J=3.9 Hz, N-methylene), 5.48 (2H, s, methylene of 4-fluorobenzyl group), 7.18 (2H, t, J=8.7 Hz, 3 and 5 positions of 4-fluorobenzyl group), 7.44 (2H, t, J=8.7 Hz, 2 and 6 positions of 4-fluorobenzyl group), 8.56 (1H, s, 8 position of purine skeleton), 9.48 (2H, qt, J=3.9, 3.9 Hz, NH$_2$), 12.51 (1H, br. s, NH)

TOF-MS: 288 for $C_{14}H_{15}FN_5O$ (M+B)

HPLC (the same conditions as in Example 1): Purity: 98%, Retention time: 12.98 minutes

EXAMPLE 109

7-(4-t-Butylbenzyl)-2-(N-methylaminomethyl)hypoxanthine

An amidation reaction and post-treatment were carried out under the same conditions as in Example 17, using 2.50 g (9.18 mmol) of 4-amino-1-(4-t-butylbenzyl)-5-imidazole carboxamide which was prepared in the same manner as in Example 57 and 2-(N-t-butyloxycarbonyl-N-methylamino)acetic acid instead of 3-pyridylacetic acid hydrochloride to obtain 3.27 g of 1-(4-t-butylbenzyl)-4-(2-(N-t- butyloxycarbonyl-N-methylamino)acetylamino)-5-imidazolecarboxamide (yield 80%).

A cyclization reaction was carried out under the same conditions as in Example 1 for 5 hours using 3.05 g (6.88 mmol) of the amide obtained above. The resulting product was post-treated to obtain 2.82 g of 7-(4-t-butylbenzyl)-2-(N-t-butyloxycarbonyl-N-methylaminomethyl) hypoxanthine (yield 96%).

2.5 g (5.88 mmol) of the carbamate thus prepared was treated with 100 ml of 1,4-dioxane containing 4N hydrogen chloride to obtain 2.34 g of 7-(4-t-butylbenzyl)-2-(N-methylaminomethyl) hypoxanthine dihydrochloride (yield 100%).

$^1$H-NMR (300 MHz, DMSO-d$_6$, δ ppm):

1.20 (9H, s, methyls of t-butyl group), 2.65 (3H, m, N-methyl group), 4.18 (2H, t, J=5.0 Hz, N-methylene), 5.33 (2H, s, methylene of benzyl group), 7.29 (2H, d, J=8.5 Hz, 3 and 5 positions of 4-t-butylbenzyl group), 7.35 (2H, d, J=8.5 Hz, 2 and 6 positions of 4-t-butylbenzyl group), 8.43 (1H, s, 8 position of purine skeleton), 9.44–9.45 (2H, m, NH$_2$), 12.74 (1H, br. s, NH)

TOF-MS: 326 for C$_{18}$H$_{24}$N$_5$O (M+H)

HPLC (the same conditions as in Example 1): Purity: 99%, Retention time: 17.48 minutes

EXAMPLE 110

7-(3-Chlorobenzyl)-2-(N-methylaminomethyl) hypoxanthine

An amidation reaction and post-treatment were carried out following the conditions of Example 17, using 1.13 g (4.50 mmol) of 4-amino-1-(3-chlorobenzyl)-5-imidazolecarboxamide prepared in the same manner as in Example 51 and 2-(N-t-butyloxycarbonyl-N-methylamino) acetic acid instead of 3-pyridylacetic acid hydrochloride to obtain 1.61 g of 4-(2-(N-t-butyloxycarbonyl-N-methylamino)acetylamino)-1-(3-chlorobenzyl)-5-imidazolecarboxamide (yield 85%).

A cyclization reaction was carried out for 7 hours under the same conditions as in Example 1 using 1.51 g (3.58 mmol) of the amide obtained above. The resulting product was post-treated to obtain 1.33 g of 2-(N-t-butyloxycarbonyl-N-methylaminomethyl)-7-(3-chlorobenzyl)hypoxanthine (yield 92%).

1.27 g (3.14 mmol) of the carbamate thus prepared was treated with 75 ml of 1,4-dioxane containing 4N hydrogen chloride to obtain 1.02 g of 7-(3-chlorobenzyl)-2-(N-methylaminomethyl)hypoxanthine dihydrochloride (yield 86%).

$^1$H-NMR (300 MHz, DMSO-d$_6$, δ ppm):

2.65 (3H, t, J=4.0 Hz, N-methyl group), 4.18 (2H, t, J=5.0 Hz, N-methylene), 5.57 (2H, s, methylene of 3-chlorobenzyl group), 7.30–7.48 (3H, m, 4, 5 and 6 positions of 3-chlorobenzyl group), 7.46 (1H, s, 2 position of 3-chlorobenzyl group), 8.53 (1H, s, 8 position of purine skeleton), 9.44–9.45 (2H, m, NH$_2$), 12.75 (1H, br. s, NH)

TOF-MS: 304 for C$_{14}$H$_{15}$ClN$_5$O (M+H)

HPLC (the same conditions as in Example 1): Purity: 99%, Retention time: 14.56 minutes

EXAMPLE 111

2-(N-methylaminomethyl)-7-(2-phenylethyl) hypoxanthine

An amidation reaction and post-treatment were carried out following the conditions of Example 17, using 1.84 g (7.99 mmol) of 4-amino-1-(2-phenylethyl)-5-imidazolecarboxamide prepared in the same manner as in Example 56 and 2-(N-t-butyloxycarbonyl-N-methylamino) acetic acid instead of 3-pyridylacetic acid hydrochloride to obtain 3.03 g of 4-(2-(N-t-butyloxycarbonyl-N-methylamino)acetylamino)-1-(2-phenylethyl)-5-imidazolecarboxamide (yield 94%).

A cyclization reaction was carried out for 5.5 hours under the same conditions as in Example 1 using 3.02 g (7.52 mmol) of the amide obtained above. The resulting product was post-treated to obtain 2.76 g of 2-(N-t-butyloxycarbonyl-N-methylaminomethyl)-7-(2-phenylethyl)hypoxanthine (yield 96%).

2.75 g (7.17 mmol) of the carbamate thus prepared was treated with 27 ml of 1,4-dioxane containing 4N hydrogen chloride to obtain 2.55 g of 2-(N-methylaminomethyl)-7-(2-phenylethyl)hypoxanthine hydrochloride (yield 100%).

$^1$H-NMR (300 MHz, DMSO-d$_6$, δ ppm) :

2.66 (3H, t, J=5.1 Hz, N-methyl group), 3.14 (2H, t, J=7.5 Hz, 2 position methylene of phenethyl group), 4.20 (2H, t, J=5.1 Hz, N-methylene), 4.56 (2H, t, J=7. 5 Hz, 1 position methylene of phenethyl group), 7.11–7.28 (5H, m, phenyl), 8.12 (1H, s, 8 position of purine skeleton), 9.44–9.45 (2H, m, NH$_2$), 12.71 (1H, br. s, NH)

TOF-MS: 284 for C$_{15}$H$_{13}$N$_5$O (M+H)

HPLC (the same conditions as in Example 1): Purity: 100%, Retention time: 13.13 minutes

EXAMPLE 112

7-(2-Phenylethyl)-2-(3-pyridyl)hypoxanthine

An amidation reaction and post-treatment were carried out following the conditions of Example 17, using 2.00 g (8.69 mmol) of 4-amino-1-(2-phenylethyl)-5-imidazolecarboxamide prepared in the same manner as in Example 56 and nicotinic acid instead of 3-pyridylacetic acid hydrochloride to obtain crude 1-(2-phenylethyl)-4-(3-pyridylcarbonylamino)-5-imidazolecarboxamide.

A cyclization reaction was carried out under the same conditions as in Example 1 for 15 hours using the crude amide obtained above. The resulting product was post-treated to obtain 1.09 g of 7- (2-phenylethyl)-2- (3-pyridyl) hypoxanthine (yield 40%, 2 steps).

$^1$H-NMR (300 MHz, DMSO-d$_6$, δ ppm):

3.17 (2H, t, J=7.4 Hz, methylene bonding to phenyl group of 2-phenylethyl group), 4.58 (2H, t, J=6.9 Hz, methylene bonding to purine ring of 2-phenylethyl group), 7.12–7.30 (5H, m, aromatic H of 2-phenylethyl group), 7.55 (1H, dd, J=8.1, 5.1 Hz, 5 position of 3-pyridyl group), 8.01 (1H, s, 8 position of purine skeleton), 8.42 (1H, dd, J=8.1, 2.4 Hz, 4 position of 3-pyridyl group), 8.71 (1H, d, J=3.6 Hz, 6 position of 3-pyridyl group), 9.20 (1H, d, J=2.1 Hz, 2 position of 3-pyridyl group), 12.71 (1H, br. s, NH)

TOF-MS: 318 for $C_{18}H_{16}N_5O$ (M+H)

HPLC (the same conditions as in Example 1): Purity: 99.7%, Retention time: 14.06 minutes

EXAMPLE 113

2-Ethyl-7-(2-fluorobenzyl)hypoxanthine

An alkylation reaction, acid hydrolysis, and neutralization were carried out following the conditions of Reference Example 2, using 5.00 g (23.3 mmol) of 4-benzylideneamino-5-imidazole carboxamide obtained in the same manner as in Reference Example 1 and 2-fluorobenzyl chloride instead of benzyl chloride to obtain 4.57 g of 4-amino-1-(2-fluorobenzyl)-5-imidazolecarboxamide (yield 83%, 3 steps).

An amidation reaction and post-treatment were carried out following the conditions of Example 21, using 2.0 g (8.5 mmol) of the amine produced above to obtain 2.06 g of 1-(2-fluorobenzyl)-4-propanoylamino-5-imidazolecarboxamide (yield 83%).

2. 0 g (6.9 mmol) of the amide thus prepared was cyclized for one hour under the same conditions as in Example 1 and post-treated to obtain 1.83 g of 2-ethyl-7-(2fluorobenzyl)hypoxanthine (yield 98%).

$^1$H-NMR (300 MHz, DMSO-$d_6$, δ ppm):

1.20 (3H, t, J=6.6 Hz, methyl of ethyl group), 2.60 (2H, q, J=6.8 Hz, methylene of ethyl group), 5.61 (2H, s, methylene of benzyl group), 7.10–7.38 (4H, m, aromatic H of 2-fluorobenzyl group), 8.21 (1H, s, 8 position of purine skeleton), 12.13 (1H, br. s, NH)

TOF-MS: 273 for $C_{14}H_{14}FN_4O$ (M+H)

HPLC (the same conditions as in Example 1): Purity: 98.7%, Retention time: 14.41 minutes

EXAMPLE 114

2-Ethyl-7-L 3-phenylpropyl)hypoxanthine

An alkylation reaction, acid hydrolysis, and neutralization were carried out following the conditions of Reference Example 2, using 6.00 g (28.0 mmol) of 4-benzylideneamino-5-imidazolecarboxamide obtained in the same manner as in Reference Example 1 and 3-phenylpropyl bromide instead of benzyl chloride to obtain 4.54 g of 4-amino-1-(3-phenylpropyl)-5-imidazolecarboxamide (yield 70%, 3 steps).

An amidation reaction and post-treatment were carried out following the conditions of Example 21, using 2.0 g (8.2 mmol) of the amine produced above to obtain 2.08 g of 1-(3-phenylpropyl)-4-propanoylamino-5-imidazolecarboxamide (yield 85%).

2.0 g (6.7 mmol) of the amide thus prepared was cyclized for 2 hours under the same conditions as in Example 1 and post-treated to obtain 1.17 g of 2-ethyl-7-(3-phenylpropyl)hypoxanthine (yield 62%).

$^1$H-NMR (300 MHz, DMSO-$d_6$, δ ppm):

1.21 (3H, t, J=7.7 Hz; methyl of ethyl group), 2.13 (2H, m, central methylene of 3-phenylpropyl group), 2.50–2.65 (4H, m, phenyl group side methylene of 3-phenylpropyl group, methylene of ethyl group), 4.32 (2H, t, J=6.6 Hz, purine ring side methylene of 3-phenylpropyl group), 7.10–7.29 (5H, m, aromatic H of 3-phenylpropyl group), 8.16 (1H, s, 8 position of purine skeleton), 12.11 (1H, m, br. s, amide NH)

TOF-MS: 283 for $C_{16}H_{19}N_4O$ (M+H)

HPLC (the same conditions as in Example 1): Purity: 99.8%, Retention time: 15.69 minutes

EXAMPLE 115

2-(N-methylaminomethyl)-7-(4-methylbenzyl) hypoxanthine

An amidation reaction and post-treatment were carried out following the conditions of Example 17, using 1.61 g (6.99 mmol) of 4-amino-1-(4-methylbenzyl)-5-imidazolecarboxamide prepared in the same manner as in Example 87 and 2-(N-t-butyloxycarbonyl-N-methylamino) acetic acid instead of 3-pyridylacetic acid hydrochloride to obtain 1.70 g of 4-(2-(N-t-butyloxycarbonyl-N-methylamino)acetylamino)-1-(4-methylbenzyl)-5-imidazolecarboxamide (yield 60%).

A cyclization reaction was carried out for 5 hours under the same conditions as in Example 1 using 1.69 g (4.21 mmol) of the amide obtained above. The resulting product was post-treated to obtain 1.56 g of 2-(N-t-butyloxycarbonyl-N-methylaminomethyl)-7-(4-methylbenzyl)hypoxanthine (yield 97%).

1.55 g (4.04 mmol) of the carbamate thus prepared was treated with 15 ml of 1,4-dioxane containing 4N hydrogen chloride to obtain 1.44 g of 2-(N-methylaminomethyl)-7-(4-methylbenzyl)hypoxanthine hydrochloride (yield 100%).

$^1$H-NMR (300 MHz, DMSO-$d_6$, δ ppm):

2.25 (3H, s, methyl group of 4-methylbenzyl), 2.65 (3H, t, J=4.7 Hz, N-methyl group), 4.18 (2H, t, J=5.1 Hz, N-methylene), 5.51 (2H, s, methylene of 4-methylbenzyl group), 7.14 (2H, d, J=7.8 Hz, 3 and5positions of4-methylbenzyl group), 7.25 (2H, d, J=7.8 Hz, 2 and 6 positions of 4-methylbenzyl group), 8.50 (1H, s, 8 position of purine skeleton), 9.44–9.45 (2H, m, $NH_2$), 12.74 (1H, br. s, NH)

TOF-MS: 284 for $C_{15}H_{18}N_5O$ (M+H)

HPLC (the same conditions as in Example 1): Purity: 97%, Retention time: 13.67 minutes

EXAMPLE 116

7-(4-Methylbenzyl)--2-(3-pyridyl)hypoxanthine

An amidation reaction and post-treatment were carried out under the same conditions as in Example 19, using 1.61 g (6.99 mmol) of 4-amino-1-(4-methylbenzyl)-5-imidazole carboxamide which was prepared in the same manner as in Example 87 and nicotinic acid instead of cyclopentylacetic acid to obtain 1.43 g of 1-(4-methylbenzyl)-4-(3-pyridylcarbonylamino)-5-imidazolecarboxamide (yield 61%).

A cyclization reaction was carried out under the same conditions as in Example 1 for 10 hours using 1.43 g (4.26 mmol) of the amide obtained above. The resulting product was post-treated to obtain 1.23 g of 7-(4-methylbenzyl)-2-(3-pyridyl)hypoxanthine (yield 91%).

$^1$H-NMR (300 MHz, DMSO-d$_6$, δ ppm):

2.25 (3H, s, methyl of 4-methylbenzyl group), 5.54 (2H, s, methylene of 4-methylbenzyl group), 7.13 (2H, d, J=7.2 Hz, 3 and 5 positions of 4-methylbenzyl group), 7.28 (2H, d, J=7.2 Hz, 2 and 6 positions of 4-methylbenzyl group), 7.50 (1H, dd, J=8.1, 4.8 Hz, 5 position of 3-pyridyl group), 8.31 (1H, s, 8 position of purine skeleton), 8.41 (1H, ddd, J=8.1, 2.1, 1.0 Hz, 6 position of 3-pyridyl group), 8.46 (1H, dd, J=4.8, 1.0 Hz, 4 position of 3-pyridyl group), 9.21 (1H, d, J=2.1 Hz, 2 position of 3-pyridyl group)

TOF-MS: 318 for C$_{18}$H$_{16}$N$_5$O (M+H)

HPLC (the same conditions as in Example 1): Purity: 97%, Retention time: 15.13 minutes

EXAMPLE 117

2-(2-Fluorophenyl)-7-(4-methylbenzyl)hypoxanthine

An amidation reaction and post-treatment were carried out under the same conditions as in Example 1, using 1.25 g (5.43 mmol) of 4-amino-1-(4-methylbenzyl)-5-imidazole carboxamide which was prepared in the same manner as in Example 87 and 2-fluorobenzoyl chloride instead of benzoyl chloride to obtain 1.15 g 4-(2-fluorobenzoylamino)-1-(4-methylbenzyl)-5-imidazolecarboxamide (yield 60%).

A cyclization reaction was carried out under the same conditions as in Example 1 for 10 hours using 1.10 g (3.12 mmol) of the amide obtained above. The resulting product was post-treated to obtain 0.95 g of 2-(2-fluorophenyl)-7-(4-methylbenzyl)hypoxanthine (yield 91%).

$^1$H-NMR (300 MHz, DMSO-d$_6$, δ ppm):

2.26 (3H, s, methyl of 4-methylbenzyl group), 5.53 (2H, s, methylene of 4-methylbenzyl group), 7.14 (2H, d, J=7.7 Hz, 3 and 5 positions of 4-methylbenzyl group), 7.28 (2H, d, J=7.7 Hz, 2 and 6 positions of 4-methylbenzyl group), 7.30–7.37 (2H, m, 3 and 5 positions of 2-fluorophenyl group), 7.52–7.57 (1H, m, 4 position of 2-fluorophenyl group), 7.67–7.73 (1H, m, 6 position of 2-fluorophenyl group), 8.37 (1H, s, 8 position of purine skeleton), 12.52 (1H, br. s, NH)

TOF-MS: 335 for C$_{19}$H$_{16}$FN$_4$O (M+H)

HPLC (the same conditions as in Example 1): Purity: 99%, Retention time: 19.36 minutes

EXAMPLE 118

7-Benzyl-2-(2-thienyl)hypoxanthine

An amidation reaction and post-treatment were carried out following the conditions of Example 17, using 2.14 g (9.99 mmol) of 4-amino-1-benzyl-5-imidazolecarboxamide prepared in the same manner as in Reference Example 2 and 2-thiophenecarboxylic acid instead of 3-pyridylacetic acid hydrochloride to obtain 1.97 g of 1-benzyl-4-(2-thienylcarbonylamino)-5-imidazolecarboxamide (yield 60%).

A cyclization reaction was carried out for 6 hours under the same conditions as in Example 1 using 1.97 g (6.04 mmol) of the amide obtained above. The resulting product was post-treated to obtain 1.35 g of 7-benzyl-2-(2-thienyl)hypoxanthine (yield 72%).

$^1$H-NMR (270 MHz, DMSO-d$_6$, δ ppm):

5.58 (2H, s, methylene of benzyl group), 7.19 (1H, dd, J=4.3, 3.6 Hz, 4 position of thiophene), 7.32–7.37 (5H, m, aromatic H of benzyl group), 7.80 (1H, d, J=4.3 Hz, 5 position of thiophene), 8.14 (1H, d, J=3.6 Hz, 3 position of thiophene), 8.40 (1H, s, 8 position of purine skeleton), 12.63 (1H, br. s, NH)

TOF-MS: 309 for C$_{16}$H$_{13}$N$_4$OS (M+H)

HPLC (the same conditions as in Example 1): Purity: 95%, Retention time: 17.91 minutes

EXAMPLE 119

2-Ethyl-7-(2-methylbenzyl)hypoxanthine

An alkylation reaction and acid hydrolysis were carried out following the conditions of Reference Example 2, using 6.00 g(28.0 mmol) of 4-benzylideneamino-5-imidazolecarboxamide obtained in the same manner as in Reference Example 1 and 2-methylbenzyl chloride instead of benzyl chloride to obtain 6.06 g of 4-amino-1-(2-methylbenzyl)-5-imidazolecarboxamide hydrochloride (yield 88%, 2 steps).

An amidation reaction and post-treatment were carried out following the conditions of Example 21, using 2.0 g (7.5 mmol) of the amine hydrochloride produced above to obtain 0.74 g of 1-(2-methylbenzyl)-4-propanoylamino-5-imidazole carboxamide (yield 34%).

0.72 g (2.5 mmol)of the amide thus prepared was cyclized for one hour under the same conditions as in Example 1 and post-treated to obtain 0.63 g 2-ethyl-7-(2-methylbenzyl) hypoxanthine (yield 94%).

$^1$H-NMR (300 MHz, DMSO-d$_6$, δ ppm):

1.21 (3H, t, J=7.8 Hz, methyl of ethyl group), 2.31 (3H, s, methyl group of 2-methylbenzyl group), 2.61 (2H, q, J=7.3 Hz, methylene of ethyl group), 5.56 (2H, s, methylene of 2-methylbenzyl group), 6.71 (1H, d, J=7.2 Hz, aromatic H of 2-methylbenzyl group), 7.07–7.23 (3H, m, aromatic H of 2-methylbenzyl group), 8.12 (1H, s, 8 position of purine skeleton), 12.13 (1H, br. s, NH)

TOF-MS: 269 for C$_{15}$H$_{17}$N$_4$O (M+H)

HPLC (the same conditions as in Example 1): Purity: 97.1%,

Retention time: 15.23 minutes

EXAMPLE 120

2-Ethyl-7-(3-methylbenzyl)hypoxanthine

An alkylation reaction, acid hydrolysis, and neutralization were carried-out following the conditions of Reference Example 2, using 2.14 g (9.99 mmol) of 4-benzylideneamino-5-imidazolecarboxamide obtained in the same manner as in Reference Example 1 and 3-methylbenzyl chloride instead of benzyl chloride to obtain 1.07 g of 4-amino-1-(3-methylbenzyl)-5-imidazolecarboxamide (yield 47%, 3 steps).

An amidation reaction and post-treatment were carried out following the conditions of Example 21, using 0.95 g (4.13 mmol) of the amine produced above to obtain 0.98 g of 1-(3-methylbenzyl)-4-propanoylamino-5-imidazolecarboxamide (yield 83%).

0.92 g (3.21 mmol) of the amide thus prepared was cyclized for 4.5 hours under the same conditions as in Example 1 and post-treated to obtain 0.54 g of 2-ethyl-7-(3-methylbenzyl)hypoxanthine (yield 63%).

$^1$H-NMR (300 MHz, DMSO-$d_6$, δ ppm):

1.20 (3H, t, J=7.6 Hz, methyl of ethyl group), 2.31 (3H, s, methyl group of 3-methylbenzyl), 2.60 (2H, q, J=7.6 Hz, methylene of ethyl group), 5.49 (2H, s, methylene of 3-methylbenzyl group), 7.01–7.23 (4H, m, 3-methylbenzyl group), 8.30 (1H, s, 8 position of purine skeleton), 12.12 (1H, br. s, NH)

TOF-MS: 269 for $C_{15}H_{17}N_4O$ (M+H)

HPLC (the same conditions as in Example 1): Purity: 86%, Retention time: 16.07 minutes

EXAMPLE 121

2-Ethyl-7-(3-fluorobenzyl)hypoxanthine

An amidation reaction and post-treatment were carried out following the conditions of Example 21 using 2.00 g (8.54 mmol) of 4-amino-1-(3-fluorobenzyl)-5-imidazolecarboxamide which was prepared in the same manner as in Example 82 to obtain 2.03 g of 1-(3-fluorobenzyl)-4-propanoylamino-5-imidazole carboxamide (yield 82%).

1.92 g (6.61 mmol) of the amide thus prepared was cyclized for 4 hours under the same conditions as in Example 1 and post-treated to obtain 1.54 g of 2-ethyl-7-(3-fluorobenzyl)hypoxanthine (yield 86%).

$^1$H-NMR (300 MHz, DMSO-$d_6$, δ ppm):

1.20 (3H, t, J=7.6 Hz, methyl of ethyl group), 2.60 (2H, q, J=7.5 Hz, methylene of ethyl group), 5.54 (2H, s, methylene of benzyl group), 7.08–7.18 (3H, m, aromatic H of 3-fluorobenzyl group), 7.34–7.44 (1H, m, aromatic H of 3-fluorobenzyl group), 8.34 (1H, s, 8 position of purine skeleton), 12.17 (1H, br. s, NH)

TOF-MS: 273 for $C_{14}H_{14}FN_4O$ (M+H)

HPLC (the same conditions as in Example 1): Purity: 98.8%, Retention time: 14.64 minutes

EXAMPLE 122

7-(3-Chlorobenzyl)-2-propylhypoxanthine

An amidation reaction and post-treatment were carried out following the conditions of Example 21 using 2.00 g (7.98 mmol) of 4-amino-1-(3-chlorobenzyl)-5-imidazolecarboxamide which was prepared in the same manner as in Example 51 and butanyric anhydride instead of propionic anhydride to obtain 2.40 g of 4-butanoylamino-1-(3-chlorobenzyl)-5-imidazolecarboxamide (yield 94%).

2.20 g (6.86 mmol) of the amide thus prepared was cyclized for 5 hours under the same conditions as in Example 1 and post-treated to obtain 1.86 g 7-(3-chlorobenzyl)-2-propylhypoxanthine (yield 90%).

$^1$H-NMR (300 MHz, DMSO-$d_6$, δ ppm):

0.94 (3H, t, J=7.4 Hz, methyl of propyl group), 1.69 (2H, tq, J=7.4, 7.4 Hz, 2 position methylene of propyl group), 2.56 (2H, t, J=7.4 Hz, 1 position methylene of propyl group), 5.52 (2H, s, methylene of benzyl group), 7.27–7.45 (4H, m, 3-chlorobenzyl group), 8.35 (1H, s, 8 position of purine skeleton), 12.15 (1H, br. s, NH)

TOF-MS: 303 for $C_{15}H_{16}ClN_4O$ (M+H)

HPLC (the same conditions as in Example 1): Purity: 98%, Retention time: 17.60 minutes

EXAMPLE 123

7-(4-t-butylbenzyl)-2-(3-fluorophenyl)hypoxanthine

An amidation reaction and post-treatment were carried out under the same conditions as in Example 1, using 1.54 g (5.65 mmol) of 4-amino-1-(4-t-butylbenzyl)-5-imidazole carboxamide which was prepared in the same manner as in Example 57 and 3-fluorobenzoyl chloride instead of benzoyl chloride to obtain 1.57 g of 1-(4-t-butylbenzyl)-4-(3-fluorobenzoylamino)-5-imidazolecarboxamide (yield 70%).

A cyclization reaction was carried out under the same conditions as in Example 1 for 10.5 hours using 1.56 g (3.96 mmol) of the-amide obtained above. The resulting product was post-treated to obtain 1.43 g of 7-(4-t-butylbenzyl)-2-(3-fluorophenyl)hypoxanthine (yield 96%).

$^1$H-NMR (300 MHz, DMSO-$d_6$, δ ppm):

1.24 (9H, s, t-butyl group), 5.57 (2H, s, methylene of benzyl group), 7.30–7.39 (4H, m, aromatic H of 4-t-butylbenzyl group), 7.69–7.88 (2H, m, 4 and 5 positions of 3-fluorophenyl group), 8.34 (1H, s, 8 position of purine skeleton), 8.40–8.49 (2H, m, 2 and 6 positions of 3-fluorophenyl group)

TOF-MS: 377 for $C_{22}H_{22}FN_4O$ (M+H)

HPLC (the same conditions as in Example 1): Purity: 97.3%, Retention time: 22.14 minutes

EXAMPLE 124

7-(4-t-Butylbenzyl)-2-(4-fluorophenyl)hypoxanthine

An amidation reaction and post-treatment were carried out under the same conditions as in Example 1, using 2.63 g (9.66 mmol) of 4-amino-1-(4-t-butylbenzyl)-5-imidazolecarboxamide which was prepared in the same manner as in Example 57 and 4-fluorobenzoyl Chloride instead of benzoyl chloride to obtain 2.13 g of 1-(4-t-butylbenzyl)-4-(4-fluorobenzoylamino)-5-imidazolecarboxamide (yield 56%).

A cyclization reaction was carried out under the same conditions as in Example 1 for 15 hours using 2.12 g (5.37 mmol) of the amide obtained above. The resulting product was post-treated to obtain 1.95 g of 7-(4-t-butylbenzyl)-2-(4-fluorophenyl)hypoxanthine (yield 97%).

¹H-NMR (300 MHz, DMSO-d$_6$, δ ppm):
1.22 (9H, s, methyl of t-butyl group),
5.53 (2H, s, methylene of 4-t-butylbenzyl group),
7.28–7.36 (6H, m, 4-t-butyl benzyl group, 3 and 5 positions of 4-fluorophenyl group),
8.15 (2H, dd, J=8.8, 5.8 Hz, 2 and 6 positions of 4-fluorophenyl group),
8.30 (1H, s, 8 position of purine skeleton)
TOF-MS: 377 for C$_{22}$H$_{22}$FN$_4$O (M+H)
HPLC (the same conditions as in Example 1): Purity: 93%, Retention time: 21.54 minutes

EXAMPLE 125

7-(4-t-Butylbenzyl)-2-(3-trifluoromethylphenyl) hypoxanthine

An amidation reaction and post-treatment were carried out under the same conditions as in Example 1, using 1.91 g (7.01 mmol) of 4-amino-1-(4-t-butylbenzyl)-5-imidazole carboxamide which was prepared in the same manner as in Example 57 and 3-trifluoromethylbenzoyl chloride instead of benzoyl chloride to obtain 2.17 g of 1-(4-t-butylbenzyl)-4-(3-trifluoromethylbenzoylamino)-5-imidazolecarboxamide (yield 70%).

A cyclization reaction was carried out under the same conditions as in Example 1 for 15 hours using 2.16 g (4.86 mmol) of the amide obtained above. The resulting product was post-treated to obtain 1.91 g of 7-(4-t-butylbenzyl)-2-(3-trifluoromethylphenyl)hypoxanthine (yield 92%).

¹H-NMR (300 MHz, DMSO-d$_6$, δ ppm):
1.24 (9H, s, t-butyl group),
5.56 (2H, s, methylene of benzyl group),
7.29–7.38 (4H, m, aromatic H-of 4-t-butylbenzyl group),
7.50–7.57 (2H, m, 4 and 5 positions of 3-trifluoromethylphenyl group),
7.90–8.02 (2H, m, 2 and 6 positions of 3-trifluoromethylphenyl group),
8.32 (1H, s, 8 position of purine skeleton)
TOF-MS: 427 for C$_{23}$H$_{22}$F$_3$N$_4$O (M+H)
HPLC (the same conditions as in Example 1): Purity: 96%, Retention time: 23.27 minutes

EXAMPLE 126

7-(2-Fluorobenzyl)-2-(2-fluorophenyl)hypoxanthine

An amidation reaction and post-treatment were carried out under the same conditions as in Example 22, using 1.50 g (6.40 mol) of 4-amino-1-(2-fluorobenzyl)-5-imidazole carboxamide which was prepared in the same manner as in Example 113 and 2-fluorobenzoyl chloride instead of benzoyl chloride to obtain 2.21 g of 4-(2-fluorobenzoylamino)-1-(2-fluorobenzyl)-5-imidazolecarboxamide (yield 97%).

A cyclization reaction was carried out under the same conditions as in Example 1 for 6 hours using 2.10 g (5.89 mmol) of the amide obtained above. The resulting product was post-treated to obtain 1.33 g of 7-(2-fluorobenzyl)-2-(2-fluorophenyl)hypoxanthine (yield 67%).

¹H-NMR (270 MHz, DMSO-d$_6$, δ ppm):
5.68 (2H, s, methylene of 2-fluorobenzyl group),
7.14–7.41 (6H, m, aromatic H (4H) of 2-fluorobenzyl group, 3 and 5 positions of 2-fluorophenyl group),
7.55–7.64 (1H, m, 4 position of 2-fluorophenyl group),
7.68–7.75 (1H, m, 6 position of 2-fluorophenyl group),
8.35 (1H, s, 8 position of purine skeleton),
12.58 (1H, br. s, NH)
TOF-MS: 339 for C$_{18}$H$_{13}$F$_2$N$_4$O (M+H)
HPLC (the same conditions as in Example 1): Purity: 97.3%, Retention time: 17.55 minutes

EXAMPLE 127

7-(2-Fluorobenzyl)-2-(3-pyridyl)hypoxanthine

An amidation reaction and post-treatment were carried out following the conditions of Example 17, using 2.00 g (8.54 mmol) of 4-amino-1-(2-fluorobenzyl)-5-imidazolecarboxamide prepared in the same manner as in Example 113 and 2-nicotinic acid instead of 3-pyridylacetic acid hydrochloride to obtain 1.87 g of 1-(2-fluorobenzyl)-4-(3-pyridylcarbonylamino)-5-imidazolecarboxamide (yield 65%).

A cyclization reaction was carried out for 6 hours under the same conditions as in Example 1 using 1.87 g (5.51 mmol) of the amide obtained above. The resulting product was post-treated to obtain 1.19 g of 7-(2-fluorobenzyl)-2-(3-pyridyl)hypoxanthine (yield 67%).

¹H-NMR (300 MHz, DMSO-d$_6$, δ ppm):
5.69 (2H, s, methylene of 2-fluorobenzyl group),
7.13–7.43 (4H, m, aromatic H of 2-fluorobenzyl group),
7.56 (1H, dd, J=8.1, 4.6 Hz, 5 position of 3-pyridyl group),
8.39 (1H, s, 8 position of purine skeleton),
8.42 (1H, m, 4 position of 3-pyridyl group),
8.72 (1H, dd, J=4.9, 1.6 Hz, 6 position of 3-pyridyl group),
9.20 (1H, d, J=1.4 Hz, 2 position of 3-pyridyl group),
12.72 (1H, br. s, NH)
TOF-MS: 322 for C$_{17}$H$_{13}$FN$_5$O (M+H)
HPLC (the same conditions as in Example 1): Purity: 99.5%, Retention time: 13.50 minutes

EXAMPLE 128

7-(2-Fluorobenzyl)-2-(N-methylaminomethyl) hypoxanthine

An amidation reaction and post-treatment were carried out following the conditions of Example 17, using 2.00 g (8.54 mmol) of 4-amino-1-(2-fluorobenzyl)-5-imidazolecarboxamide prepared in the same manner as in Example 113 and 2-(N-t-butyloxycarbonyl-N-methylamino) acetic acid instead of 3-pyridylacetic acid hydrochloride to obtain 3.35 g of 4-(2-(N-t-butyloxycarbonyl-N-methylamino)acetylamino)-1-(2-fluorobenzyl)-5-imidazolecarboxamide (yield 97%).

A cyclization reaction was carried out for 1 hour under the same conditions as in Example 1 using 3.20 g (7.89 mmol) of the amide obtained above. The resulting product was post-treated to obtain 2.09 g of 2-(N-t-butyloxycarbonyl-N-methylaminomethyl)-7-(2-fluorobenzyl)hypoxanthine (yield 69%).

1.80 g (4.65 mmol) of the carbamate thus prepared was treated with 20 ml of 1,4-dioxane containing 4N hydrogen chloride to obtain 1.61 g of 7-(2-fluorobenzyl)-2-(N-methylaminomethyl)hypoxanthine hydrochloride (yield 96%).

¹H-NMR (300 MHz, DMSO-d₆, δ ppm):

2.66 (3H, br. t, N-methyl), 4.19 (2H, br. t, methylene of methylaminomethyl group), 5.66 (2H, s, methylene of 2-fluorobenzyl group), 7.15–7.40 (4H, m, aromatic H of 2-fluorobenzyl group), 8.40 (1H, s, 8 position of purine skeleton), 9.45 (2H, br. s, ammonium NH₂), 12.76 (1H, br. s, amide NH)

TOF-MS: 288 for $C_{14}H_{15}FN_5O$ (M+H)

HPLC (the same conditions as in Example 1): Purity: 99.8%, Retention time: 12.37 minutes

EXAMPLE 129

2-(2-Fluorophenyl)-7-(3-phenylpropyl)hypoxanthine

An amidation reaction and post-treatment were carried out following the conditions of Example 22 using 1.50 g (6.14 mmol) of 4-amino-1-(3-phenylpropyl)-5-imidazolecarboxamide which was prepared in the same manner as in Example 114 and 2-fluorobenzoyl chloride instead of benzoyl chloride to obtain 1.97 g of 4-(2-fluorobenzoylamino)-1-(3-phenylpropyl)-5-imidazolecarboxamide (yield 88%).

1.87 g (5.10 mmol) of the amide thus prepared was cyclized for 4.5 hours under the same conditions as in Example 1 and post-treated to obtain 1.12 g of 2-(2-fluorophenyl)-7-(3-phenylpropyl)hypoxanthine (yield 63%).

¹H-NMR (300 MHz, DMSO-d₆, δ ppm):

2.19 (2H, m, central (β-position) methylene of 3-phenylpropyl group), 2.61 (2H, t, J=7.8 Hz, phenyl group side (γ-position) methylene of 3-phenylpropyl group), 4.39 (2H, t, J=6.8 Hz, purine ring side (α-position) methylene of 3-phenylpropyl group), 7.13–7.41 (7H, m, aromatic H (5H) of 3-phenylpropyl group, 3 and 5 positions of 2-fluorophenyl group), 7.55–7.64 (1H, m, 4 position of 2-fluorophenyl group), 7.68–7.76 (1H, m, 6 position of 2-fluorophenyl group), 8.29 (1H, s, 8 position of purine skeleton), 12.54 (1H, br. s, NH)

TOF-MS: 349 for $C_{20}H_{18}FN_4O$ (M+H)

HPLC (the same conditions as in Example 1): Purity: 99.5%, Retention time: 18.94 minutes

EXAMPLE 130

7-3-Phenylpropyl)-2-(3-pyridyl)hypoxanthine

An amidation reaction and post-treatment were carried out following the conditions of Example 17, using 2.00 g (8.19 mmol) of 4-amino-1-(3-phenylpropyl)-5-imidazolecarboxamide prepared in the same manner as in Example 114 and nicotinic acid instead of 3-pyridylacetic acid hydrochloride to obtain crude 1-(3-phenylpropyl)-4-(3-pyridylcarbonylamino)-5-imidazolecarboxamide.

A cyclization reaction was carried out for 8 hours under the same conditions as in Example 1 using the crude amide obtained above. The resulting product was post-treated to obtain 1.29 g of 7-(3-phenylpropyl)-2-(3-pyridyl)hypoxanthine (yield 48%, 2 steps).

¹H-NMR (270 MHz, DMSO-d₆, δ ppm), 2.19 (2H, m, central (β-position) methylene of 3-phenylpropyl group), 2.60 (2H, t, J=7.8 Hz, phenyl group side (γ-position) methylene of 3-phenylpropyl group), 4.40 (2H, t, J=6.8 Hz, purine ring side (α-position) methylene of 3-phenylpropyl group), 7.13–7.30 (5H, m, aromatic H of 3-phenylpropyl group), 7.57 (1H, dd, J=7.8, 4.9 Hz, 5 position of 3-pyridyl group), 8.30 (1H, s, 8 position of purine skeleton), 8.41 (1H, m, 4 position of 3-pyridyl group), 8.72 (1H, dd, J=4.9, 1.4 Hz, 6 position of 3-pyridyl group), 9.21 (1H, d, J=1.6 Hz, 2 position of 3-pyridyl group), 12.70 (1H, br s, NH)

TOF-MS: 332 for $C_{19}H_{17}N_5O$ (M+H)

HPLC (the same conditions as in Example 1): Purity: 98.9%, Retention time: 15.02 minutes

EXAMPLE 131

7-(3-Phenylpropyl)-2-(N-methylaminomethyl) hypoxanthine

An amidation reaction and post-treatment were carried out following the conditions of Example 17, using 2.00 g (8.19 mmol) of 4-amino-1-(3-phenylpropyl)-5-imidazolecarboxamide prepared in the same manner as in Example 114 and 2-(N-t-butyloxycarbonyl-N-methylamino) acetic acid instead of 3-pyridylacetic acid hydrochloride to obtain 3.20 g of 4-(2-(N-t-butyloxycarbonyl-N-methylamino)acetylamino)-1-(3-phenylpropyl)-5-imidazolecarboxamide (yield 94%).

A cyclization reaction was carried out for one hour under the same conditions as in Example 1 using 3.09 g (7.43 mmol) of the amide obtained above. The resulting product was post-treated to obtain 2.29 g of 2-(N-t-butyloxycarbonyl-N-methylaminomethyl)-7-(3-phenylpropyl)hypoxanthine (yield 78%).

1.80 g (4.53 mmol) of the carbamate thus prepared was treated with 20 ml of 1,4-dioxane containing 4N hydrogen chloride to obtain 1.61 g of 7-(3-phenylpropyl)-2-(N-methylaminomethyl)hypoxanthine hydrochloride (yield 96%).

¹H-NMR (270 MHz, DMSO-d₆, δ ppm)):

2.16 (2H, m, central (β-position) methylene of 3phenyl-propyl group), 2.58 (2H, t, J=7.0 Hz, phenyl group side (γ-position) methylene of 3-phenylpropyl group), 2.67 (3H, br. s, N-methyl), 4.20 (2H, br. s, methylene of methylaminomethyl group), 4.38 (2H, t, J=6.6 Hz, purin ring side (α-position) methylene of 3-phenylpropyl group), 7.16–7.30 (5H, m, aromatic H of 3-phenylpropyl group), 8.38 (1H, s, 8 position of purine skeleton), 9.43 (2H, br. s, ammonium NH₂), 12.75 (1H, br. s, amide NH)

TOF-MS: 298 for $C_{16}H_{19}N_5O$ (M+H)

HPLC (the same conditions as in Example 1): Purity: 99.5%, Retention time: 14.05 minutes

EXAMPLE 132

7-(2-Fluorobenzyl)-2-phenylhypoxanthine

An amidation reaction and post-treatment were carried out following the conditions of Example 1, using 1.00 g (4.27 mmol) of 4-amino-1-(2-fluorobenzyl)-5-imidazolecarboxamide prepared in the same manner as in Example 113 to obtain 1.22 g of 4-benzoylamino-1-(2-fluorobenzyl)-5-imidazole carboxamide (yield 84%).

A cyclization reaction was carried out for 16 hours under the same conditions as in Example 1 using 1.10 g (3.25 mmol) of the amide obtained above. The resulting product was post-treated to obtain 0.61 g of 2-phenyl-7-(2-fluorobenzyl)hypoxanthine (yield 59%).

$^1$H-NMR (300 MHz, DMSO-$d_6$, δ ppm):

5.67 (2H, s, methylene of 2-fluorobenzyl group), 7.13–7.39 (4H, m, aromatic H of 2-fluorobenzyl group), 7.46–7.54 (3H, m, 3, 4 and 5 positions of 2 position phenyl group), 8.07 (2H, d, J=6.0 Hz, 2 and 6 positions of 2 position phenyl group), 8.31 (1H, s, 8 position of purine skeleton), 12.48 (1H, br. s, NH)

TOF-MS: 321 for $C_{18}H_{14}FN_4O$ (M+H)

HPLC (the same conditions as in Example 1): Purity: 98.4%, Retention time: 17.72 minutes

EXAMPLE 133

7-(3-Phenylpropyl)-2-phenylhypoxanthine

An amidation reaction and post-treatment were carried out following the conditions of Example 1, using 1.0 g (4.1 mmol) of 4-amino-1-(3-phenylpropyl)-5-imidazolecarboxamide prepared in the same manner as in Example 114 to obtain crude 4-benzoylamino-1-(3-phenylpropyl)-5-imidazolecarboxamide.

A cyclization reaction was carried out for 15 hours under the same conditions as in Example 1 using the crude amide obtained above. The resulting product was post-treated to obtain 0.56 g of 2-phenyl-7-(3-phenylpropyl)hypoxanthine (yield 32%, 2 steps).

$^1$H-NMR (300 MHz, DMSO-$d_6$, δ ppm):

2.18 (2H, m, 2 position methylene of 3-phenylpropyl group), 2.60 (2H, t J=7.7 Hz, 3 position methylene of 3-phenyl propyl group), 4.39 (2H, t, J=7.2 Hz, 1 position methylene of 3-phenylpropyl group), 7.13–7.31 (5H, m, aromatic H of benzyl group), 7.49–7.55 (3H, m, 3, 4 and 5 positions of 2 position phenyl group), 8.07–8.02 (2H, m, 2 and 6 positions of 2 position phenyl group), 8.26 (1H, s, 8 position of purine skeleton), 12.47 (1H, br. s, NH)

TOF-MS: 331 for $C_{20}H_{19}N_4O$ (M+H)

HPLC (the same conditions as in Example 1): Purity: 99.6%, Retention time: 18.86 minutes

EXAMPLE 134

2-(3-Fluorophenyl)-7-(4-methylbenzyl)hypoxanthine

An amidation reaction and post-treatment were carried out following the conditions of Example 1, using 2.30 g (9.99 mmol) of 4-amino-1-(4-methylbenzyl)-5-imidazolecarboxamide prepared in the same manner as in Example 87 and 3-fluorobenzoyl chloride instead of benzoyl chloride to obtain 3.11 g of 4-(3-fluorobenzoylamino)-1-(4-methylbenzyl)-5-imidazole carboxamide (yield 88%).

A cyclization reaction was carried out for 9 hours and 40 minutes under the same conditions as in Example 1 using 3.10 g (8.80 mmol) of the amide obtained above. The resulting product was post-treated to obtain 2.82 g of 2-(3-fluorophenyl)-7-(4-methylbenzyl)hypoxanthine (yield 96%).

$^1$H-NMR (300 MHz, DMSO-$d_6$, δ ppm):

2.25 (3H, s, methyl group of 4-methylbenzyl), 5.53 (2H, s, methylene of 4-methylbenzyl group), 7.13 (2H, d, J=8.1 Hz, 3 and 5 positions of 4-methylbenzyl group), 7.27 (2H, d, J=8.1 Hz, 2 and 6 positions of 4-methylbenzyl group), 7.30–7.36 (1H, m, 3-fluorophenyl group), 7.49–7.56 (1H, m, 3-fluorophenyl group), 7.88–7.98 (2H, m, 3-fluorophenyl group), 8.31 (1H, s, 8 position of purine skeleton)

TOF-MS: 335 for $C_{19}H_{16}FN_4O$ (M+H)

HPLC (the same conditions as in Example 1): Purity: 99.4%, Retention time: 18.76 minutes

EXAMPLE 135

2-(4-Fluorophenyl)-7-(4-methylbenzyl)hypoxanthine

An amidation reaction and post-treatment were carried out following the conditions of Example 1, using 2.30 g (9.99 mmol) of 4-amino-1-(4-methylbenzyl)-5-imidazolecarboxamide prepared in the same manner as in Example 87 and 4-fluorobenzoyl chloride instead of benzoyl chloride to obtain 2.26 g of 4-(4-fluorobenzoylamino)-1-(4-methylbenzyl)-5-imidazole carboxamide (yield 64%).

A cyclization reaction was carried out for 7 hours under the same conditions as in Example 1 using 2.25 g (6.39 mmol) of the amide obtained above. The resulting product was post-treated to obtain 1.91 g of 2-(4-fluorophenyl)-7-(4-methylbenzyl)hypoxanthine (yield 89%).

$^1$H-NMR (300 MHz, DMSO-$d_6$, δ ppm):

2.25 (3H, s, methyl of 4-methylbenzyl group), 5.51–5.53 (2H, m, methylene of 4-methylbenzyl group), 7.13 (2H, d, J=7.9 Hz, 3 and 5 positions 4-methylbenzyl group), 7.27 (2H, d, J=7.9 Hz, 2 and 6 positions of 4-methylbenzyl group), 7.33 (2H, t, J=8.2 Hz, 3 and 5 positions of 4-fluorophenyl group), 8.14 (2H, dd, J=8.2, 5.8 Hz, 2 and 6 positions of 4-fluorophenyl group), 8.33 (1H, s, 8 position of purine skeleton)

TOF-MS: 335 for $C_{19}H_{16}FN_4O$ (M+H)

HPLC (the same conditions as in Example 1): Purity: 96.1%, Retention time: 18.12 minutes

EXAMPLE 136

2-(3-Fluorophenyl)-7-(3-phenylpropyl)hypoxanthine

An amidation reaction and post-treatment were carried out following the conditions of Example 22, using 2.00 g (8.19 mmol) of 4-amino-1-(3-phenylpropyl)-5-imidazolecarboxamide prepared in the same manner as in Example 114 and 3-fluorobenzoyl chloride instead of benzoyl chloride to obtain 2.63 g of 4-(3-fluorobenzoylamino)-1-(3-phenylpropyl)-5-imidazolecarboxamide (yield 88%).

A cyclization reaction was carried out for 8.5 hours under the same conditions as in Example 1 using 2.56 g (6.99 mmol) of the amide obtained above. The resulting product was post-treated to obtain 1.80 g of 2-(3-fluorophenyl)-7-(3-phenylpropyl)hypoxanthine (yield 74%).

$^1$H-NMR (300 MHz, DMSO-d$_6$, δ ppm):

2.18 (2H, m, central (β-position) methylene of 3phenyl-propyl group), 2.59 (2H, t, J=6.9 Hz, phenyl group side (γ-position) methylene of 3-phenylpropyl group), 4.38 (2H, t, J=6.3 Hz, purin ring side (α-position) methylene of 3-phenylpropyl group), 7.12–7.29 (5H, m, aromatic H of 3-phenyl propyl group), 7.34–7.43 (1H, m, 5 position of 3-fluorophenyl group), 7.52–7.61 (1H, m, 4 position of 3-fluorophenyl group), 7.88–7.99 (2H, m, 2 and 6 positions of 3-fluorophenyl group), 8.28 (1H, s, 8 position of purine skeleton), 12.54 (1H, br. s, NH)

TOF-MS: 349 for $C_{20}H_{18}FN_4O$ (M+H)

HPLC (the same conditions as in Example 1): Purity: 97.3%, Retention time: 19.62 minutes

EXAMPLE 137

2-(4-Fluorophenyl)-7-(3-phenylpropyl) hypoxanthine

An amidation reaction and post-treatment were carried out following the conditions of Example 22, using 2.00 g (8.19 mmol) of 4-amino-1-(3-phenylpropyl)-5-imidazolecarboxamide prepared in the same manner as in Example 114 and 4-fluorobenzoyl chloride instead of benzoyl chloride to obtain 2.78 g of 4-(4-fluorobenzoylamino)-1-(3-phenylpropyl)-5-imidazolecarboxamide (yield 93%).

A cyclization reaction was carried out for 13 hours under the same conditions as in Example 1 using 2.70 g (7.37 mmol) of the amide obtained above. The resulting product was post-treated to obtain 2.18 g of 2-(4-fluorophenyl)-7-(3-phenylpropyl)hypoxanthine (yield 85%).

$^1$H-NMR (300 MHz, DMSO-d$_6$, δ ppm):

2.18 (2H, m, central (β-position) methylene of 3-phenylpropyl group), 2.59 (2H, t, J=7.3 Hz, phenyl group side (γ-position) methylene of 3-phenylpropyl group), 4.38 (2H, t, J=6.3 Hz, purin ring side (α-position) methylene of 3-phenylpropyl group), 7.09–7.29 (5H, m, aromatic H of 3-phenylpropyl group), 7.35 (2H, t-like, J=7.8 Hz, 3 and 5 positions of 4-fluorophenyl group), 8.15 (2H, dd, J=7.8, 4.6 Hz, 2 and 6 positions of 4-fluorophenyl group), 8.25 (1H, s, 8 position of purine skeleton), 12.49 (1H, br. s, NH)

TOF-MS: 349 for $C_{20}H_{18}FN_4O$ (M+H)

HPLC (the same conditions as in Example 1): Purity: 98.8%, Retention time: 19.34 minutes

EXAMPLE 138

7-(3-Dimethylaminobenzyl)-2-ethylhypoxanthine

An alkylation reaction, acid hydrolysis, and neutralization were carried out following the conditions of Reference Example 2, using 4.29 g (20.0 mmol) of 4-benzylideneamino-5-imidazolecarboxamide obtained in the same manner as in Reference Example 1 and 3-dimethylaminobenzyl chloride which was separately prepared according to a conventional method, instead of benzyl chloride, to obtain 3.51 g of 4-amino-1-(3-dimethylaminobenzyl)-5-imidazolecarboxamide (yield 68%, 3 steps).

An amidation reaction and post-treatment were carried out following the conditions of Example 21, using 2.00 g (7.71 mmol) of the amine produced above to obtain 2.03 g of 1-(3-dimethylaminobenzyl)-4-propanoylamino-5-imidazole carboxamide (yield 84%).

1.94 g (6.15 mmol) of the amide thus prepared was cyclized for 4 hours under the same conditions as in Example 1 and post-treated to obtain 1.66 g of 7-(3-dimethylaminobenzyl)-2-ethylhypoxanthine (yield 91%).

$^1$H-NMR (300 MHz, DMSO-d$_6$, δ ppm):

1.20 (3H, t, J=7.0 Hz, methyl of ethyl group), 2.59 (2H, q, J=6.8 Hz, methylene of ethyl group), 2.85 (6H, s, methyls of dimethylamino group), 5.43 (2H, s, methylene of 3-dimethylaminobenzyl group), 6.55–6.64 (2H, m, 4 and 6 positions of 3-dimethylaminobenzyl group), 6.83 (1H, br. s, 2 position of 3-dimethylaminobenzyl group), 7.10 (1H, t-like, J=6.9 Hz, 5 position of 3-dimethylaminobenzyl group), 8.29 (1H, s, 8 position of purine skeleton), 12.15 (1H, br. s, NH)

TOF-MS: 298 for $C_{16}H_{20}N_5O$ (M+H)

HPLC (the same conditions as in Example 1): Purity: 98.5%, Retention time: 10.46 minutes

EXAMPLE 139

7-Benzyl-2-(2-pyridyl)hypoxanthine

An amidation reaction and post-treatment were carried out following the conditions of Example 17, using 1.0 g (4.6 mmol) of 4-amino-1-benzyl-5-imidazolecarboxamide prepared in the same manner as in Reference Example 2 and picolinic acid instead of 3-pyridylacetic acid hydrochloride to obtain 1.29 g of 1-benzyl-4-(2-pyridylcarbonylamino)-5-imidazolecarboxamide (yield 87%).

A cyclization reaction was carried out for 4 hours under the same conditions as in Example 1 using 1.05 g (3.27 mmol) of the amide obtained above. The resulting product was post-treated to obtain 0.91 g of 7-benzyl-2-(2-pyridyl)hypoxanthine (yield 92%).

$^1$H-NMR (300 MHz, DMSO-d$_6$, δ ppm):

5.60 (2H, s, methylene of benzyl group), 7.27–7.40 (5H, m, aromatic H of benzyl group), 7.61 (1H, dd, J=6.9, 3.9 Hz, 4 position of 2-pyridyl group), 8.04 (1H, m, 5 position of 2-pyridyl group), 8.36 (1H, d, J=8.1 Hz, 6 position of 2-pyridyl group), 8.48 (1H, s, 8 position of purine skeleton), 8.71 (1H, d, J=4.5 Hz, 3 position of 2-pyridyl group), 11.78 (1H, br. s, NH)

TOF-MS: 304 for $C_{17}H_{14}N_5O$ (M+H)

HPLC (the same conditions as in Example 1): Purity: 95.4%, Retention time: 16.95 minutes

EXAMPLE 140

7-Benzyl-2-(4-pyridyl)hypoxanthine

An amidation reaction and post-treatment were carried out following the conditions of Example 19, using 1.00 g (4.62 mmol) of 4-amino-1-benzyl-5-imidazolecarboxamide prepared in the same manner as in Reference Example 2 and isonicotinic acid instead of cyclopentylacetic acid to obtain 1.16 g of 1-benzyl-4-(4-pyridylcarbonylamino)-5-imidazolecarboxamide (yield 78%).

A cyclization reaction was carried out for 4 hours under the same conditions as in Example 1 using 1.05 g (3.27 mmol) of the amide obtained above. The resulting product was post-treated to obtain 0.82 g of 7-benzyl-2-(4-pyridyl) hypoxanthine (yield 83%).

$^1$H-NMR (300 MHz, DMSO-d$_6$, δ ppm):

5.61 (2H, s, methylene of benzyl group), 7.22–7.45 (5H, m, aromatic H of benzyl group), 8.03 (2H, d, J=6.6 Hz, 2 and 6 positions of 4-pyridyl group), 8.46 (1H, s, 8 position of purine skeleton), 8.74 (2H, dd, J=4.5, 1.5 Hz, 3 and 5 positions of 4-pyridyl group), 12.72 (1H, br. s, NH)

TOF-MS: 304 for $C_{17}H_{14}N_5O$ (M+H)

HPLC (the same conditions as in Example 1): Purity: 98.0%, Retention time: 15.76 minutes

EXAMPLE 141

7-(4-Carboxybenzyl)-2-propylhypoxanthine

An alkylation reaction, acid hydrolysis, and neutralization were carried out following the conditions of Reference Example 2, using 3.13 g (14.6 mmol) of 4-benzylideneamino-5-imidazolecarboxamide obtained in the same manner as in Reference Example 1 and methyl 4-bromomethylbenzoate instead of benzyl chloride to obtain 3.61 g of 4-amino-1-(4-methoxycarbonylbenzyl)-5-imidazolecarboxamide (yield 90%, 3 steps).

An amidation reaction and post-treatment were carried out following the conditions of Example 21, using 1.30 g (4.74 mmol) of 4-amino-1-(4-methoxycarbonylbenzyl)-5-imidazole carboxamide produced above to obtain 1.40 g of 4-propanoylamino-1-(4-methoxycarbonylbenzyl)-5-imidazole carboxamide (yield 89%).

1.30 g (3.94 mmol) of the amide thus prepared was cyclized for 4 hours under the same conditions as in Example 1 and post-treated to obtain 0.95 g of 7-(4-carboxybenzyl)-2-propylhypoxanthine (yield 81%).

$^1$H-NMR (300 MHz, DMSO-d$_6$, δ ppm):

1.21 (3H, t, J=7.5 Hz, methyl of ethyl group), 2.61 (2H, q, J=7.5 Hz, methylene of ethyl group), 5.62 (2H, s, methylene of benzyl group), 7.35 (2H, d, J=12 Hz, 2 and 6 positions of 4-carboxybenzyl group), 7.87 (2H, d, J=12 Hz, 3 and 5 positions of 4-carboxybenzyl group), 8.28 (1H, s, 8 position of purine skeleton), 12.11 (1H, br. s, NH), 12.90 (1H, br. s, COOH)

TOF-MS: 299 for $C_{15}H_{15}N_4O_3$ (M+H)

HPLC (the same conditions as in Example 1): Purity: 92%, Retention time: 14.47 minutes

EXAMPLE 142

7-(2-Methylbenzyl)-2-phenylhypoxanthine

An amidation reaction and post-treatment were carried out following the conditions of Example 1, using 1.50 g (5.62 mmol) of 4-amino-1-(2-methylbenzyl)-5-imidazolecarboxamide hydrochloride prepared in the same manner as in Example 119 to obtain 0.69 g of 4-benzoylamino-1-(2-methylbenzyl)-5-imidazolecarboxamide (yield 37%).

A cyclization reaction was carried out for 8 hours under the same conditions as in Example 1 using 0.65 g (1.94 mmol) of the amide obtained above. The resulting product was post-treated to obtain 0.43 g of 7-(2-methylbenzyl)-2-phenylhypoxanthine (yield 70%).

$^1$H-NMR (300 MHz, DMSO-d6, δ ppm):

2.31 (3H, s, methyl of 2-methylbenzyl group), 5.63 (2H, s, methylene of 2-methylbenzyl group), 6.81 (1H, d, J=7.8 Hz, aromatic H of 2-methylbenzyl group), 7.10–7.25 (3H, m, aromatic H of 2-methylbenzyl group, phenyl group), 8.08 (2H, dd, J=7.2, 2.1 Hz, 2 and 6 positions of 2 position phenyl group), 8.23 (1H, s, 8 position of purine skeleton), 12.48 (1H, br. s, NH)

TOF-MS: 317 for $C_{19}H_{17}N_4O$ (M+H)

HPLC (the same conditions as in Example 1): Purity: 96.4%, Retention time: 18.49 minutes

EXAMPLE 143

7-(3,5-Dimethylbenzyl)-2-ethylhypoxanthine

An alkylation reaction, acid hydrolysis, and neutralization were carried out following the conditions of Reference Example 2, using 3.15 g (14.7 mmol) of 4-benzylideneamino-5-imidazolecarboxamide obtained in the same manner as in Reference Example 1 and 3,5-dimethylbenzyl chloride instead of benzyl chloride to obtain 2.28 g of 4-amino-1-(3,5-dimethylbenzyl)-5-imidazolecarboxamide (yield 63%, 3 steps).

An amidation reaction and post-treatment were carried out following the conditions of Example 21, using 1.28 g (5.24 mmol) of the amine produced above to obtain 1.18 g of 1-(3,5-dimethylbenzyl)-4-propanoylamino-5-imidazole carboxamide (yield 75%).

1.10 g (3.66 mmol) of the amide thus prepared was cyclized for 4 hours under the same conditions as in Example 1 and post-treated to obtain 0.84 g of 7-(3,5-dimethylbenzyl)-2-ethylhypoxanthine (yield 81%).

$^1$H-NMR (300 MHz, DMSO-d$_6$, δ ppm):

1.20 (3H, t, J=7.4 Hz, methyl of ethyl group), 2.21 (6H, s, methyl groups of 3,5-dimethylbenzyl), 2.60 (2H, q, J=7.4 Hz, methylene of ethyl group), 5.54 (2H, s, methylene of 3,5-dimethylbenzyl group), 6.89 (1H, s, 4 position of 3,5-dimethylbenzyl group), 6.93 (2H, s, 2 and 6 positions of 3,5-dimethylbenzyl group), 8.27 (1H, s, 8 position of purine skeleton), 12.20 (1H, br. s, NH)

TOF-MS: 283 for $C_{16}H_{19}N_4O$ (M+H)

HPLC (the same conditions as in Example 1): Purity: 90%, Retention time: 17.47 minutes

EXAMPLE 144

2-Ethyl-7-(2-naphthylmethyl)hypoxanthine

An alkylation reaction, acid hydrolysis, and neutralization were carried out following the conditions of Reference Example 2, using 2.14 g (9.99 mmol) of 4-benzylideneamino-5-imidazolecarboxamide obtained in the same manner as in Reference Example 1 and 2-chloromethylnaphthalene instead of benzyl chloride to obtain 1.12 g of 4-amino-1-(2-naphthylmethyl)-5-imidazolecarboxamide (yield 42%, 3 steps).

An amidation reaction and post-treatment were carried out following the conditions of Example 21, using 1.00 g (3.76 mmol) of the amine produced above to obtain 0.83 g of 1-(2-naphthylmethyl)-4-propanoylamino-5-imidazolecarboxamide (yield 68%).

0.80 g (2.5 mmol) of the amide thus prepared was cyclized for 2 hours under the same conditions as in Example 1 and post-treated to obtain 0.73 g of 2-ethyl-7-(2-naphthylmethyl)hypoxanthine (yield 97%).

$^1$H-NMR (300 MHz, DMSO-d$_6$, δ ppm):

1.19 (3H, t, J=7.7 Hz, methyl of ethyl group), 2.59 (2H, q, J=7.7 Hz, methylene of ethyl group), 5.54 (2H, s, methylene of naphthylmethyl group), 7.47–7.52 (3H, m, 3, 6 and 7 positions of naphthyl group), 7.79–7.89 (4H, m, 1, 4, 5 and 8 positions of naphthyl group), 8.36 (1H, s, 8 position of purine skeleton), 12.16 (1H, br. s, NH)

TOF-MS: 305 for $C_{18}H_{17}N_4O$ (M+H)

HPLC (the same conditions as in Example 1): Purity: 98%, Retention time: 17.71 minutes

EXAMPLE 145

7-Benzyl-2-(4-(N-methylamino)phenyl)hypoxanthine

An amidation reaction and post-treatment were carried out following the conditions of Example 17, using 2.16 g (9.99 mmol) of 4-amino-1-benzyl-5-imidazolecarboxamide prepared in the same manner as in Reference Example 2 and, instead of 3-pyridylacetic acid hydrochloride, 4-(N-t-butyloxycarbonyl-N-methylamino)benzoic acid which was prepared separately by a conventional method, to obtain 3.10 g of 1-benzyl-4-(4-(N-t-butyloxycarbonyl-N-methylamino) benzoylamino)-5-imidazolecarboxamide (yield 69%).

A cyclization reaction was carried out for 9 hours under the same conditions as in Example 1 using 3.10 g (6.90 mmol) of the amide obtained above. The resulting product was post-treated to obtain 2.60 g of 7-benzyl-2-(4-(N-t-butyloxycarbonyl-N-methylamino)phenyl)hypoxanthine (yield 87%).

2.59 g (6.00 mmol) of the carbamate thus prepared was treated with 18 ml of trifluoroacetic acid, followed by neutralization to obtain 1.96 g of 7-benzyl-2-(4-(N-methylamino)phenyl)hypoxanthine (yield 98%).

$^1$H-NMR (270 MHz, DMSO-d$_6$, δ ppm):

2.74 (3H, s, N-methyl group), 5.56 (2H, s, methylene of benzyl group), 6.32 (1H, br. s, NH of methylamino group), 6.59 (2H, d, J=8.7 Hz, 3 and 5 positions of 4-methylaminophenyl group), 7.25–7.39 (5H, m, benzyl group), 7.92 (2H, d, J=8.7 Hz, 2 and 6 positions of 4-methylaminophenyl group), 8.34 (1H, s, 8 position of purine skeleton), 12.08 (1H, br. s, NH)

TOF-MS: 332 for $C_{19}H_{18}N_5O$ (M+H)

HPLC (the same conditions as in Example 1): Purity: 100%, Retention time: 15.26 minutes

EXAMPLE 146

7-(3-Phenylpropyl)-2-propylhypoxanthine

An amidation reaction and post-treatment were carried out following the conditions of Example 21, using 2.00 g (8.19 mmol) of 4-amino-1-(3-phenylpropyl)-5-imidazolecarboxamide prepared in the same manner as in Example 114 and butanyric anhydride instead of propionic anhydride to obtain 2.48 g of 4-butanoylamino-1-(3-phenylpropyl)-5-imidazole carboxamide (yield 96%).

A cyclization reaction was carried out for 3 hours under the same conditions as in Example 1 using 2.47 g (7.86 mmol) of the amide obtained above. The resulting product was post-treated to obtain 1.50 g of 7-(3-phenylpropyl)-2-propylhypoxanthine (yield 64%)

$^1$H-NMR (270 MHz, DMSO-d$_6$, δ ppm):

0.90 (3H, t, J=7.3 Hz, methyl of propyl group), 1.70 (2H, tq, J=7.3, 7.3 Hz, 2 position methylene of propyl group), 2.13 (2H, tt, J=7.3, 7.3 Hz, 2 position methylene of phenylpropyl group), 2.51–2.58 (4H, m, 1 position methylene of propyl group, 3 position methylene of phenylpropyl group), 4.32 (2H, t, J=7.3 Hz, 1 position methylene of phenylpropyl group), 7.13–7.29 (5H, m, phenyl group), 8.16 (1H, s, 8 position of purine skeleton), 12.14 (1H, br. s, NH)

TOF-MS: 297 for $C_{17}H_{21}N_4O$ (M+H)

HPLC (the same conditions as in Example 1): Purity: 99%, Retention time: 17.40 minutes

EXAMPLE 147

7-(4-t-Butylbenzyl)-2-propylhypoxanthine

An amidation reaction and post-treatment were carried out following the conditions of Example 21, using 2.45 g (9.00 mmol) of 4-amino-1-(4-t-butylbenzyl)-5-imidazolecarboxamide prepared in the same manner as in Example 57 and butanyric anhydride instead of propionic anhydride to obtain 2.07 g of 4-butanoylamino-1-(4-t-butylbenzyl)-5-imidazole carboxamide (yield 67%).

A cyclization reaction was carried out for 8 hours under the same conditions as in Example 1 using 2.06 g (6.02 mmol) of the amide obtained above. The resulting product was post-treated to obtain 1.78 g of 7-(4-t-butylbenzyl)-2-propylhypoxanthine (yield 89%).

$^1$H-NMR (270 MHz, DMSO-d$_6$, δ ppm):

0.90 (3H, t, J=7.3 Hz, methyl of propyl group), 1.23 (9H, s, methyls of t-butyl group), 1.69 (2H, tq, J=7.3, 7.3 Hz, 2 position methylene of propyl group), 2.55 (2H, t, J=7.3 Hz, 1 position methylene of propyl group), 5.48 (2H, s, methylene of benzyl group), 7.27 (2H, d, J=8.6 Hz, 3 and 5 positions of 4-t-butylbenzyl group), 7.35 (2H, d, J=8.6 Hz, 2 and 6 positions of 4-t-butylbenzyl group), 8.31 (1H, s, 8 position of purine skeleton), 12.13 (1H, br. S, NH)

TOF-MS: 325 for $C_{19}H_{25}N_4O$ (M+H)

HPLC (the same conditions as in Example 1): Purity: 91%, Retention time: 17.83 minutes

EXAMPLE 148

7-(4-Fluorobenzyl)-2-propylhypoxanthine

An amidation reaction and post-treatment were carried out following the conditions of Example 21, using 2.0 g (8.5 mmol) of 4-amino-1-(4-fluorobenzyl)-5-imidazolecarboxamide prepared in the same manner as in Example 58 and butanyric anhydride instead of propionic anhydride to obtain 1.62 g of 4-butanoylamino-1-(4-fluorobenzyl)-5-imidazolecarboxamide (yield 63%).

A cyclization reaction was carried out for 3.5 hours under the same conditions as in Example 1 using 1.61 g (5.29 mmol) of the amide obtained above. The resulting product was post-treated to obtain 1.35 g of 7-(4-fluorobenzyl)-2-propylhypoxanthine (yield 89%).

$^1$H-NMR (270 MHz, DMSO-$d_6$, δ ppm):

0.89 (3H, t, J=7.3 Hz, methyl of propyl group), 1.69 (2H, tq, J=7.3, 7.3 Hz, 2 position methylene of propyl group), 2.55 (2H, t, J=7.3 Hz, 1 position methylene of propyl group), 5.51 (2H, s, methylene of 4-fluorobenzyl group), 7.24 (2H, t, J=8.7 Hz, 3 and 5positions of 4-fluorobenzyl group), 7.45 (2H, dd, J=8.6, 6.0 Hz, 2 and 6 positions of 4-fluorobenzyl group), 8.33 (1H, s, 8 position of purine skeleton), 12.15 (1H, br. s, NH)

TOF-MS: 287 for $C_{15}H_{16}FN_4O$ (M+H)

HPLC (the same conditions as in Example 1): Purity: 94%, Retention time: 16.66 minutes

EXAMPLE 149

7-(3-Fluorobenzyl)-2-propylhypoxanthine

An amidation reaction and post-treatment were carried out following the conditions of Example 21, using 5.15 g (21.9 mmol) of 4-amino-1-(3-fluorobenzyl)-5-imidazolecarboxamide prepared in the same manner as in Example 82 and butanyric anhydride instead of propionic anhydride to obtain 6.25 g of 4-butanoylamino-1-(3-fluorobenzyl)-5-imidazole carboxamide (yield 94%).

A cyclization reaction was carried out for 2 hours under the same conditions as in Example 1 using 6.20 g (20.4 mmol) of the amide obtained above. The resulting product was post-treated to obtain 5.38 g of 7-(3-fluorobenzyl)-2-propylhypoxanthine (yield 92%).

$^1$H-NMR (270 MHz, DMSO-$d_6$, δ ppm):

0.90 (3H, t, J=7.4 Hz, methyl of propyl group), 1.70 (2H, tq, J=7.5, 7.4 Hz, 2 position methylene of propyl group), 2.56 (2H, to J=7.5 Hz, 1 position methylene of propyl group), 5.50 (2H, s, methylene of benzyl group), 7.09–7.24 (3H, m, 3-fluorobenzyl group), 7.34–7.44 (1H, m, 3-fluorobenzyl group), 8.35 (1H, s, 8 position of purine skeleton), 12.15 (1H, br. s, NH)

TOF-MS: 287 for $C_{15}H_{16}FN_4O$ (M+H)

HPLC (the same conditions as in Example 1): Purity: 98%, Retention time: 18.55 minutes

EXAMPLE 150

7-(4-t-Butylbenzyl)-2-(4-pyridyl)hypoxanthine

An amidation reaction and post-treatment were carried out following the conditions of Example 1, using 1.63 g (5.28 mmol) of 4-amino-1-(4-t-butylbenzyl)-5-imidazolecarboxamide hydrochloride prepared in the same manner as in Example 57 and, instead of benzoyl chloride, isonicotinic chloride which was prepared separately by a conventional method, to obtain 1.78 g of 1-(4-t-butylbenzyl)-4-(4-pyridylcarbonylamino)-5-imidazolecarboxamide (yield 89%).

A cyclization reaction was carried out for 6 hours under the same conditions as in Example 1 using 1.77 g (4.69 mmol) of the amide obtained above. The resulting product was post-treated to obtain 1.25 g of 7-(4-t-butylbenzyl)-2-(4-pyridyl)hypoxanthine (yield 74%).

$^1$H-NMR (270 MHz, DMSO-$d_6$, δ ppm):

1.23 (9H, s, methyls of t-butyl group), 5.57 (2H, s, methylene of 4-t-butylbenzyl group), 7.31 (2H, d, J=8.6 Hz, 3 and 5 positions of 4-t-butylbenzyl group), 7.36 (2H, d, J=8.6 Hz, 2 and 6 positions 4-t-butylbenzyl group), 8.05 (2H, dd, J=4.4, 1.6 Hz, 2 and 6 positions of 4-pyridyl group), 8.40 (1H, s, 8 position of purine skeleton), 8.72 (2H, dd, J=4.4, 1.6 Hz, 3 and 5 positions of 4-pyridyl group), 12.74 (1H, br. s, NH)

TOF-MS: 360 for $C_{21}H_{22}N_5O$ (M+H)

HPLC (the same conditions as in Example 1): Purity: 97%, Retention time: 18.58 minutes

EXAMPLE 151

7-(4-Fluorobenzyl)-2-(4-pyridyl)hypoxanthine

An amidation reaction and post-treatment were carried out under the same conditions as in Example 19, using 2.0 g (8.5 mmol) of 4-amino-1-(4-fluorobenzyl)-5-imidazolecarboxamide which was prepared in the same manner as in Example 58 and isonicotinic acid instead of cyclopentylacetic acid to obtain 1.87 g of 1-(4-fluorobenzyl)-4-(4-pyridylcarbonylamino)-5-imidazolecarboxamide (yield 65%).

A cyclization reaction was carried out under the same conditions as in Example 1 for 5 hours and 20 minutes using 1.87 g (5.51 mmol) of the amide obtained above. The resulting product was post-treated to obtain 1.32 g of 7-(4-fluorobenzyl)-2-(4-pyridyl)hypoxanthine (yield 75%).

¹H-NMR (300 MHz, DMSO-d$_6$, δ ppm):

5.58 (2H, s, methylene of 4-fluorobenzyl group), 7.18 (2H, t, J=8.7 Hz, 3 and 5 positions of 4-fluorobenzyl group), 7.45 (2H, dd, J=8.7, 6.0 Hz, 2 and 6 positions of 4-fluorobenzyl group), 8.02 (2H, d, J=6.0 Hz, 2 and 6 positions of 4-pyridyl group), 8.46 (1H, s, 8 position of purine skeleton), 8.73 (2H, d, J=6.0 Hz, 3 and 5 positions of 4-pyridyl group), 12.76 (1H, br. s, NH)

TOF-MS: 322 for C$_{17}$H$_{13}$FN$_5$O (M+H)

HPLC (the same conditions as in Example 1): Purity: 90.9%, Retention time: 16.32 minutes

EXAMPLE 152

2-Ethyl-7-(4-(2-tetrazolylphenyl)benzyl)hypoxanthine

An alkylation reaction, acid hydrolysis, and neutralization were carried out following the conditions of Reference Example 2, using 2.36 g (11.0 mmol) of 4-benzylideneamino-5-imidazolecarboxamide obtained in the same manner as in Reference Example 1 and 41-bromomethyl-2-cyanobiphenyl instead of benzyl chloride to obtain 2.38 g of 4-amino-1-(4-(2-cyanophenyl)benzyl)-5-imidazole carboxamide (yield 68%, 3 steps).

An amidation reaction and post-treatment were carried out following the conditions of Example 21, using 2.00 g (6.30 mmol) of the amine produced above to obtain 2.24 g of 1-(4-(2-cyanophenyl)benzyl)-4-propanoylamino-5-imidazole carboxamide (yield 95%).

2.17 g (5.81 mmol) of the amide thus prepared was suspended in 30 ml of toluene and 5.00 g (24.3 mmol) of trimethyl tin azide was added to the suspension, followed by heating for 23 hours while refluxing. Crystals produced was separated by filtration and dissolved in methanol containing 1N hydrochloric acid. The solution was neutralized with 4 N sodium hydroxide aqueous solution. After evaporating methanol, crystals collected by filtration was purified by suspending them in hot methanol, thereby obtaining 1.93 g of 2-ethyl-7-(4-2-tetrazolylphenyl)benzyl)hypoxanthine (yield 83%).

¹H-NMR (300 MHz, DMSO-d$_6$, δ ppm):

0.95 (3H, t, J=7.2 Hz, methyl of ethyl group), 2.35 (2H, q, J=7.2 Hz, methylene of ethyl group), 5.24 (2H, s, methylene of benzyl group), 6.78 (2H, d, J=8.1 Hz, 3 and 5 positions of benzyl group), 7.01 (2H, d, J=8.1 Hz, 2 and 6 positions of benzyl group), 7.16–7.30 (4H, m, tetrazolylphenyl group), 8.05 (1H, s, 8 position of purine skeleton), 11.88 (1H, br. s, NH)

TOF-MS: 399 for C$_{21}$H$_{19}$N$_8$O (M+H)

HPLC (the same conditions as in Example 1): Purity: 94%, Tamotsu poetic time 17.78 minutes

EXAMPLE 153

7-(4-t-Butylbenzyl)-2-(3-(N-methylamino)phenyl)hypoxanthine

An amidation reaction and post-treatment were carried out under the same conditions as in Example 17, using 4.31 g (14.0 mmol) of 4-amino-1-(4-t-butylbenzyl)-5-imidazolecarboxamide which was prepared in the same manner as in Example 57 and 3-(N-t-butyloxycarbonyl-N-methylamino)benzoic acid instead of 3-pyridylacetic acid hydrochloride to obtain 4.59 g of 1-(4-t-butylbenzyl)-4-(3-(N-t-butyloxycarbonyl-N-methylamino)benzoylamino)-5-imidazolecarboxamide (yield 65%).

A cyclization reaction was carried out under the same conditions as in Example 1 for 10 hours using 4.58 g (9.06 mmol) of the amide obtained above. The resulting product was post-treated to obtain 3.18 g of 7-(4-t-butylbenzyl)-2-(3-(N-t-butyloxycarbonyl-N-methylamino)phenyl)hypoxanthine (yield 72%).

3.18 g (6.52 mmol) of the carbamate thus prepared was treated with 19.6 ml of trifluoroacetic acid and neutralized to obtain 1.93 g of 7-(4-t-butylbenzyl)-2-(3-(N-methylamino)phenyl)hypoxanthine (yield 76%)

¹H-NMR (270 MHz, DMSO-d$_6$, δ ppm):

1.24 (9H, s, methyls of t-butyl group), 2.74 (3H, d, J=4.8 Hz, N-methyl group), 5.54 (2H, s, methylene of 4-t-butylbenzyl group), 5.88 (1H, d, J=4.8 Hz, NH of methylamino group), 6.69–6.72 (1H, m, 4 position of 3-methylaminophenyl group), 7.16–7.26 (3H, m, 2, 5 and 6 positions of 3-methylaminophenyl group), 7.31 (2H, d, J=8.5 Hz, 3 and 5 positions of 4-t-butylbenzyl group), 7.37 (2H, d, J=8.5 Hz, 2 and 6 positions of 4-t-butylbenzyl group), 8.39 (1H, s, 8 positions of purine skeleton), 12.32 (1H, br. s, NH)

TOF-MS: 388 for C$_{23}$H$_{26}$N$_5$O (M+H)

HPLC (the same conditions as in Example 1): Purity: 99.6%, Retention time: 19.40 minutes

EXAMPLE 154

7-(4-t-Butylbenzyl)-2-(4-(N-methylamino)phenyl)hypoxanthine

An amidation reaction and post-treatment were carried out under the same conditions as in Example 19, using 2.65 g (9.71 mmol) of 4-amino-1-(4-t-butylbenzyl)-5-imidazolecarboxamide which was prepared in the same manner as in Example 57 and 4-(N-t-butyloxycarbonyl-N-methylamino)benzoic acid which was prepared seperately by a conventional method instead of cyclopentyl acetic acid to obtain 2.69 g of 1-(4-t-butylbenzyl)-4-(4-(N-t-butyloxycarbonyl-N-methylamino)benzoylamino)-5-imidazolecarboxamide (yield 55%).

A cyclization reaction was carried out under the same conditions as in Example 1 for 11 hours and 40 minutes using 2.69 g (5.30 mmol) of the amide obtained above. The resulting product was post-treated to obtain 2.04 g of 7-(4-t-butylbenzyl)-2-(4-(N-t-butyloxycarbonyl-N-methylamino)-phenyl)hypoxanthine (yield 79%).

1.98 g (4.07 mmol) of the carbamate obtained above was treated with 12.2 ml of trifluoroacetic acid and neutralized to obtain 1.46 g of 7-(4-t-butylbenzyl)-2-(4-(N-methylamino)phenyl)hypoxanthine (yield 93%).

¹H-NMR (270 MHz, DMSO-d$_6$, δ ppm):

1.23 (9H, s, methyls of t-butyl group), 2.74 (3H, d, J=4.9 Hz, N-methyl), 5.51 (2H, s, methylene of 4-t-butylbenzyl group), 6.31 (1H, q, J=4.9 Hz, NH), 6.59 (2H, d, J=8.6 Hz, 3 and 5 positions of 4-methylaminophenyl group), 7.30 (2H, d, J=8.4 Hz, 3 and 5 positions of 4-t-butylbenzyl group), 7.36 (2H, d, J=8.4 Hz, 2 and 6 positions of 4-t-butylbenzyl group), 7.92 (2H, d, J=8.6 Hz, 2 and 6 positions of 4-methylaminophenyl group), 8.33 (1H, s, 8 positions of purine skeleton), 12.01 (1H, br. s, amide NH)

TOF-MS: 388 for $C_{23}H_{26}N_5O$ (M+H)

HPLC (the same conditions as in Example 1): Purity: 98.1%, Retention time: 19.98 minutes

EXAMPLE 155

2-Ethyl-7-(2-phenoxyethyl)hypoxanthine

An alkylation reaction, acid hydrolysis, and neutralization were carried out following the conditions of Reference Example 2, using 2.00 g (9.33 mmol) of 4-benzylideneamino-5-imidazolecarboxamide obtained in the same manner as in Reference Example 1 and 2-bromophenetole instead of benzyl chloride to obtain 1.77 g of 4-amino-1-(2-phenoxyethyl)-5-imidazolecarboxamide (yield 77%, 3 steps).

An amidation reaction and post-treatment were carried out following the conditions of Example 21, using 0.50 g (2.0 mmol) of the amine produced above to obtain crude 1-(2-phenoxyethyl)-4-propanoylamino-5-imidazolecarboxamide.

A cyclization reaction was carried out under the same conditions as in Example 1 for 3 hours using the crude amide obtained above. The resulting product was post-treated to obtain 0.37 g of 2-ethyl-7-(2-phenoxyethyl)hypoxanthine (yield 64%, 2 steps).

$^1$H-NMR (300 MHz, DMSO-$d_6$, δ ppm):

1.20 (3H, t, J=7.6 Hz, methyl of ethyl group), 2.60 (2H, q, J=7.6 Hz, methylene of ethyl group), 4.35 (2H, m, purine ring side (1 position) methylene of 2-phenoxyethyl group), 4.68 (2H, m, phenoxy group side (2 position) methylene of 2-phenoxyethyl group), 6.87–6.96 (3H, m, 2, 4 and 6 positions of phenoxy group), 7.21–7.29 (2H, m, 3 and 5 positions of phenoxy group), 8.20 (1H, s, 8 positions of purine skeleton), 12.20 (1H, br. s, NH)

TOF-MS: 285 for $C_{15}H_{17}N_4O_2$ (M+H)

HPLC (the same conditions as in Example 1): Purity: 99.1%, Retention time: 15.04 minutes

EXAMPLE 156

2-Ethyl-7-(3-phenoxypropyl hypoxanthine

An alkylation reaction, acid hydrolysis, and neutralization were carried out following the conditions of Reference Example 2, using 2.02 g (9.43 mmol) of 4-benzylideneamino-5-imidazolecarboxamide obtained in the same manner as in Reference Example 1 and 3-bromo-1-phenoxypropane instead of benzyl chloride to obtain 2.00 g of 4-amino-1-(3-phenoxypropyl)-5-imidazolecarboxamide (yield 81%, 3 steps).

An amidation reaction and post-treatment were carried out following the conditions of Example 21, using 0.50 g (1.9 mmol) of the amine produced above to obtain crude 1-(3-phenoxypropyl)-4-propanoylamino-5-imidazolecarboxamide.

A cyclization reaction was carried out under the same conditions as in Example 1 for 3 hours using the crude amide obtained above. The resulting product was post-treated to obtain 0.47 g of 2-ethyl-7-(3-phenoxypropyl)hypoxanthine (yield 82%, 2 steps).

$^1$H-NMR (300 MHz, DMSO-$d_6$, δ ppm):

1.20 (3H, t, J=7.6 Hz, methyl of ethyl group), 2.28 (2H, t-like, J=6.1 Hz, central methylene of 3-phenoxypropyl group), 2.60 (2H, q, J=7–5 Hz, methylene of ethyl group), 3.92 (2H, m, purine ring side (1 position) methylene of 3-phenoxypropyl group), 4.46 (2H, m, phenoxy group side (2 position) methylene of 3-phenoxypropyl group), 6.82–6.95 (3H, m, 2, 4 and 6 positions of phenoxy group), 7.21–7.29 (2H, m, 3 and 5 positions of phenoxy group), 8.13 (1H, s, 8 positions of purine skeleton), 12.14 (1H, br. s, NH)

TOF-MS: 299 for $C_{16}H_{19}N_4O_2$ (M+H)

HPLC (the same conditions as in Example 1): Purity: 99.6%, Retention time: 15.38 minutes

EXAMPLE 157

2-(2-Fluorophenyl)-7-(2-phenoxyethyl)hypoxanthine

An amidation reaction and post-treatment were carried out following the conditions of Example 22, using 1.00 g (4.06 mmol) of 4-amino-1-(2-phenoxyethyl)-5-imidazolecarboxamide prepared in the same manner as in Example 155 and 2-fluorobenzoyl chloride instead of benzoyl chloride to obtain 1.39 g of 4-(2-fluorobenzoylamino)-1-(2-phenoxyethyl)-5-imidazolecarboxamide (yield 93%).

A cyclization reaction was carried out for 13 hours under the same conditions as in Example 1 using 1.25 g (3.39 mmol) of the amide obtained above. The resulting product was post-treated to obtain 0.88 g of 2-(2-fluorophenyl)-7-(2-phenoxyethyl)hypoxanthine (yield 75%).

$^1$H-NMR (270 MHz, DMSO-$d_6$, δ ppm):

4.40 (2H, m, purine ring side methylene of 2-phenoxyethyl group), 4.75 (2H, m, phenoxy group side methylene of 2-phenoxyethyl group), 6.90–6.96 (3H, m, 2, 4 and 6positions of phenoxy group), 7.23–7.41 (4H, m, 3 and 5 positions of phenoxy group, 3 and 5 positions of 2-fluorophenyl group), 7.54–7.64 (1H, m, 4 position of 2-fluorophenyl group), 7.67–7.75 (1H, m, 6 position of 2-fluorophenyl group), 8.33 (1H, s, 8 positions of purine skeleton), 12.62 (1H, br. s, NH)

TOF-MS: 351 for $C_{19}H_{16}FN_4O_2$ (M+H)

HPLC (the same conditions as in Example 1): Purity: 98.2%, Retention time: 17.47 minutes

EXAMPLE 158

2-(2-Fluorophenyl)-7-(3-phenoxypropyl) hypoxanthine

An amidation reaction and post-treatment were carried out following the conditions of Example 22, using 1.00 g (3.84 mmol) of 4-amino-1-(3-phenoxypropyl)-5-imidazolecarboxamide prepared in the same manner as in Example 156 and 2-fluorobenzoyl chloride instead of benzoyl chloride to obtain 1.35 g of 4-(2-fluorobenzoylamino)-1-(3-phenoxypropyl)-5-imidazolecarboxamide (yield 92%).

A cyclization reaction was carried out for 13 hours under the same conditions as in Example 1 using 1.26 g (3.30 mmol) of the amide obtained above. The resulting product was post-treated to obtain 0.95 g of 2-(2-fluorophenyl)-7-(3-phenoxypropyl)hypoxanthine (yield 79%).

$^1$H-NMR (270 MHz, DMSO-$d_6$, δ ppm):

2.33 (2H, t-like, J=6.1 Hz, central (β-position) methylene of 3-phenoxypropyl group), 3.97 (2H, t, J=5.7 Hz, purine ring side (α-position) methylene of 3-phenoxypropyl group), 4.53 (2H, t, J=6.6 Hz, phenoxy group side (γ-position) methylene of 3-phenoxypropyl group), 6.84–6.96 (3H, m, 2, 4 and 6 positions of phenoxy group), 7.22–7.41 (4H, m, 3 and 5 positions of phenoxy group, 3 and 5 positions of 2-fluorophenyl group), 7.55–7.64 (1H, m, 4 position of 2-fluorophenyl group), 7.67–7.75 (1H, m, 6 position of 2-fluorophenyl group), 8.26 (1H, s, 8 position of purine skeleton), 12.57 (1H, br. s, NH)

TDF-MS: 365 for $C_{20}H_{18}FN_4O_2$ (M+H)

HPLC (the same conditions as in Example 1): Purity: 98.5%, Retention time: 18.37 minutes The pharmacological effect of the purine derivative of the present invention will now be illustrated by way of test examples.

Test Example 1

(Effect on the anti-GBM nephritis model of rat, intraperitoneal administration)

To demonstrate the effect of the purine derivatives of the present invention in the suppression of nephritis, the controlling effect on the anti-GBM nephritis model using rat which is a pharmacological model of glomerulone-nephritis was evaluated according to the following method.

In this evaluation, anti-GBM nephritis was induced in Wistar male rats, aged 8 weeks, by administering rabbit serum containing an anti-rat glomerulus basilar membrane antibody (anti-GBM serum). The anti-GBM serum used was prepared according to the method described in *Kidney and Dialysis*, Vol. 31, Extra Edition, pp 202–206 (1991). The anti-GBM serum was intravenously administered at a dose of 0.125 ml/300 g . A prescribed amount (per weight of animals) of the test compound, suspended in a 0.5% CMC-Na aqueous solution was intraperitoneally administered once a day for 5 days starting from the day on which the nephritis was induced (i.e. the day on which anti-GBM serum was administered). The same amount of 0.5% CMC-Na aqueous solution not containing the test compound was administered to animals of a control group. In order to measure the amount of proteins in the urine, samples were collected every 24 hours during the administration of the test compound.

The controlling effect on the anti-GBM nephritis was evaluated from the amount of proteins in the urine when the dose of the test compound per weight was 30 mg/kg. The results for the compounds prepared in Examples 1, 7, 9, 16, 21, 22, 23, 24, 26, 27, 30, 34, 44, 47, 54, 81, 82, 87, 88, 102, 133, 140, and 141 are shown in Table 1. Suppression of a proteinuria increase in tested animals as compared with animals of the control group to which no test compound was administered was clearly shown. The amount of proteins in the urine of the control groups fluctuated in each experiment. Therefore, a mean value is shown in Table 1 for control groups.

TABLE 1

|  | Urine protein (Fourth day) (mg/d1) | Urine (Fourth day) ml |
| --- | --- | --- |
| Control group | 123.6 ± 12.8 | 11.1 ± 0.7 |
| Compound of Example 1 | 24.4 ± 7.2 | 12.6 ± 2.3 |
| Compound of Example 7 | 23.7 ± 6.4 | 8.8 ± 1.2 |
| Compound of Example 9 | 21.7 ± 6.4 | 9.1 ± 0.3 |
| Compound of Example 16 | 10.5 ± 1.0 | 8.9 ± 0.7 |
| Compound of Example 21 | 16.3 ± 4.4 | 7.9 ± 1.3 |
| Compound of Example 22 | 34.2 ± 8.9 | 11.0 ± 0.8 |
| Compound of Example 23 | 36.6 ± 6.1 | 9.5 ± 0.3 |
| Compound of Example 24 | 85.3 ± 11.1 | 10.6 ± 0.9 |
| Compound of Example 26 | 65.9 ± 18.9 | 10.8 ± 0.3 |
| Compound of Example 27 | 15.3 ± 3.1 | 12.6 ± 1.4 |
| Compound of Example 30 | 59.4 ± 20.6 | 10.7 ± 0.5 |
| Compound of Example 34 | 48.1 ± 13.4 | 13.0 ± 4.6 |
| Compound of Example 44 | 51.4 ± 3.3 | 13.1 ± 0.7 |
| Compound of Example 47 | 39.2 ± 5.6 | 11.1 ± 0.5 |
| Compound of Example 54 | 61.5 ± 13.7 | 9.5 ± 0.9 |
| Compound of Example 81 | 9.7 ± 3.5 | 10.0 ± 1.7 |
| Compound of Example 82 | 32.2 ± 9.9 | 11.4 ± 0.3 |
| Compound of Example 87 | 15.6 ± 4.7 | 10.4 ± 0.9 |
| Compound of Example 88 | 38.6 ± 14.1 | 11.9 ± 1.6 |
| Compound of Example 102 | 66.7 ± 20.5 | 12.3 ± 0.6 |
| Compound of Example 133 | 55.1 ± 19.9 | 10.7 ± 1.4 |
| Compound of Example 140 | 35.4 ± 11.3 | 13.7 ± 1.8 |
| Compound of Example 141 | 60.7 ± 11.7 | 13.3 ± 1.5 |
| Theophylline | 68.3 ± 11.5 | 16.4 ± 3.8 |

(The figures indicate mean value ± standard error.)

Theophylline which is a non-selective phosphodiesterase (PDE) inhibitor was administered as a positive control substance. Although the amount of urine proteins was somewhat controlled in this group, a remarkable increase in the amount of urine was seen. Because of the fact that no increase in the amount of urine was seen in the groups to which the test compounds were administered, the anti-nephritis effect of the test compounds is not presumed to be induced by a protective action due to an increase in the kidney blood flow rate as in the case of the theophylline which is a PDE inhibitor.

Test Example 2

(Effect on the Masugi nephritis model of rat, oral administration)

To demonstrate the effect of the purine derivatives of the present invention by oral administration, the controlling effect on the anti-GBM nephritis model of rat was evaluated in the same manner as in the Test Example 1, with the exception that the test compounds were orally administered.

A 50 mg/kg dose of the test compound, suspended in a 0.5% CMC-Na aqueous solution, was orally administered twice a day for 5 days starting from the day on which the nephritis was induced (i.e. the day on which the anti-GBM serum was administered). The same amount of 0.5% CMC-Na aqueous solution not containing the test compound was administered to animals of a control group. Urine was collected every 24 hours during administration of the test compound to measure the amount of proteins in the urine.

The results for the compounds prepared in Examples 21, 113, 129, 131, 135, and 148 are shown in Table 2. Suppression of a urine protein increase in tested animals as compared with animals of the control group to which no test compound was administered was clearly shown. The mean value of the amount of proteins in the urine of the control group is shown in Table 2, because such an amount fluctuated by experiment.

TABLE 2

|  | Urine protein (Fourth day) (mg/d1) | Body weight relative to day 0 (Sixth day) (%) |
| --- | --- | --- |
| Control group | 135.3 ± 15.1 | 116.7 ± 0.9 |
| Compound of Example 21 | 59.4 ± 17.6 | 115.9 ± 1.2 |
| Compound of Example 113 | 66.7 ± 17.4 | 112.5 ± 0.9 |
| Compound of Example 129 | 37.8 ± 11.5 | 116.4 ± 0.6 |
| Compound of Example 131 | 58.1 ± 5.6 | 111.4 ± 2.0 |
| Compound of Example 135 | 56.9 ± 21.3 | 112.3 ± 2.8 |
| Compound of Example 148 | 76.0 ± 17.6 | 116.5 ± 0.8 |
| Compound of JPA 7-316158 | 62.1 ± 18.1 | 103.7 ± 3.0 |

(The figures indicate mean value ± standard error.)

A typical -compound described in Japanese Patent Application Laid-Open No. 7-316158, 2-(4-hydroxy-3,5-di-t-butylphenyl)-6-propoxypurine, was administered as a positive control substance. Although the same degree of suppresion in the amount of urine proteins was seen in this group, only a small weight increase was seen in the animals in this group as compared with the animals in the control group. In contrast, the weight increase in the animals to which the purine derivatives of the present invention was administered was almost the same with the animals of the control group, indicating that the compounds of the present invention did not affect the increase in body weight of animals. This suggests that the purine derivatives of the present invention are less toxic than 2-(4-hydroxy-3,5-di-t-butylphenyl)-6-substituted any purine compounds of the Japanese Patent Application Laid-Open No. 7-316158, and can be a superior drug for treating nephritis, administered over a long period of time.

Preparation Example

A preparation example for orally administered tablets containing the purine derivative of the present invention as an active ingredient will be given. In this example, tablets were prepared by a conventional method using a composition consisting of a powder of the compound in Example 21 and the following pharmaceutically acceptable additives in powder form.

| Composition | Content per tablet |
| --- | --- |
| The compound of Example 21 | 100 mg |
| Lactose | 120 mg |
| Potato starch | 30 mg |
| Sodium Hydroxypropylcellulose | 5 mg |
| Carboxymethylcellulose | 7 mg |
| Magnesium stearate | 0.5 mg |

INDUSTRIAL APPLICABILITY

As shown in the above Test Examples, the novel purine derivatives of the present invention exhibit a remarkably suppressive effect of urinary protein excretion in rats of the anti-GBM nephritis model, which is a typical pharmacological model for glomerulone-nephritis. The effect of suppressing urinary protein excretion is due to a pharmacological action different from the protective action due to an increase in the kidney blood flow rate as in the case of the theophylline which is a PDE inhibitor. Accordingly, the pharmaceutical composition which comprises the purine derivative of the present invention or a pharmaceutically acceptable salt thereof is effective in suppressing urinary protein excretion associated with glomerulone-nephritis, and can be an effective medicine for treating glomerulone-nephritis. In addition, because the purine derivatives of the present invention can be orally administered, they can be used as a drug to alleviate or control symptoms caused by various types of primary nephritises such as acute inflammatory response, immunoreaction, and kidney functional disorders due to various blood vessel actuation substances, not to mention chronic glomerulus nephritis, as well as secondary nephritises manifesting as diabetes or hypertension.

What is claimed is:
1. A purine derivative of the following formula (I),

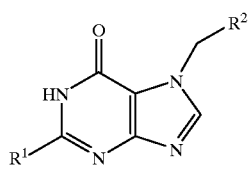

(I)

or a pharmaceutically acceptable salt thereof, wherein
$R^1$ is
  a hydrocarbon group having 17 or less carbon atoms or
  a substituted hydrocarbon group having 17 or less carbon atoms selected from the group consisting of
    (1) hydrocarbon group having 17 or less carbon atoms in which a carbon atom and two hydrogen atoms of one or more >$CH_2$ g roups, —$CH_3$ g roups, or =$CH_2$ g roups which do not directly bind with the carbon atom at 2 position of the purine ring are replaced by carbonyl groups, sulfonyl groups, O, or S,
    (2) hydrocarbon group having 17 or less carbon atoms in which a carbon and one hydrogen atom of one or more >CH— groups, >$CH_2$ g roups, —$CH_3$ g roups, =$CH_2$ g roups, =CH— groups, or ≡CH which do not directly bind with the carbon atom at 2 position of the purine ring are replaced by N, C-halogen, or C—C≡N, or
    (3) hydrocarbon group having 17 or less carbon atoms in which
      (i) a carbon atom and two hydrogen atoms of one or more >$CH_2$ g roups, —$CH_3$ g roups, or =$CH_2$ g roups which do not directly bind with the carbon atom at 2 position of the purine ring are replaced by carbonyl groups, sulfonyl groups, O, or S, and
      (ii) a carbon and one hydrogen atom of one or more >CH— groups, >$CH_2$ g roups, —$CH_3$ groups, =$CH_2$ g roups, =CH— groups, or ≡CH which do not directly bind with the carbon atom at 2 position of the purine ring are replaced by N, C-halogen, or C—C≡N; and
$R^2$ is
  a hydrocarbon group having 16 or less carbon atoms or
  a substituted hydrocarbon group having 16 or less carbon atoms selected from the group consisting of
    (1) hydrocarbon group having 16 or less carbon atoms in which carbon atom and two hydrogen atoms of one or more >CH₂ g roups, —CH₃ g roups, or =CH₂ g roups which do not directly bind with the methylene group at 7 position of the purine ring are replaced by carbonyl groups, sulfonyl groups, O, or S, (2) hydrocarbon group having 16 or less carbon atoms in which a carbon and one hydrogen atom of one or more >CH— groups, >CH₂ g roups, —CH₃ g roups, =CH₂ g roups, =CH— groups, or ≡CH which do not directly bind with the methylene group at 7 position of the purine ring are replaced by N, C-halogen, or C—C≡N, or (3) hydrocarbon group having 16 or less carbon atoms in which (i) a carbon atom and two hydrogen atoms of one or more >CH₂ g roups, —CH₃ g roups, or =CH₂ g roups which do not directly bind with the methylene group at 7 position of the purine ring are replaced by carbonyl groups, sulfonyl groups, O, or S, and (ii) a carbon and one hydrogen atom of one or more >CH— groups, >CH₂ g roups, —CH₃ groups, =CH₂ g roups, =CH— groups, or ≡CH which do not directly bind with the methylene group at 7 position of the purine ring are replaced by, N, C-halogen, or C—C≡N.

2. The purine derivative or pharmaceutically acceptable salt thereof according to claim 1, wherein $R^1$ or $R^2$ contain a cyclic structure of a mono-cyclic hydrocarbon group or a heterocyclic group having a structure in which at least one carbon atom in said mono-cyclic hydrocarbon group is replaced by a sulfur atom or an oxide thereof, nitrogen atom, or-oxygen atom.

3. The purine derivative or pharmaceutically acceptable salt thereof according to claim 1, wherein $R^1$ is a phenyl group, a mono-, di-, or tri-substituted phenyl group or an unsubstituted, or a mono-, di-, or tri-substituted 5- or 6-member ring heterocyclic aromatic group.

4. The purine derivative or pharmaceutically acceptable salt thereof according to claim 1, wherein $R^1$ is a phenyl group either unsubstituted or substituted by one or two substitution groups, or a pyridyl group either unsubstituted or substituted by one or two substitution groups.

5. The purine derivative or pharmaceutically acceptable salt thereof according to claim 1, wherein $R^1$ is selected from the group consisting of ethyl group, propyl group, 2-aminoethyl group, and N-methylaminomethyl group, and $R^2$ is selected from the group consisting of phenyl group, mono-substituted phenyl group, benzyl group, and 2-phenethyl group.

6. The purine derivative of claim 1 wherein $R^2$ is a substituted hydrocarbon represented by formula (A):

  (A)

wherein m is an integer selected from 0, 1, and 2;
n is an integer selected form 0 and 1;

X is selected form the group consisting of —O—, —NH—, —NHCO—, —CONH—, —NHSO₂—, and —SO₂NH—; and Ar is selected from the group consisting of
phenyl and
a substituted phenyl group with 1 to 3 substituents independently selected from the group consisting of an alkyl group having 1–6 carbon atoms, halogeno group, hydroxyl group, alkoxyl group having 1–6 carbon atoms, amino group, amino group susbtituted by one alkyl group having 1–6 carbon atoms, amino group substituted by two alkyl groups having 1–3 carbon atoms, carbamoyl group, N-alkylcarbamoyl group having 1–6 carbon atoms, sulfamoyl group, N-alkylsulfamoyl group having 1–6 carbon atoms, and trifluoromethyl group.

7. The purine derivative of claim 1 wherein $R^2$ is a substituted hydrocarbon represented by formula (B):

  (B)

wherein m is an integer selected from 0, 1, and 2;
Ar is selected from the group consisting of
phenyl and
a substituted phenyl group with 1 to 3 substituents independently selected from the group consisting of an alkyl group having 1–6 carbon atoms, fluoro, chloro, hydroxyl group, alkoxyl group having 1–6 carbon atoms, amino group, amino group substituted by two alkyl groups having 1–3 carbon atoms, and trifluoromethyl group.

8. A pharmaceutical composition comprising an effective amount of the purine derivative or a pharmaceutically acceptable salt thereof according to claim 1, 2, 3, 4, 5, 6, or 7 and a pharmaceutically acceptable carrier.

9. The pharmaceutical composition of claim 8, wherein the carrier comprises carboxymethyl cellulose.

10. A method of treating nephritis comprising providing a pharmaceutical composition of the purine derivative or a pharmaceutically acceptable salt thereof according to claim 1, 2, 3, 4, 5, 6, or 7 and a pharmaceutically acceptable carrier, and providing a pharmaceutical composition of the purine derivative or a pharmaceutically acceptable salt thereof according to claim 1, 2, 3, 4, or 5 and a pharmaceutically acceptable carrier, and administering an effective amount of said pharmaceutical composition to a patient.

11. The pharmaceutical composition according to claim 8, wherein the carrier comprises lactose.

12. The pharmaceutical composition according to claim 8, wherein the carrier comprises sodium hydroxypropylcellulose.

13. The method according to claim 10, wherein the carrier comprises lactose.

* * * * *

UNITED STATES PATENT AND TRADEMARK OFFICE
CERTIFICATE OF CORRECTION

PATENT NO.     : 6,310,070 B1                                              Page 1 of 1
DATED          : October 30, 2001
INVENTOR(S)    : Yokoyama et al.

It is certified that error appears in the above-identified patent and that said Letters Patent is hereby corrected as shown below:

Column 114,
Lines 36, 36-37, 37, 43, 52, 57 and 58, please delete "g roups" and substitute -- groups -- therefor.
Lines 44 and 51, please delete both occurrences "g roups" and substitute -- groups -- therefor.

Column 115,
Lines 1, 1-2, 2, 17, 22, 23, please delete "g roups" and substitute -- groups -- therefor.
Lines 9 and 16, please delete both occurrences "g roups" and substitute -- groups -- therefor.
Line 38 and 51, please insert a comma -- , -- after "group".

Column 116,
Lines 45-48, please delete "providing a pharmaceutical composition of the purine derivative or a pharmaceutically acceptable salt thereof according to claim 1, 2, 3, 4, or 5 and a pharmaceutically acceptable carrier, and".

Signed and Sealed this

Seventeenth Day of September, 2002

Attest:

JAMES E. ROGAN
Attesting Officer    Director of the United States Patent and Trademark Office